(12) United States Patent
Yang et al.

(10) Patent No.: US 11,236,081 B2
(45) Date of Patent: Feb. 1, 2022

(54) CRYSTALLINE SALTS OF CORYDALMINE

(71) Applicant: Zheng Yang, Beijing (CN)

(72) Inventors: Zheng Yang, Beijing (CN); Zheng Jane Li, Beijing (CN); Zhicong Shi, Beijing (CN)

(73) Assignee: Zheng Yang, Beijing (CN)

( * ) Notice: Subject to any disclaimer, the term of this patent is extended or adjusted under 35 U.S.C. 154(b) by 0 days.

(21) Appl. No.: 16/612,379

(22) PCT Filed: Nov. 29, 2018

(86) PCT No.: PCT/CN2018/118203
§ 371 (c)(1),
(2) Date: Nov. 9, 2019

(87) PCT Pub. No.: WO2020/107335
PCT Pub. Date: Jun. 4, 2020

(65) Prior Publication Data
US 2021/0347770 A1    Nov. 11, 2021

(51) Int. Cl.
*C07D 455/03* (2006.01)

(52) U.S. Cl.
CPC ........ *C07D 455/03* (2013.01); *C07B 2200/13* (2013.01)

(58) Field of Classification Search
CPC .................................................. C07D 455/03
See application file for complete search history.

(56) References Cited

FOREIGN PATENT DOCUMENTS

| | | | |
|---|---|---|---|
| CN | 103214477 A | | 7/2013 |
| CN | 106176740 A | * | 7/2016 |
| CN | 106176740 A | | 12/2016 |
| CN | 106237333 A | | 12/2016 |
| CN | 107260738 A | | 10/2017 |
| WO | 2009002873 A1 | | 12/2008 |

* cited by examiner

*Primary Examiner* — Paul V Ward
(74) *Attorney, Agent, or Firm* — Locke Lord LLP

(57) ABSTRACT

The present disclosure relates to crystalline salt forms of the following Compound (1), also known as l-corydalmine or l-CDL, and methods for the preparation thereof, pharmaceutical compositions thereof, and their use in methods for the treatment of chronic pain, anxiety, insomnia, hyperlipidemia, hypercholesterolemia, hypertriglyceridemia, hepatic steatosis, and metabolic syndrome, et al.

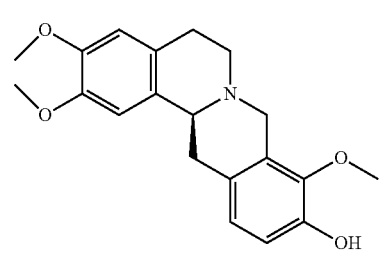

Compound (1)

19 Claims, 40 Drawing Sheets

(a)

(b)

CRYSTALLINE SALTS OF CORYDALMINE

BACKGROUND

1. Field of the Discovery

The present disclosure relates to crystalline salt forms of the following Compound (1), also known as l-corydalmine or l-CDL, and methods for the preparation thereof, pharmaceutical compositions thereof, and their use in methods for the treatment of chronic pain, anxiety, insomnia, hyperlipidemia, hypercholesterolemia, hypertriglyceridemia, hepatic steatosis, and metabolic syndrome, et al.

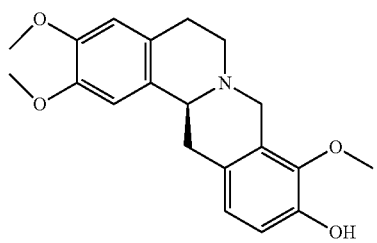

Compound (1)

2. Background Information

Compound (1), also known as l-corydalmine or l-CDL, has CAS Number: 30413-84-4. Compound (1) is a free base with an acid pKa of approximately 5.2. There is a need to produce Compound (1) in a form sufficient to enable formulations to meet exacting pharmaceutical requirements and specifications, while providing sufficient in-vivo exposure of the active drug. Further, the process by which Compound (1) is produced needs to be one which is amenable to large-scale production. Additionally, it is desirable that the product should be in a form that is easily processed, e.g. readily filterable and easily dried. Finally, it is desirable that the drug product of Compound (1) be stable for extended periods of time without the need for 3 specialized storage conditions. Therefore, there is a need to identify crystalline pharmaceutically acceptable salts of Compound (1).

In addition, many salt forms can exist in different crystal polymorphs, which exhibit different physical, chemical, and spectroscopic properties. For example, certain polymorphs of a salt may be more readily soluble in particular solvents, may flow more readily, or may compress more easily than others. For a drug candidate, certain polymorphs may be more bioavailable than others, while others may be more stable under certain manufacturing, storage, and biological conditions. This is particularly important from a regulatory standpoint, since drugs are approved by agencies such as the U.S. Food and Drug Administration only if they meet exacting purity and characterization standards. Indeed, the regulatory approval of one polymorph of a compound, which exhibits certain solubility and physico-chemical (including spectroscopic) properties, typically does not imply the ready approval of other polymorphs of that same compound. Therefore, there is a need to identify polymorphs of a salt that can provide a variety of advantages.

SUMMARY

The present disclosure relates to crystalline salt forms of the following Compound (1), also known as l-corydalmine or l-CDL, and methods for the preparation thereof, pharmaceutical compositions thereof, and their use in methods for the treatment of chronic pain, anxiety, insomnia, hyperlipidemia, hypercholesterolemia, hypertriglyceridemia, hepatic steatosis, and metabolic syndrome, et al.

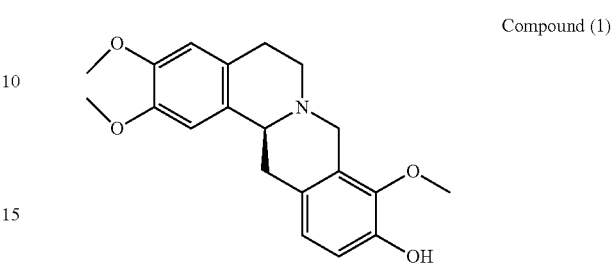

Compound (1)

In one aspect, the present disclosure relates to a crystalline salt form of Compound (1). In one specific aspect, the present disclosure relates to a crystalline hydrochloride, oxalate, maleate, sulfate, or mesylate salt form of Compound (1).

In one aspect, the present disclosure relates to a crystalline hydrochloride salt form of Compound (1). In one specific aspect, the crystalline hydrochloride salt form of Compound (1) is characterized by an X-ray powder diffraction ("MOD") pattern comprising peaks selected from the group at approximately 9.7, 10.1, 14.3, 15.0, 17.2, 17.5, 18.9, 21.0, 21.4, 21.9, and 23.7 degrees 2θ and/or a differential scanning calorimetry ("DSC") thermogram endotherm $T_{onset}$ at approximately 252° C.

In one aspect, the present disclosure relates to a crystalline oxalate salt form of Compound (1). In one specific aspect, the crystalline oxalate salt form of Compound (1) is characterized by an X-ray powder diffraction pattern comprising peaks selected from the group at approximately 11.7, 13.0, 15.4, 16.3, 19.0, 19.6, 20.4, 22.1, 24.5, and 25.2 degrees 2θ and/or a differential scanning calorimetry thermogram endotherm $T_{onset}$ at approximately 205° C.

In one aspect, the present disclosure relates to a crystalline maleate salt form of Compound (1). In one specific aspect, the crystalline maleate salt form of Compound (1) is characterized by an X-ray powder diffraction pattern comprising peaks selected from the group at approximately 8.0, 10.4, 12.4, 14.0, 15.3, 16.4, 19.3, 20.8, 21.5, and 23.3 degrees 2θ and/or a differential scanning calorimetry thermogram endotherm $T_{onset}$ at approximately 193° C.

In one aspect, the present disclosure relates to a crystalline sulfate salt form of Compound (1). In one specific aspect, the crystalline sulfate salt form of Compound (1) is characterized by an X-ray powder diffraction pattern comprising peaks selected from the group at approximately 8.4, 12.6, 13.7, 16.0, 16.7, 21.0, 21.8, 22.2, 23.4, and 27.5 degrees 2θ and/or a differential scanning calorimetry thermogram endotherm $T_{onset}$ at approximately 229° C.

In one aspect, the present disclosure relates to a crystalline mesylate salt form of Compound (1). In one specific aspect, the crystalline mesylate salt form of Compound (1) is characterized by an X-ray powder diffraction pattern comprising peaks selected from the group at approximately 7.9, 11.3, 12.6, 12.9, 14.7, 16.1, 18.8, 20.0, 20.7, and 23.6 degrees 2θ and/or a differential scanning calorimetry thermogram endotherm $T_{onset}$ at approximately 238° C.

In one aspect, the present disclosure provides a pharmaceutical composition comprising any of the crystalline salt forms disclosed herein and a pharmaceutically acceptable carrier. In some specific aspects, the pharmaceutical composition is a single unit dosage form, and/or contains a substantially pure crystalline salt form disclosed herein.

In one aspect, the present disclosure provides a method of treating chronic pain, anxiety, insomnia, hyperlipidemia, hypercholesterolemia, hypertriglyceridemia, hepatic steatosis, and metabolic syndrome in a mammal comprising administering to the mammal a therapeutically-effective amount of any of the pharmaceutical compositions disclosed herein.

In another aspect, the present disclosure provides a method of treating chronic pain, anxiety, insomnia, hyperlipidemia, hypercholesterolemia, hypertriglyceridemia, hepatic steatosis, and metabolic syndrome in a mammal comprising administering to the mammal a pharmaceutical composition comprising a therapeutically-effective amount of any of the crystalline salt forms disclosed herein. The administration step can be carried out by oral, intravenous, intramuscular or subcutaneous in the amount of about 1 mg to about 1,000 mg, in the amount of about 5 mg to about 500 mg, in the amount of about 10 mg to about 200 mg, in the amount of about 10 mg to about 150 mg, in the amount of about 10 mg to about 120 mg, in the amount of about 10 mg, in the amount of about 20 mg, in the amount of about 40 mg, in the amount of about 80 mg, or in the amount of about 120 mg.

Further aspects, features, and advantages of the present disclosure will be apparent to those of ordinary skill in the art upon examining and reading the following detailed description.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
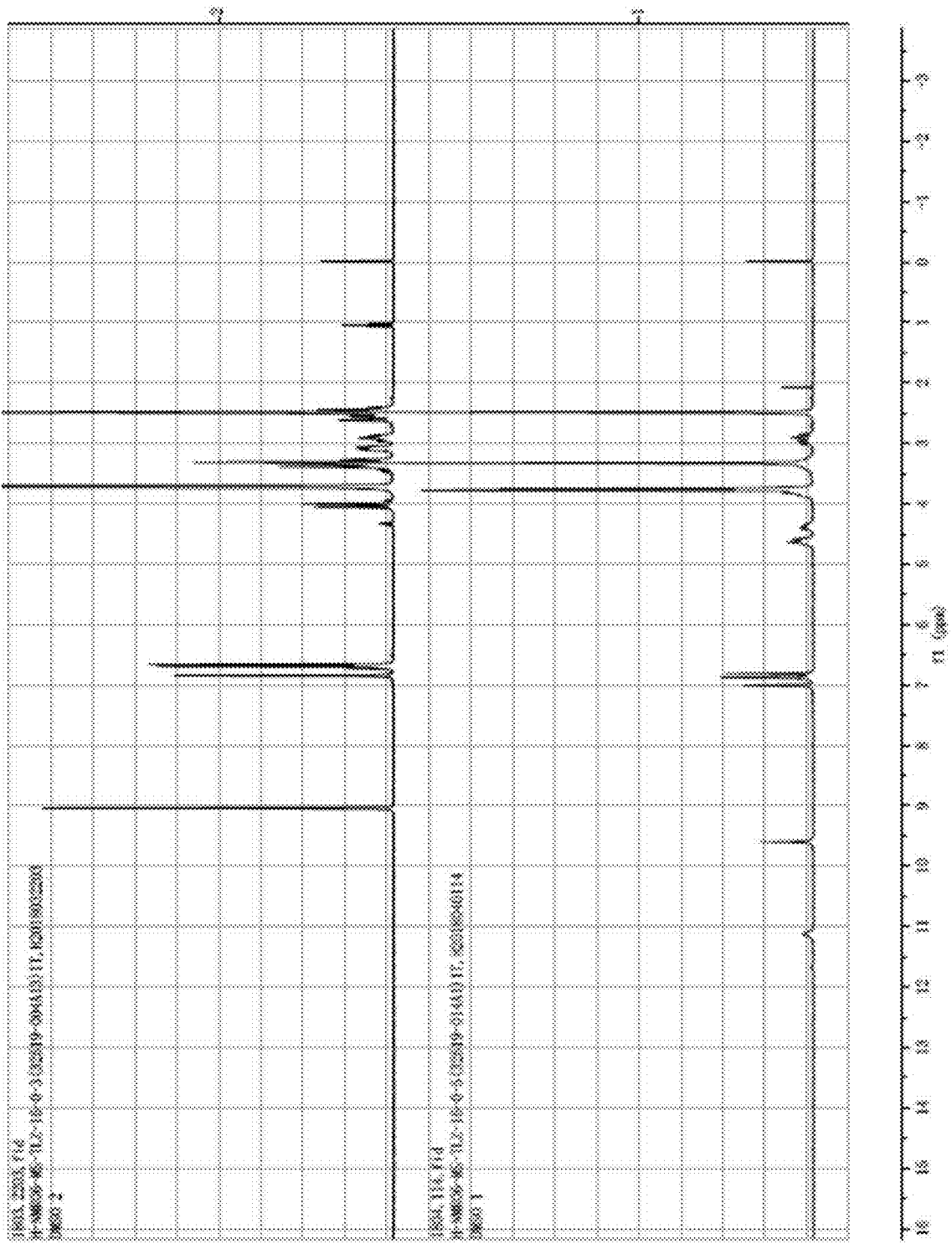
FIG. 1 illustrates a representative $^1$HNMR spectrum of hydrochloride salt of Compound (1).

The following is a detailed description provided to aid those skilled in the art in practicing the present disclosure. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

The present description provides crystalline salt forms of the following Compound (1), also known as l-corydalmine or l-CDL, and methods for the preparation thereof, pharmaceutical compositions thereof, and their use in methods for the treatment of chronic pain, anxiety, insomnia, hyperlipidemia, hypercholesterolemia, hypertriglyceridemia, hepatic steatosis, and metabolic syndrome, et al.

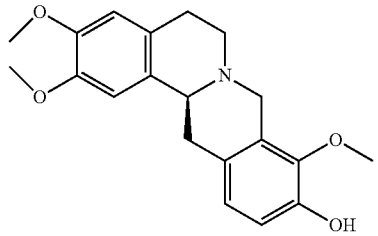

Compound (1)

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

The following terms are used to describe the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, the term "pharmaceutically acceptable" with respect to a substance as used herein means that substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

As used herein in the specification and in the claims, the terms "treat," "treating" and "treatment" refer to the alleviation of a disease or disorder and/or at least one of its attendant symptoms.

As used herein in the specification and in the claims, the terms "polymorph" and "polymorphic form" refer to solid crystalline forms of a compound or a complex, such as a solvate or a hydrate. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein to refer to the spectra or data presented in graphical form (e.g.,)(RFD, DSC and NMR spectra), and unless otherwise indicated, the term "peak" refers to a peak or other special feature that one skilled in the art would recognize as not attributable to background noise.

General Analytical Methods

X-ray powder diffraction Analysis (XRPD) The solid samples were determined by powder X-ray diffractometer (Bruker D8 advance) with LynxEye detector. The instrument parameters were listed below.

| Scan: | 3 degree 2θ to 40 degree 2θ |
|---|---|
| Increment: | 0.02 degree 2θ |
| Scan speed: | 0.3 sec/step |
| Voltage: | 40 KV |
| Current: | 40 mA |
| Rotation: | On |
| Sample holder: | Zero-background sample holder |

It should be understood that relative intensities may vary depending on various factors, including sample preparation, instrumentation, and installation procedures and setting and for obtaining molecular spectrum. Therefore, the peak assignments listed herein are intended to include a variation of plus or minus 0.2 degrees 2θ.

Thermogravimetric analysis (TGA) Total weight loss was obtained on a TA Discovery TGA 55. The sample was heated in a tared aluminum pan, ramping 10° C./min to the final temperature.

Differential scanning calorimetry analysis (DSC) Thermal analysis was performed using a TA Discovery DSC 250. The sample was heated in an aluminum pin-hole hermetic pan, ramping 10° C./min with 50 mL/min nitrogen purge to the final temperature. Note that the temperatures may vary depending on various factors, including sample preparation, instrumentation, and sample purity. Therefore, the temperatures reported herein are intended to include a variation of plus or minus 0.5° C.

Polarizing Microscope (PLM)

PLM analysis was performed on a Polarizing Microscope ECLIPSE LV100POL (Nikon, JPN).

$^1$H NMR Analysis $^1$H NMR was performed using Bruker Advance 300 equipped with automated sampler (B-ACS 120).

Dynamic Vapor Sorption (DVS)

DVS was determined using DVS Intrinsic (SMS, UK). Transfer about 20 to 50 mg of the compound into a SMS dynamic vapor sorption model DVS and record the weight change with respect to a varying atmospheric humidity at 25° C. Use the following parameters:

| Equilibrium: | 60 min |
|---|---|
| RH (%) measurement points: | |
| Adsorption: | 0, 10, 20, 30, 40, 50, 60, 70, 80, 90 |
| Desorption: | 90, 80, 70, 60, 50, 40, 30, 20, 10, 0 |

Hydrochloride Salt of Compound (1)

Hydrochloride Salt of Compound (1) exhibits multiple crystalline polymorphs.

Form I

Hydrochloride ("HCl") salt Form I can be obtained from various solvents, including, but not limited to Acetone, isopropanol ("IPA"), or ethyl acetate ("EtOAc"). In some embodiment, Form I of crystalline hydrochloride salt was prepared by adding concentrated HCl aqueous solution (12 mol/L) to Compound (1) free base solutions of Acetone, IPA, or EtOAc, and Table 1 lists the details of the experimental conditions. In one specific embodiment, 1.07 g free base reacted with 333.3 μL HCl in 25 mL Acetone by stirring overnight, the crystalline solids were filtered and dried at 40° C., under vacuum. Form I was characterized by $^1$HNMR, XRPD, PLM, DVS, TGA and DSC.

TABLE 1

Preparation of Form I of hydrochloride salt (1 eq. concentrated HCl)

| Lot | Solvent | Volume (μL) | Solid (mg) | Anti-solvent (μL) | |
|---|---|---|---|---|---|
| 32519-014A1 | Acetone | 700 | 30.5 | N/A | N/A |
| 32519-019A1 | | 2200 | 100.5 | N/A | N/A |
| 32519-014B1 | IPA | 5000 | 29.7 | Heptane | 2500 |
| 32519-016A1 | EtOAc | 1800 | 30.9 | N/A | N/A |

FIG. 1 shows a representative $^1$HNMR spectrum of Form I. The $^1$HNMR spectrum shows that there is −0.17 chemical shift occurred near 6.84 ppm, indicating that free base converts into salt with HCl.

Figure 2:
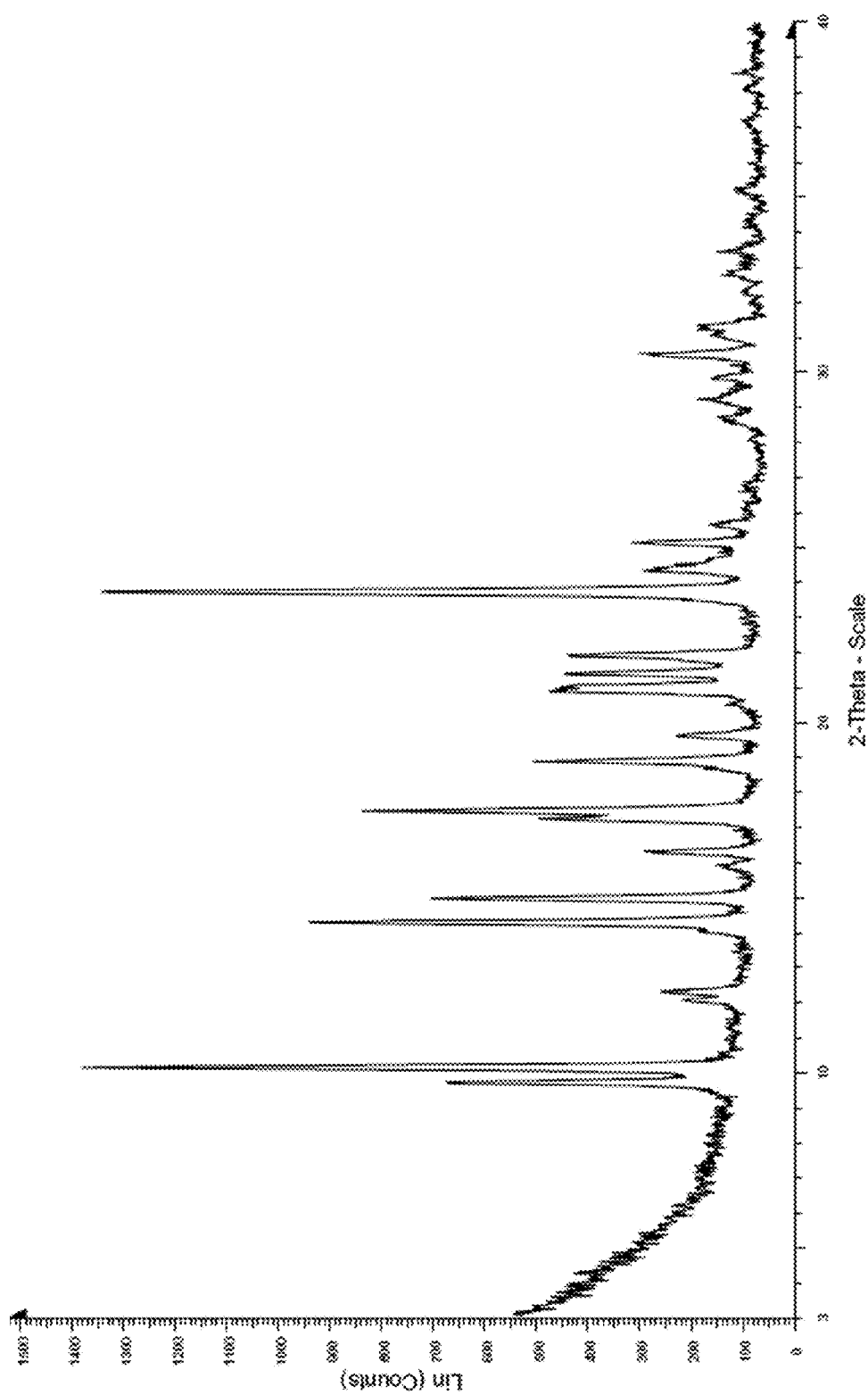
FIG. 2 illustrates a representative XRPD pattern of hydrochloride salt Form I of Compound (1).

FIG. 2 shows a representative XRPD pattern of Form I. The pattern is characterized by peaks, preferably three or more significant peaks, at approximately 9.7, 10.1, 14.3, 15.0, 17.2, 17.5, 18.9, 21.0, 21.4, 21.9, and 23.7 degrees 2θ.

XRPD pattern illustrates that Form I crystals has good crystallinity. Table 2 lists the XRPD peaks of Form I of hydrochloride salt.

TABLE 2

List of representative XRPD peaks of hydrochloride salt Form I

| | Angle 2-Theta degree | Intensity % % | d value Angstrom |
|---|---|---|---|
| 1 | 9.693 | 48.6 | 9.11751 |
| 2 | 10.118 | 100 | 8.73526 |
| 3 | 12.038 | 15.5 | 7.34598 |
| 4 | 12.28 | 18.5 | 7.20205 |
| 5 | 14.027 | 14.1 | 6.30851 |
| 6 | 14.28 | 68 | 6.19753 |
| 7 | 14.95 | 50.9 | 5.92118 |
| 8 | 15.901 | 10.8 | 5.56902 |
| 9 | 16.305 | 20.8 | 5.43208 |
| 10 | 17.243 | 35.8 | 5.13864 |
| 11 | 17.465 | 60.7 | 5.07365 |
| 12 | 18.637 | 15.1 | 4.75713 |
| 13 | 18.898 | 36.4 | 4.69202 |
| 14 | 19.616 | 16.3 | 4.52191 |
| 15 | 20.52 | 8.7 | 4.3248 |
| 16 | 20.971 | 33.3 | 4.23276 |
| 17 | 21.402 | 32.1 | 4.14846 |
| 18 | 21.914 | 31.6 | 4.0526 |
| 19 | 23.469 | 19.3 | 3.78751 |
| 20 | 23.748 | 97.3 | 3.74374 |
| 21 | 24.378 | 20.2 | 3.64837 |
| 22 | 25.138 | 22.5 | 3.53972 |
| 23 | 25.666 | 11.8 | 3.46807 |
| 24 | 26.181 | 6.6 | 3.40097 |
| 25 | 28.113 | 6.4 | 3.17156 |
| 26 | 28.721 | 10.5 | 3.10582 |
| 27 | 29.234 | 13.3 | 3.0524 |
| 28 | 29.884 | 11.1 | 2.98753 |
| 29 | 30.541 | 20.2 | 2.92475 |
| 30 | 31.086 | 11.6 | 2.8747 |
| 31 | 31.482 | 18.5 | 2.83937 |
| 32 | 32.34 | 7.2 | 2.76598 |
| 33 | 32.836 | 8.8 | 2.72533 |
| 34 | 33.506 | 10.7 | 2.67235 |
| 35 | 34.358 | 6.9 | 2.60802 |
| 36 | 35.209 | 7 | 2.54691 |
| 37 | 37.203 | 7.2 | 2.41488 |
| 38 | 38.146 | 6.9 | 2.35732 |
| 39 | 38.62 | 7.6 | 2.32943 |

Figure 3:
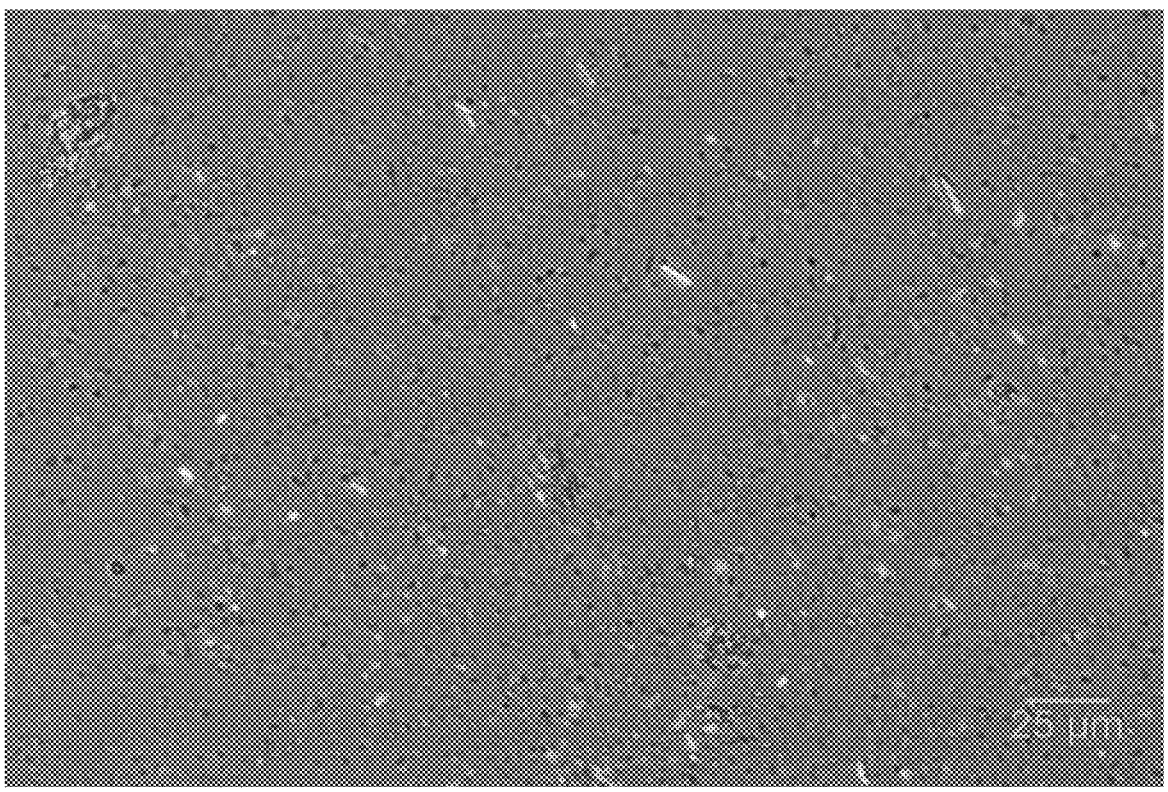
FIG. 3 illustrates a representative polarized light microscopy ("PLM") image of hydrochloride salt Form I of Compound (1).

Representative PLM image are shown in FIG. 3, which illustrates that Form I is rod-like crystalline solid.

Figure 4:
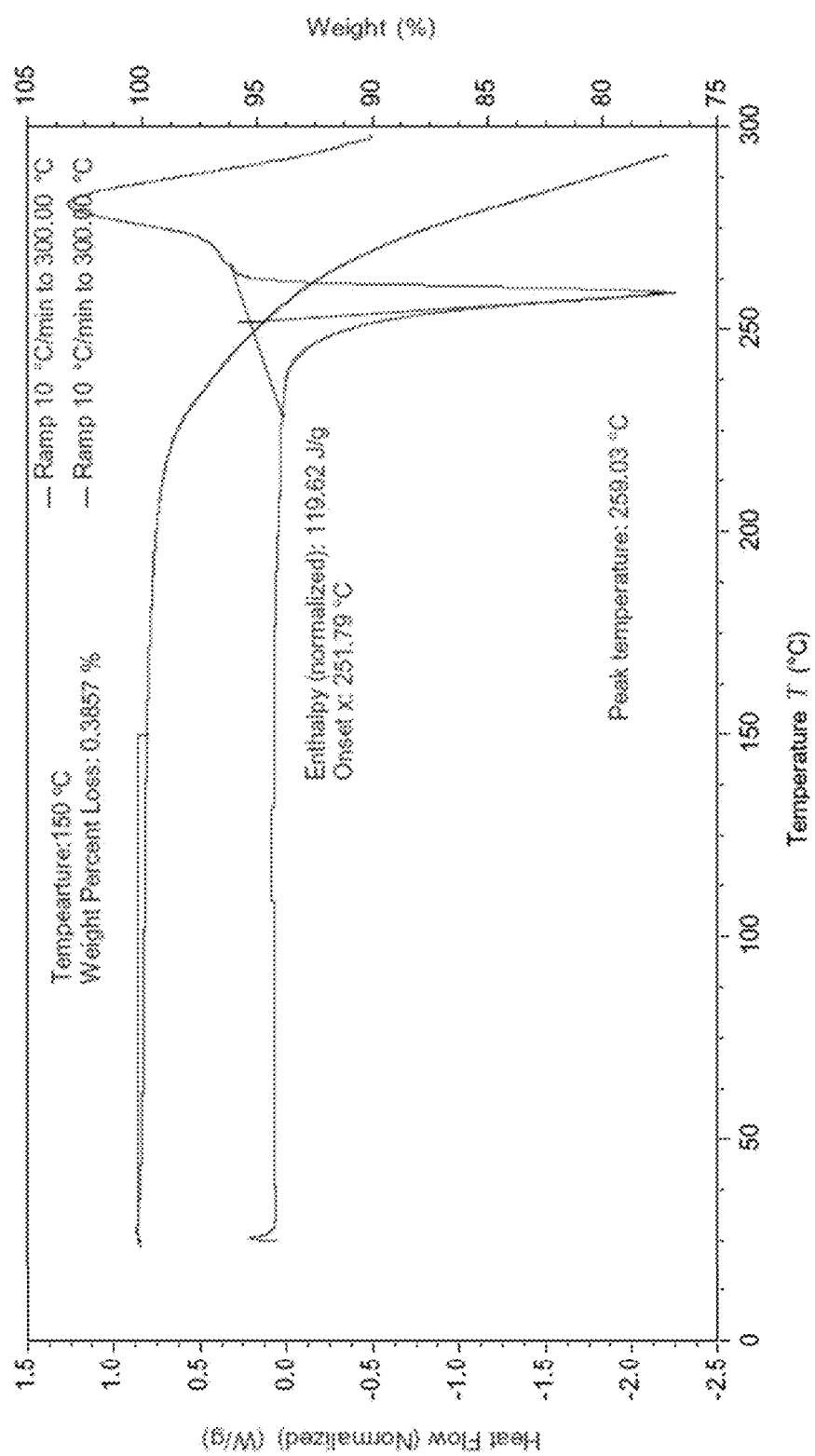
FIG. 4 illustrates representative differential scanning calorimetry ("DSC") and thermogravimetric analysis ("TGA") profiles of hydrochloride salt Form I of Compound (1).

Representative thermal characteristics of Form I are shown in FIG. 4. TGA data indicates that there is −0.3% weight loss between RT and 150° C., and the residual solvent is low. DSC data illustrates that Form I has one endothermic peak with the onset and peak temperatures of 252 and 259° C. respectively, and the enthalpy of the endothermic peak is about 120 J/g.

Figure 5:
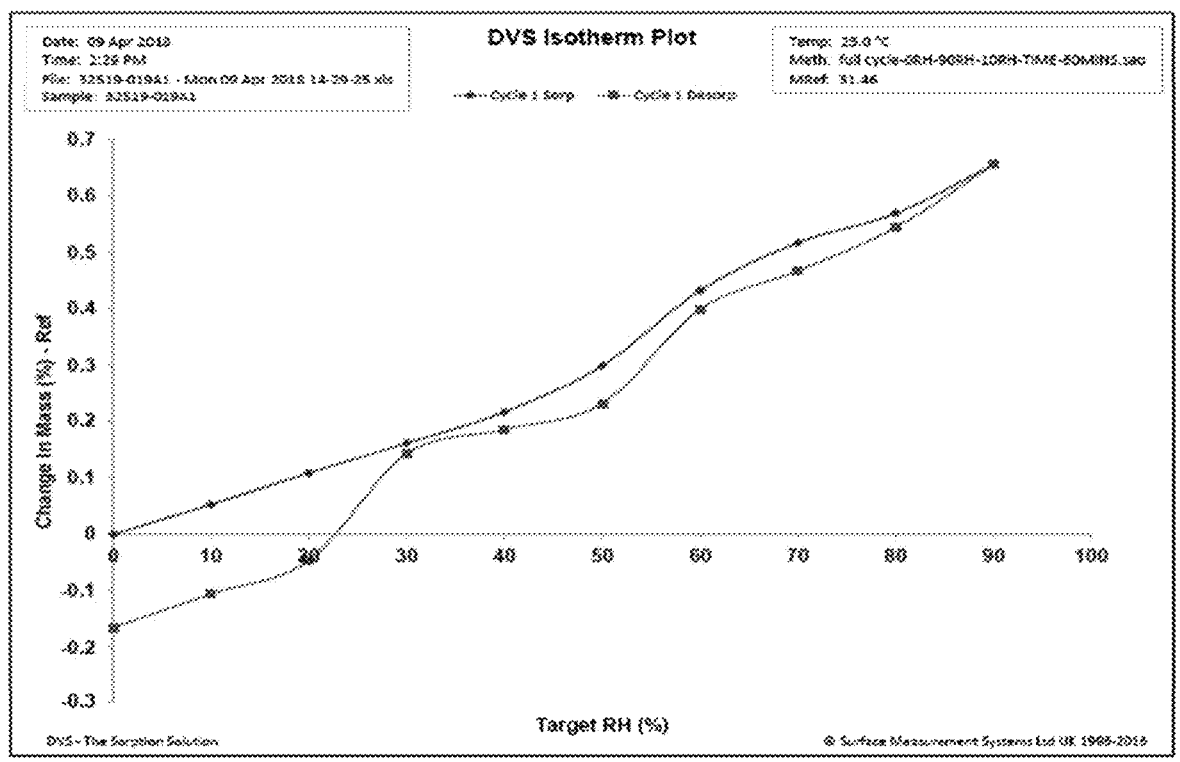
FIG. 5 illustrates representative dynamic vapor sorption ("DVS") profiles of hydrochloride salt Form I of Compound (1).
Figure 5:
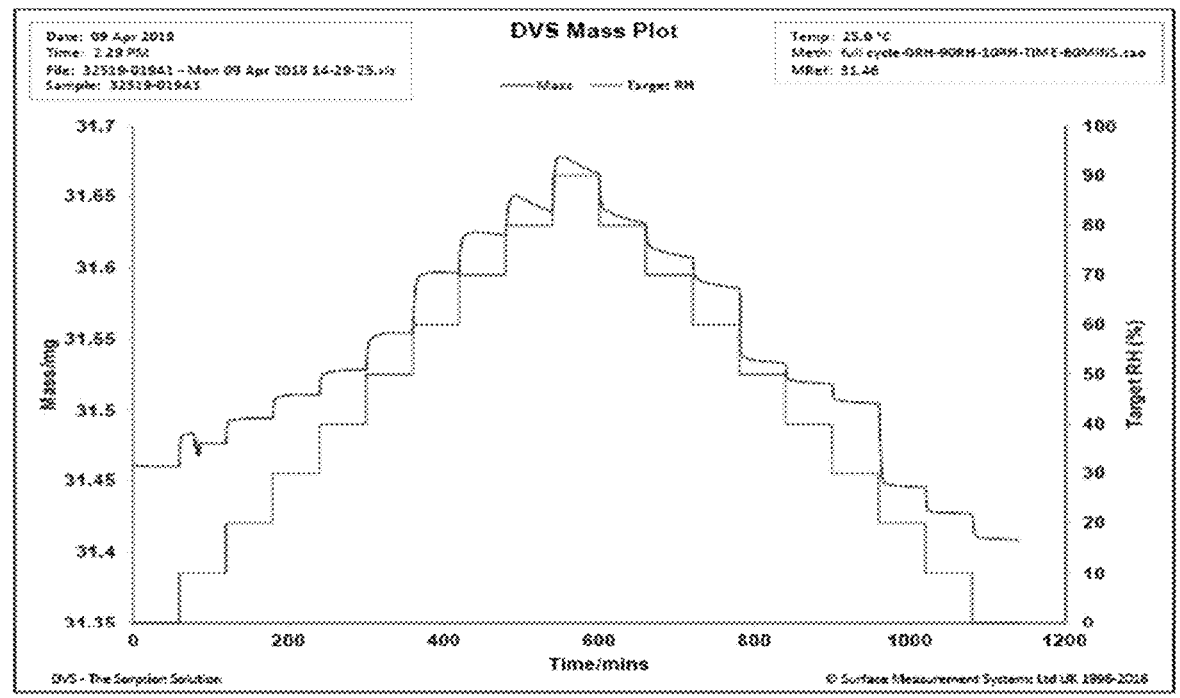

Representative DVS data are plotted in FIG. 5, which suggest that Form I of hydrochloride salt is slightly hygroscopic, and absorb about 0.57% at 80% RH. The solid form does not change after DVS test.

Solubility studies of Form I hydrochloride salt in water at 2 hours were higher than that of the free base, which were improved from free base solubility of less than 1 mg/mL to the Form I hydrochloride salt solubility of approximately 19.1 mg/mL.

Form II

Hydrochloride salt Form II can be obtained from methanol. In one embodiment, Form II can be obtained by stirring a Hydrochloride salt Form I slurry in methanol at RT for 3 days, and/or stirring the slurry at 50° C. for one day. In another embodiment, Form II can be obtained by evaporate a saturated hydrochloride salt methanol solution. In yet another embodiment, Form II can be obtained by adding an anti-solvent, e.g. methyl t-butyl ether ("MTBE"), Toluene, EtOAc, or IPA, into a methanol solution.

Figure 6:
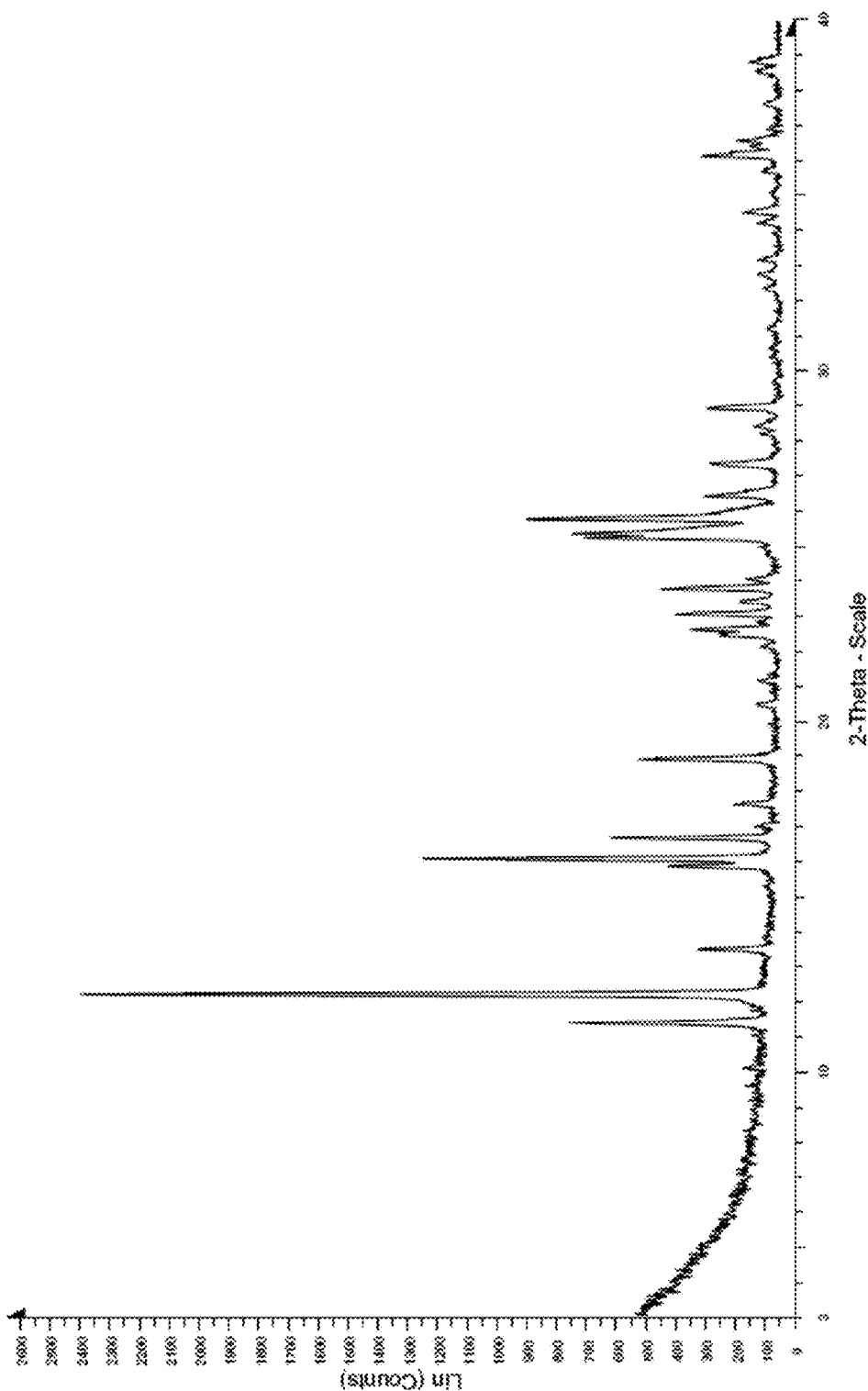
FIG. 6 illustrates a representative XRPD pattern of hydrochloride salt Form II of Compound (1).
Figure 7:
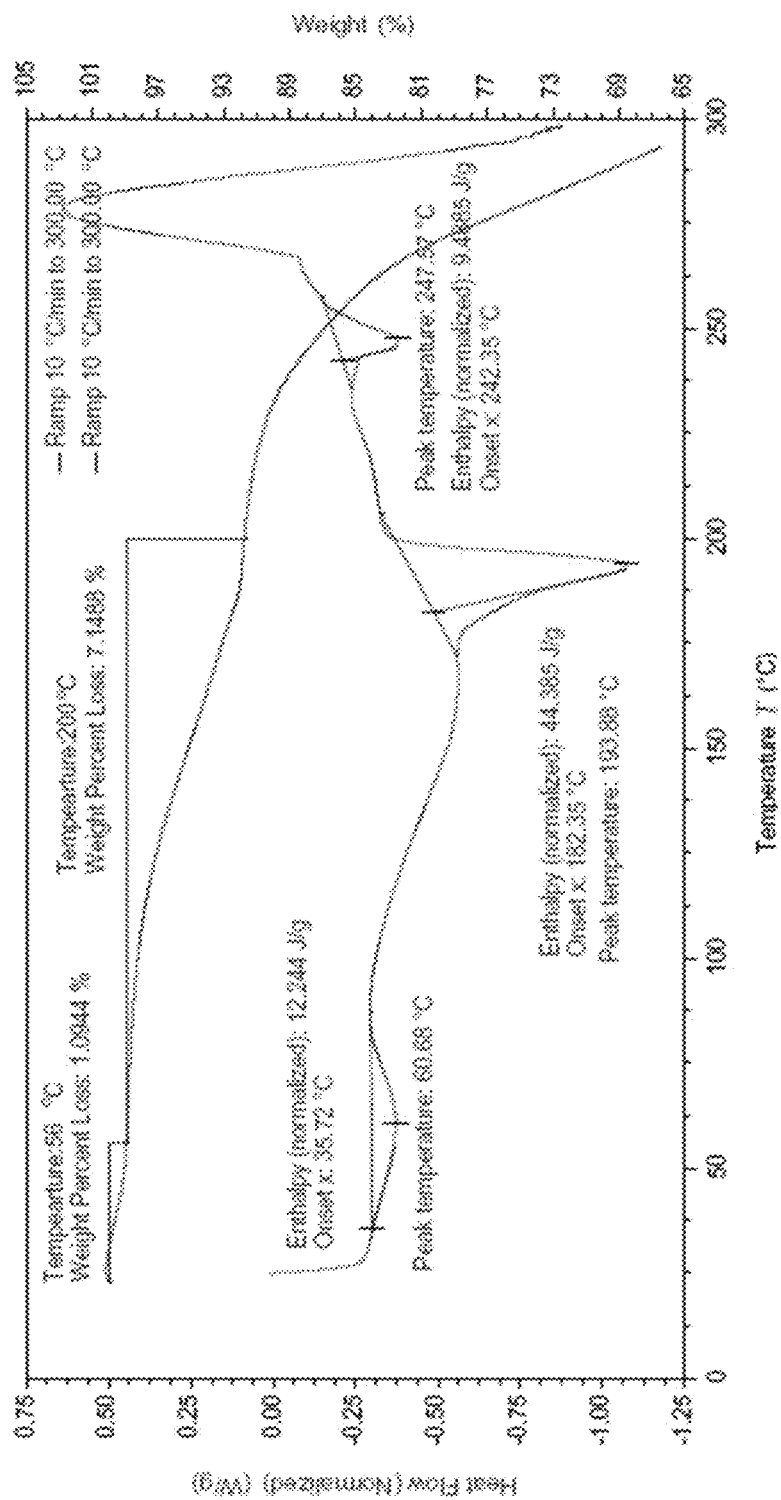
FIG. 7 illustrates representative DSC and TGA profiles of hydrochloride salt Form II of Compound (1).

FIG. 6 shows a representative XRPD pattern of Form II. Representative thermal characteristics of Form II are shown in FIG. 7. The TGA and DSC data further indicate that Form II is a methanol solvate.

Form III

Hydrochloride salt Form III can be obtained from ethanol. In one embodiment, Form III can be obtained by stirring a Hydrochloride salt Form I slurry in ethanol at RT for 3 days, and/or stirring the slurry at 50° C. for one day.

Figure 8:
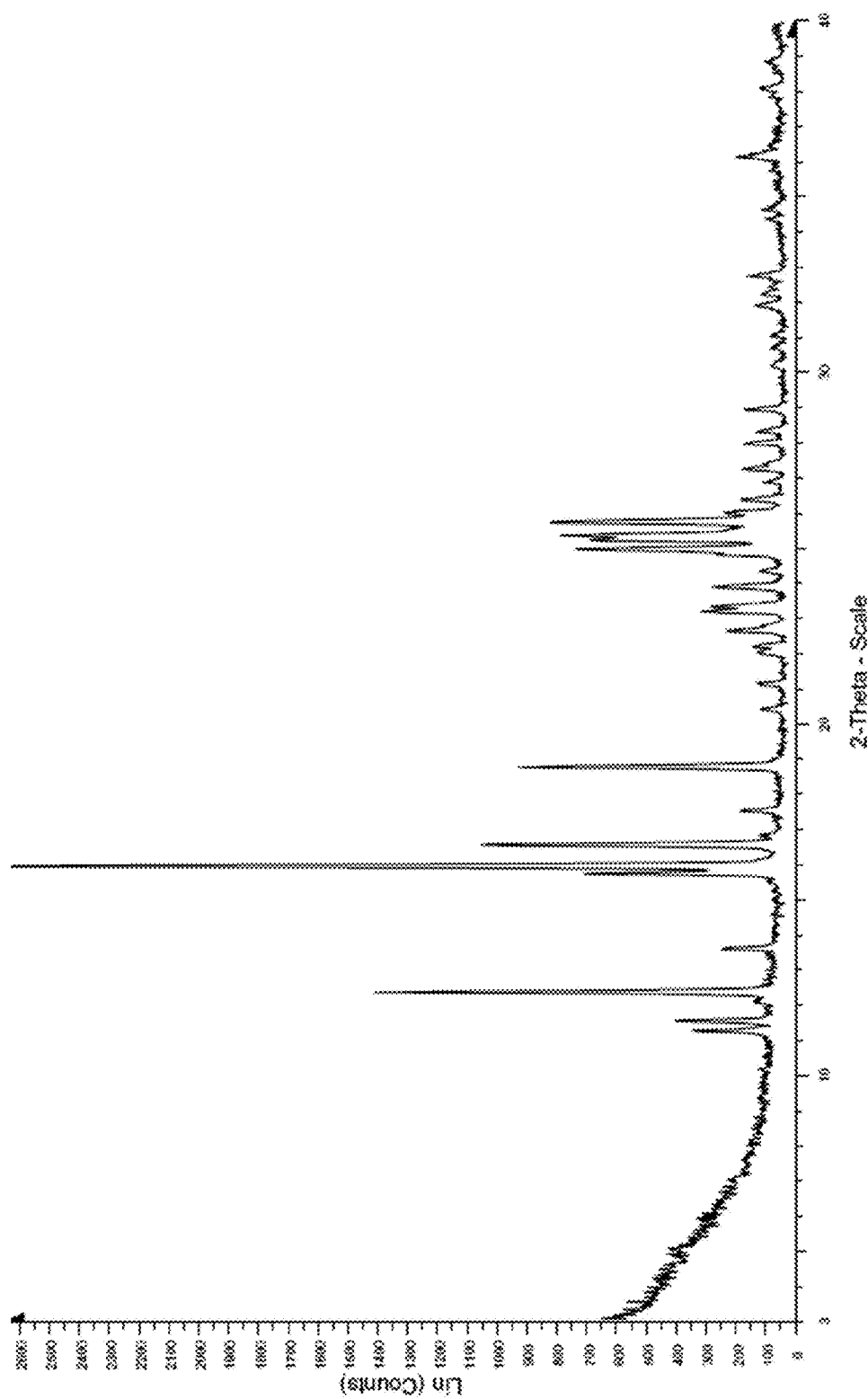
FIG. 8 illustrates a representative XRPD pattern of hydrochloride salt Form III of Compound (1).
Figure 9:
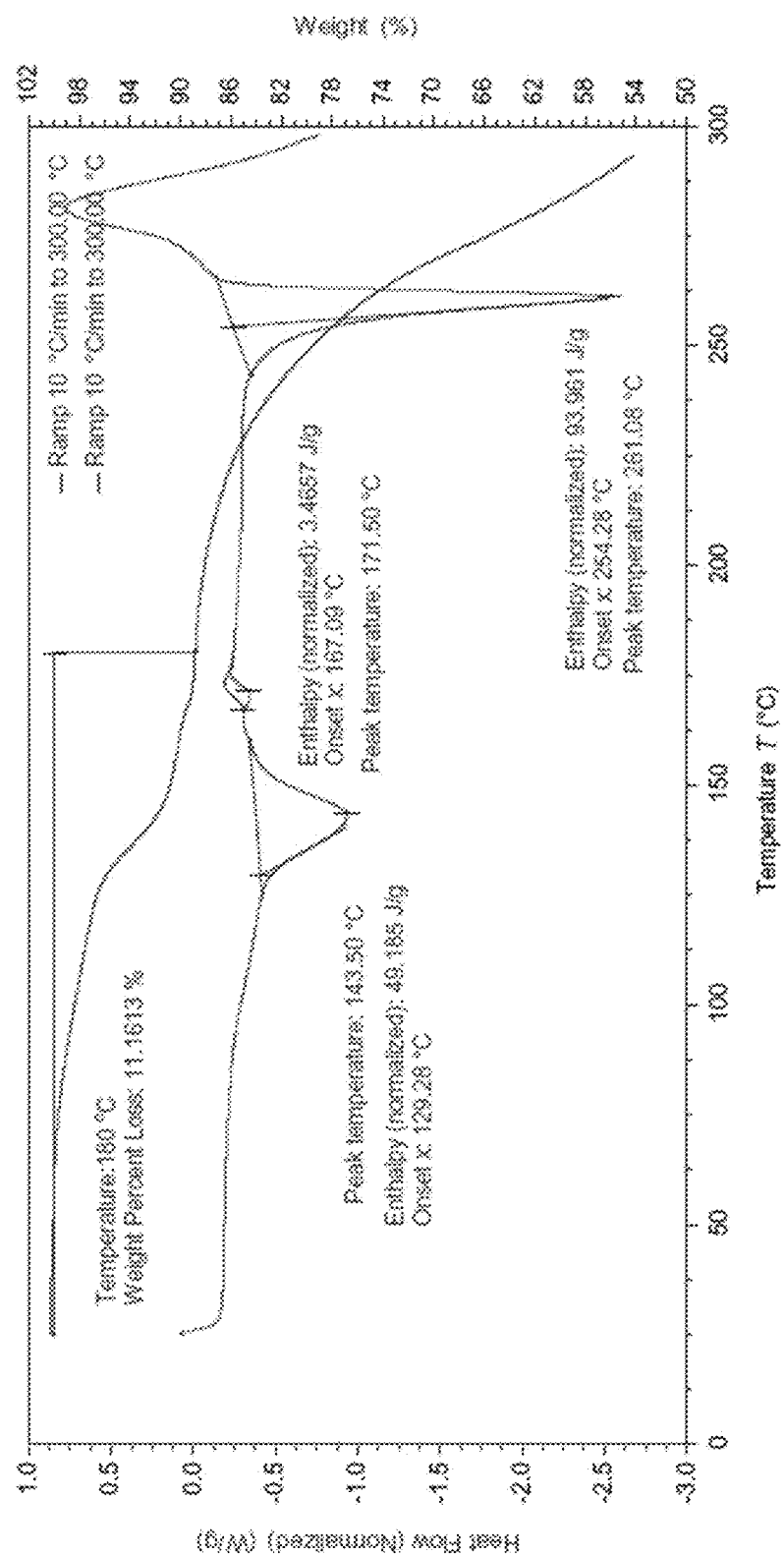
FIG. 9 illustrates representative DSC and TGA profiles of hydrochloride salt Form III of Compound (1).

FIG. 8 shows a representative XRPD pattern of Form III. Representative thermal characteristics of Form III are shown in FIG. 9. The TGA and DSC data further indicate that Form III is an ethanol solvate.

Form IV

Hydrochloride salt Form IV can be obtained from water. In one embodiment, Form IV can be obtained by stirring a Hydrochloride salt Form I slurry in water at RT for 3 days.

Figure 10:
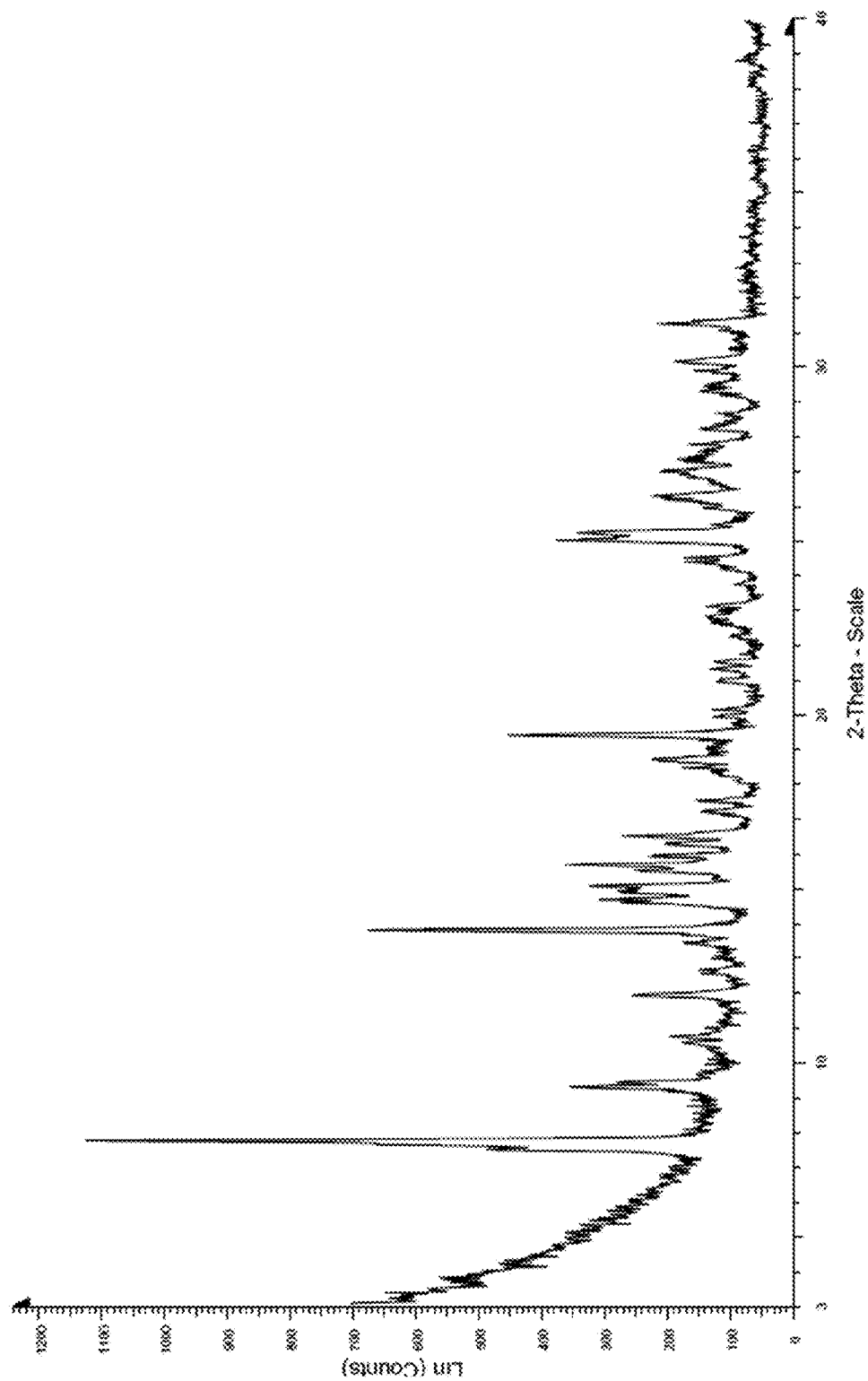
FIG. 10 illustrates a representative XRPD pattern of hydrochloride salt Form IV of Compound (1).
Figure 11:
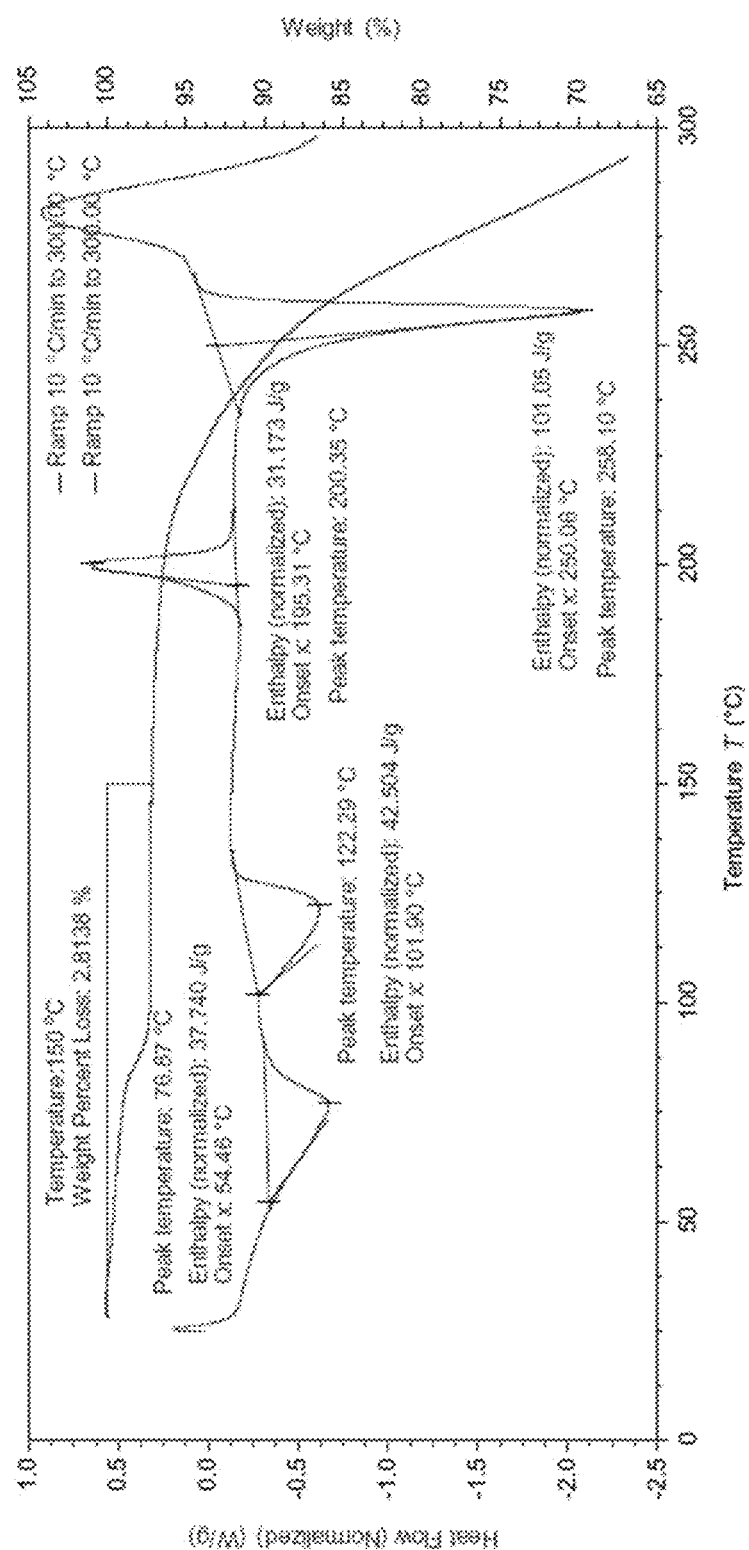
FIG. 11 illustrates representative DSC and TGA profiles of hydrochloride salt Form IV of Compound (1).

FIG. 10 shows a representative XRPD pattern of Form IV. Representative thermal characteristics of Form IV are shown in FIG. 11. The TGA and DSC data further indicate that Form IV is a hydrate.

Form V

Hydrochloride salt Form V can be obtained from water. In one embodiment, Form V can be obtained by stirring a Hydrochloride salt Form I slurry in water at RT 50° C. for one day.

Figure 12:
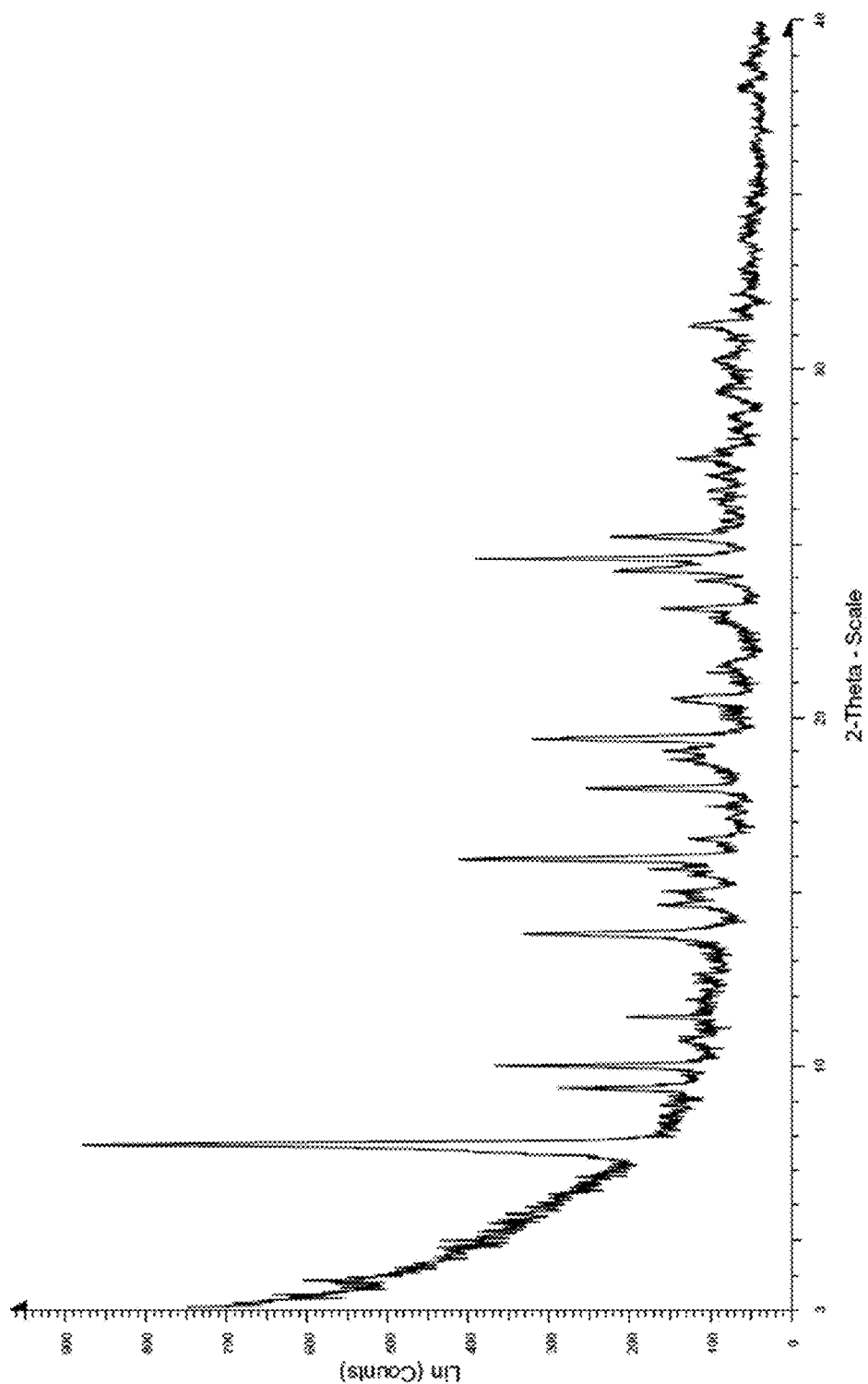
FIG. 12 illustrates a representative XRPD pattern of hydrochloride salt Form V of Compound (1).
Figure 13:
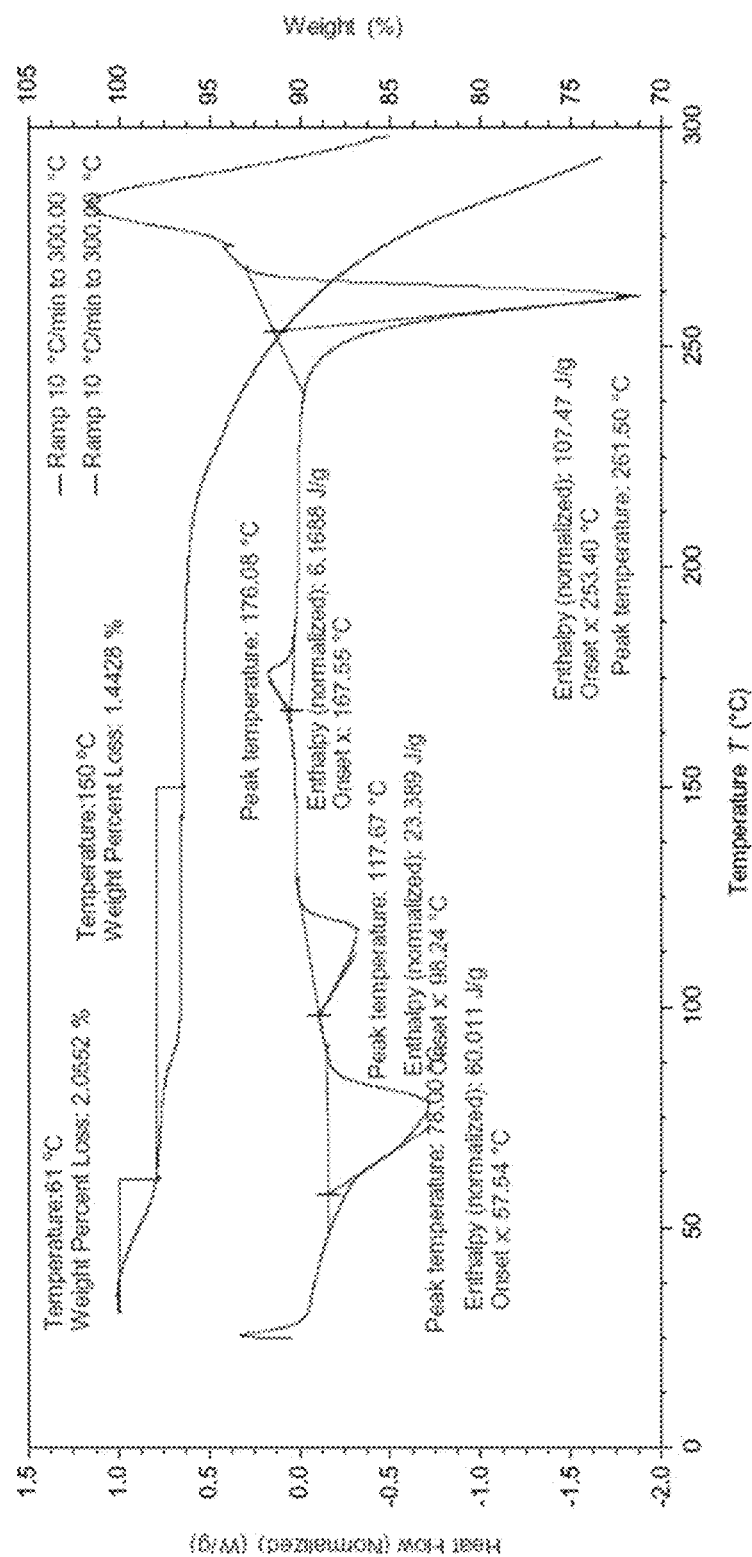
FIG. 13 illustrates representative DSC and TGA profiles of hydrochloride salt Form V of Compound (1).

FIG. 12 shows a representative XRPD pattern of Form V. Representative thermal characteristics of Form V are shown in FIG. 13. The TGA and DSC data further indicate that Form V is a hydrate.

Form VI

Hydrochloride salt Form VI can be obtained from acetonitrile ("ACN"). In one embodiment, Form VI can be obtained by stirring a hydrochloride salt Form I slurry in acetonitrile at RT 50° C. for one day.

Figure 14:
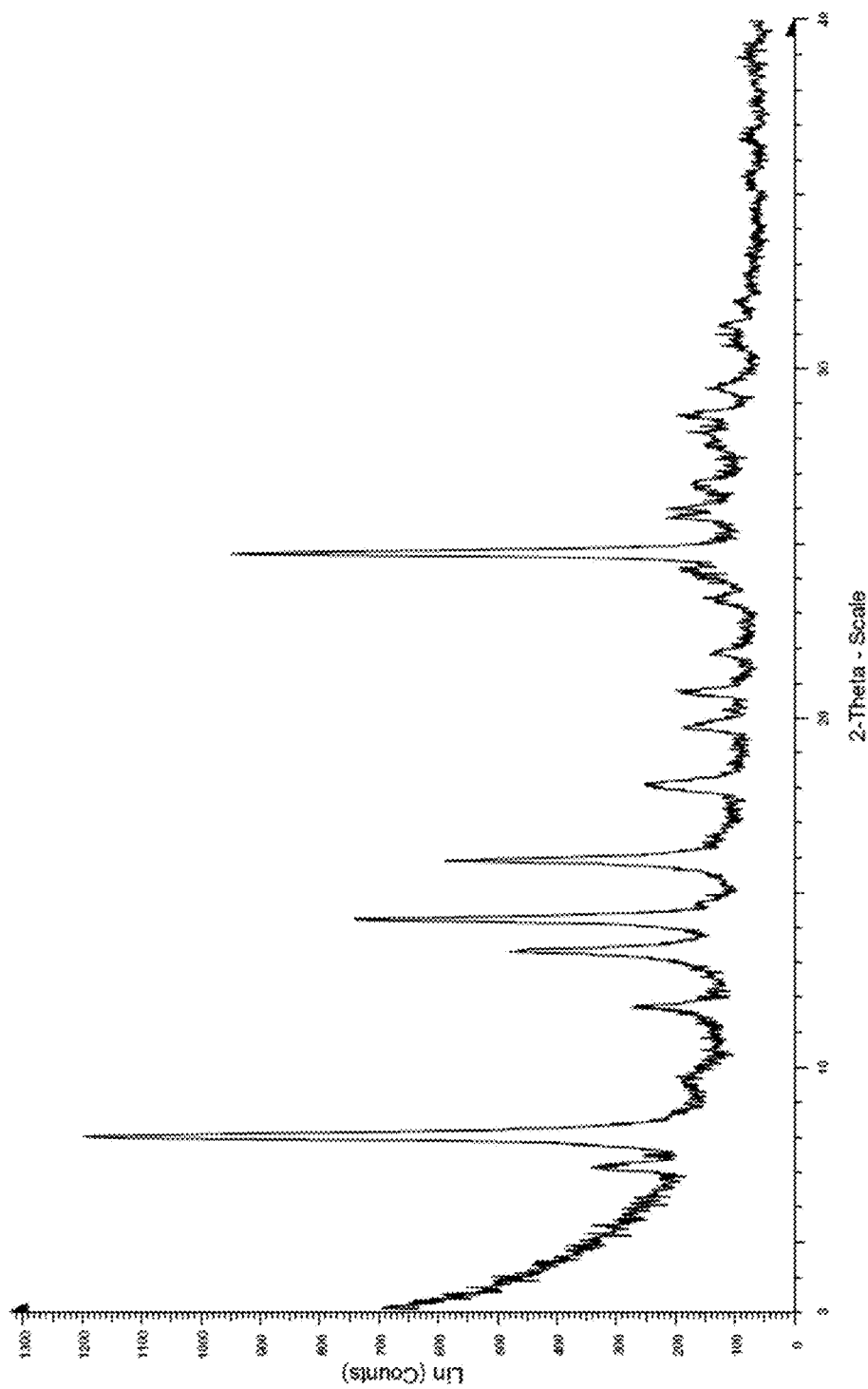
FIG. 14 illustrates a representative XRPD pattern of hydrochloride salt Form VI of Compound (1).
Figure 15:
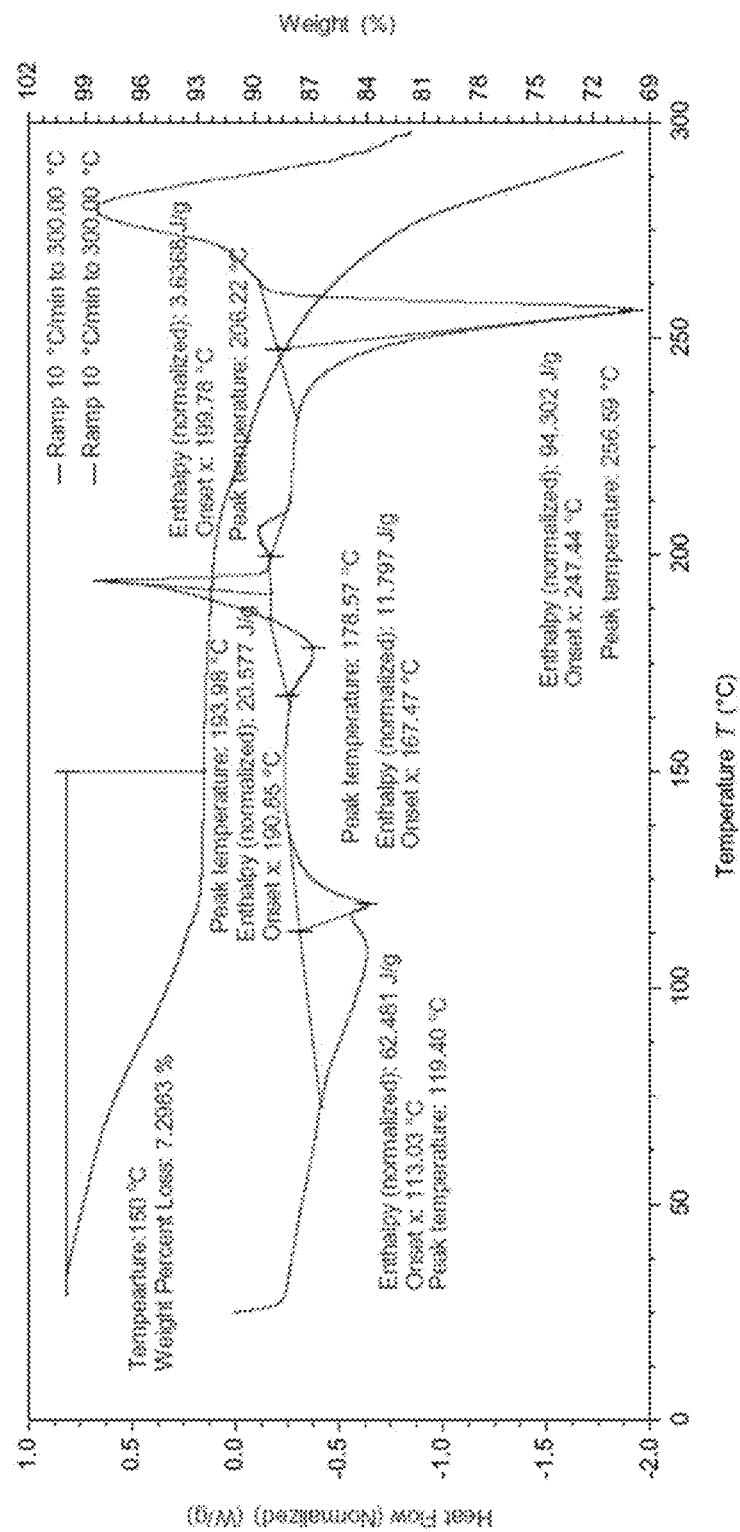
FIG. 15 illustrates representative DSC and TGA profiles of hydrochloride salt Form VI of Compound (1).

FIG. 14 shows a representative XRPD pattern of Form VI. Representative thermal characteristics of Form VI are shown in FIG. 15. The TGA and DSC data further indicate that Form VI is an acetonitrile solvate.

Form VII

Hydrochloride salt Form VII can be obtained from ethanol and/or water. In one embodiment, Form VII can be obtained by evaporating a saturated hydrochloride salt ethanol solution or water solution.

Figure 16:
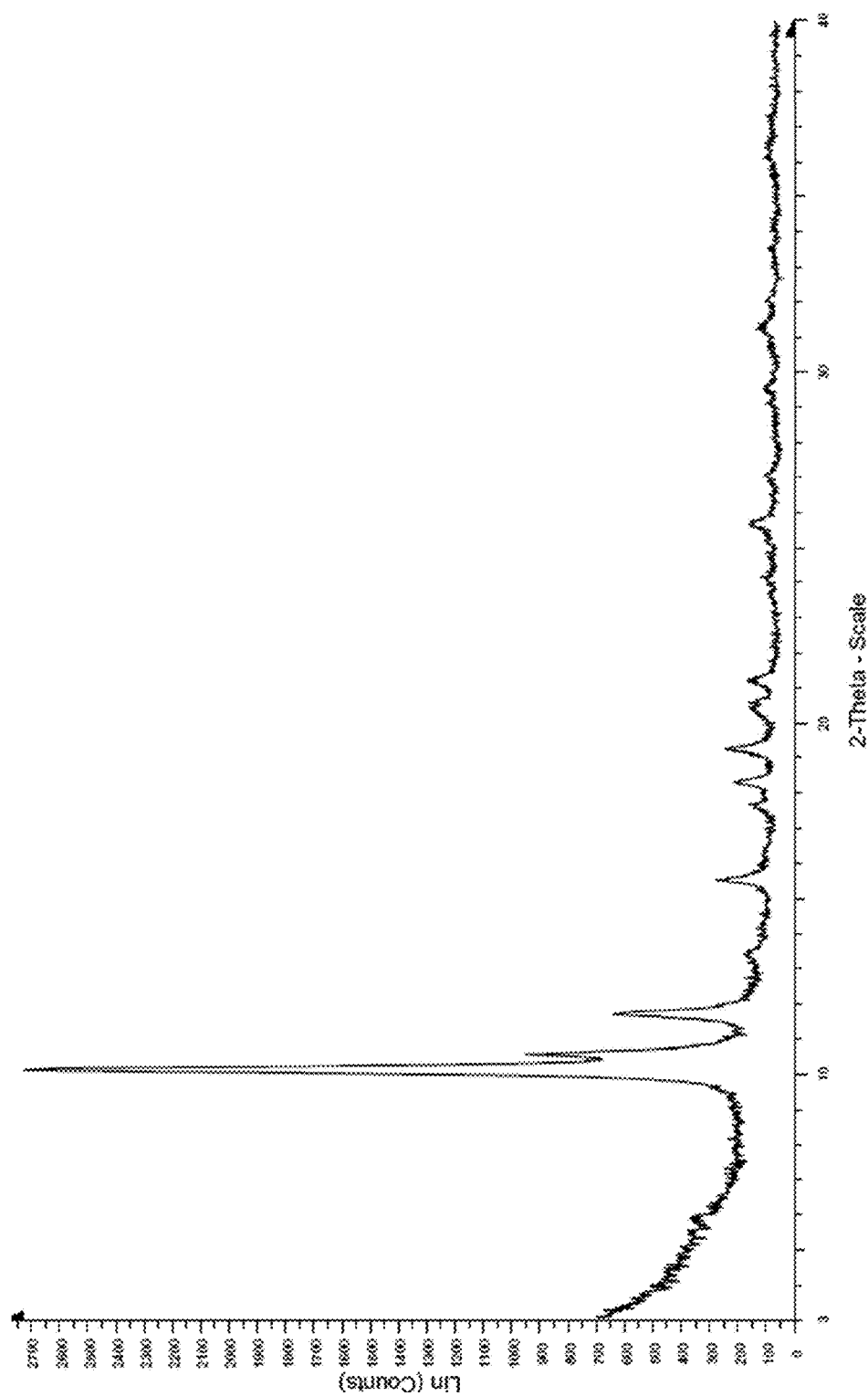
FIG. 16 illustrates a representative XRPD pattern of hydrochloride salt Form VII of Compound (1).
Figure 17:
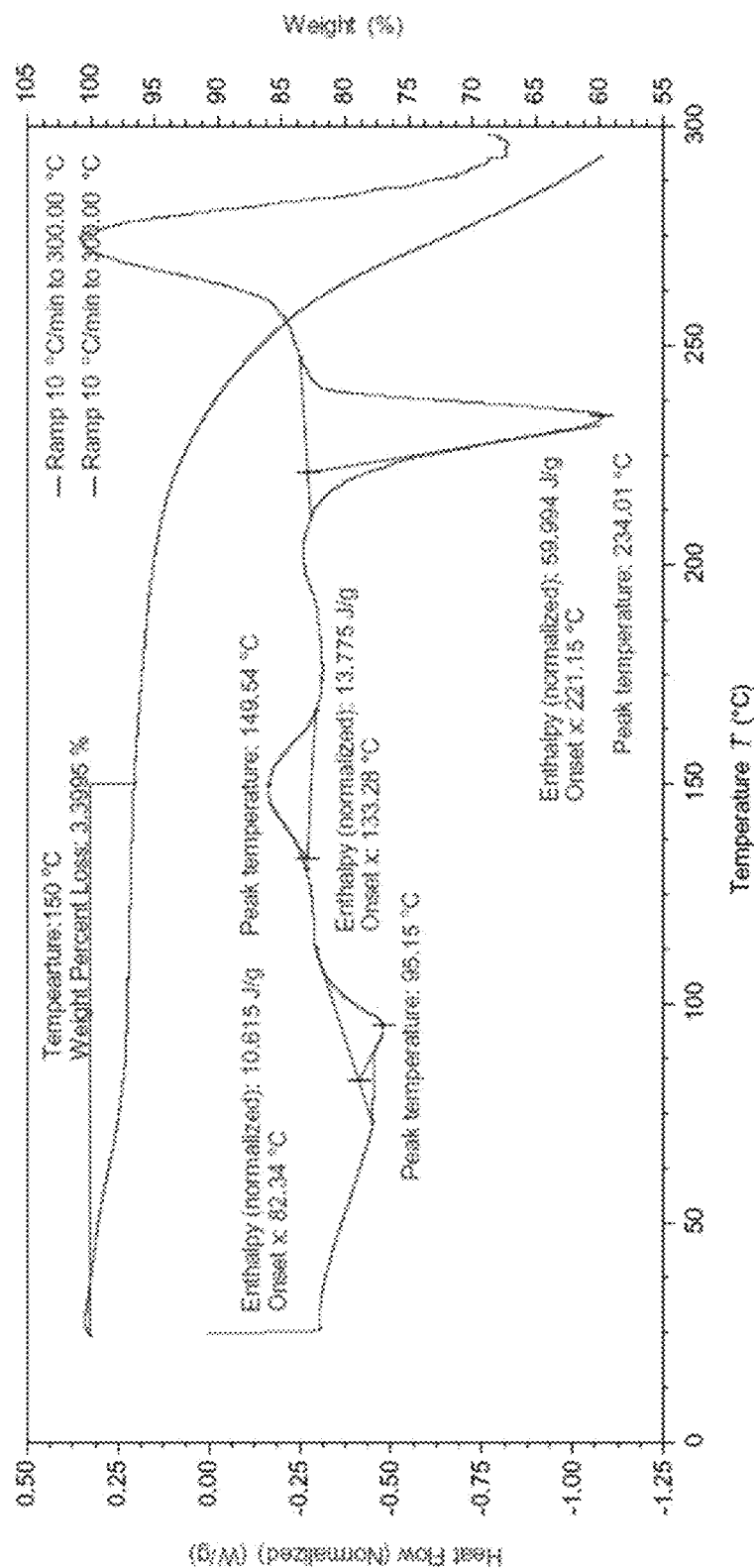
FIG. 17 illustrates representative DSC and TGA profiles of hydrochloride salt Form VII of Compound (1).

FIG. 16 shows a representative XRPD pattern of Form VII. Representative thermal characteristics of Form VI are shown in FIG. 17. The TGA and DSC data further indicate that Form VII is an ethanol solvate or a hydrate. The XRPD patterns of the ethanol solvate and the hydrate are nearly the same, indicating the ethanol solvate and the hydrate of Form VII have similar crystal lattice.

Figure 18:
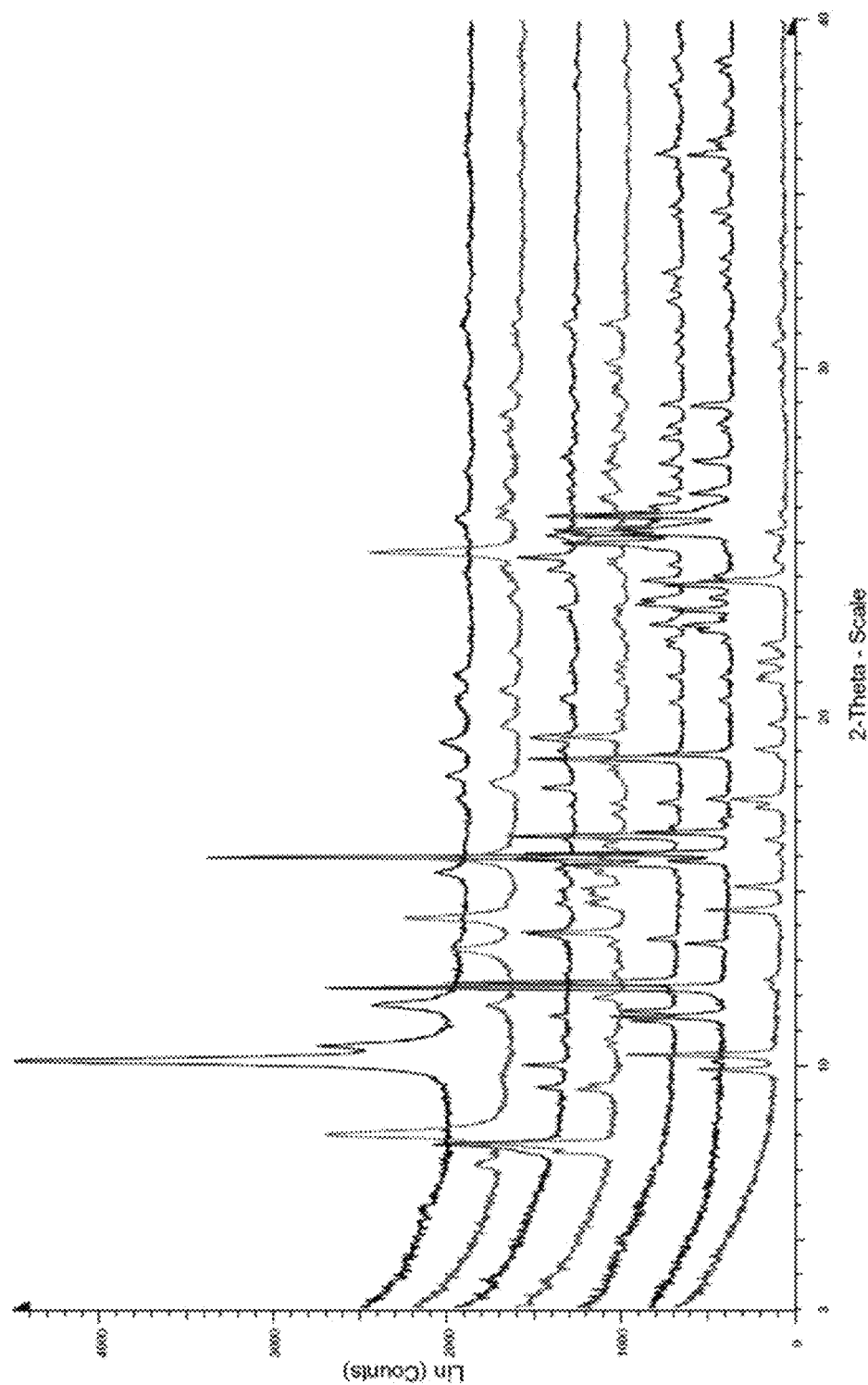
FIG. 18 illustrates a representative XRPD patterns of hydrochloride salt Forms I to VII of Compound (1), from bottom to top, respectively.

FIG. 18 illustrates a comparison of XRPD patterns of Forms I-VII. Table 3 summarizes the DSC and TGA data of Form II-VII of hydrochloride salt.

TABLE 3

DSC and TGA of Form II-VII of Hydrochloride salt.

| Lot | XRPD | DSC | TGA | Comment |
|---|---|---|---|---|
| 32519-054B1 | Form II | 36/61° C.; 12 J/g<br>182/194° C.; 44 J/g<br>242/248° C.; 9 J/g | RT-56° C.: 1.1%<br>56-200° C.:7.1% | MeOH solvate |

TABLE 3-continued

DSC and TGA of Form II-VII of Hydrochloride salt.

| Lot | XRPD | DSC | TGA | Comment |
|---|---|---|---|---|
| 32519-059A1 | Form III | 129/144° C.; 49 J/g<br>167/172° C.; 3 J/g<br>254/261° C.; 94 J/g | RT-180° C.:<br>11.2% | EtOH solvate |
| 32519-059B1 | Form IV | 54/77° C.; 38 J/g<br>102/122° C.; 43 J/g<br>exo: 195/200° C.; 31 J/g<br>250/258° C.; 101 J/g | RT-150° C.: 2.8% | Hydrate |
| 32519-059C1 | Form V | 58/78° C.; 60 J/g<br>98/118° C.; 23 J/g<br>exo: 168/176° C.; 6.2 J/g<br>253/262° C.; 107 J/g | RT-61° C.: 2.1%<br>61-150° C.:1.4% | Hydrate |
| 32519-059D1 | Form VI | 113/119° C.; 62 J/g<br>167/179° C.; 12 J/g<br>exo: 191/194° C.; 21 J/g<br>exo:200/206° C.; 3.6 J/g<br>247/257° C.; 94 J/g | RT-150° C.: 7.3% | ACN solvate |
| 32519-045B2 | Form VII | 82/95° C.; 11 J/g<br>exo: 133/150° C.; 14 J/g<br>221/234° C.; 60 J/g | RT-200° C.: 3.4% | EtOH solvate |

Oxalate Salt of Compound (1)

Oxalate Salt of Compound (1) exhibits two crystalline polymorphs.

Form I

Oxalate salt Form I can be obtained from various solvents, including, but not limited to EtOAc. In one embodiment, 1.07 g free base was reacted with 420 mg oxalic acid in 72 mL EtOAc by stirring overnight, the crystalline solids were filtered and dried at 40° C., under vacuum. Oxalate salt Form I was characterized by $^1$HNMR,)(RFD, PLM, DVS, TGA and DSC.

Figure 19:
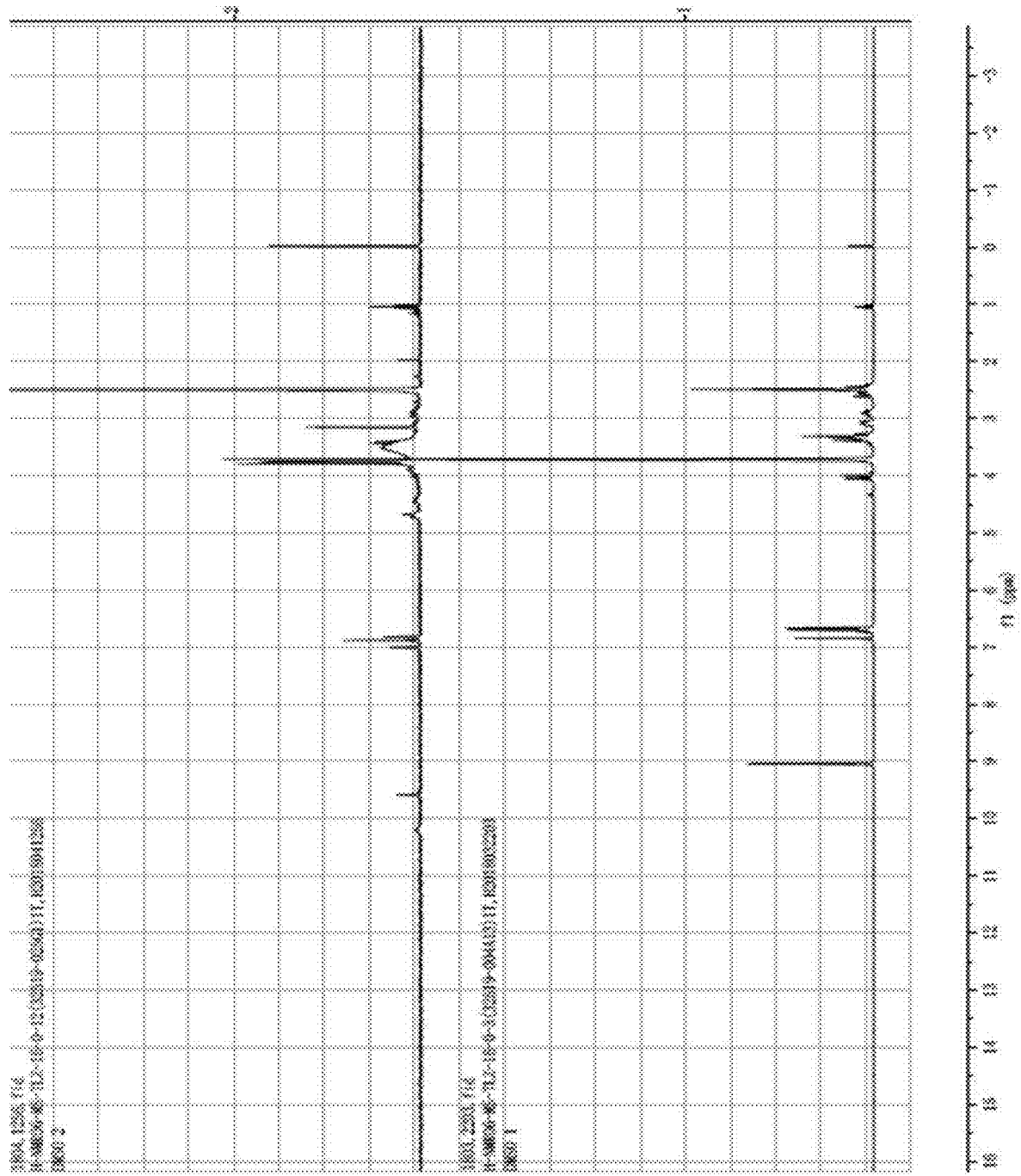
FIG. 19 illustrates a representative $^1$HNMR spectrum of oxalate salt of Compound (1).

FIG. 19 shows a representative $^1$HNMR spectrum of oxalate salt Form I. The $^1$HNMR spectrum shows that there is –0.17 chemical shift occurred near 6.84 ppm, indicating that free base converts into oxalate salt.

Figure 20:
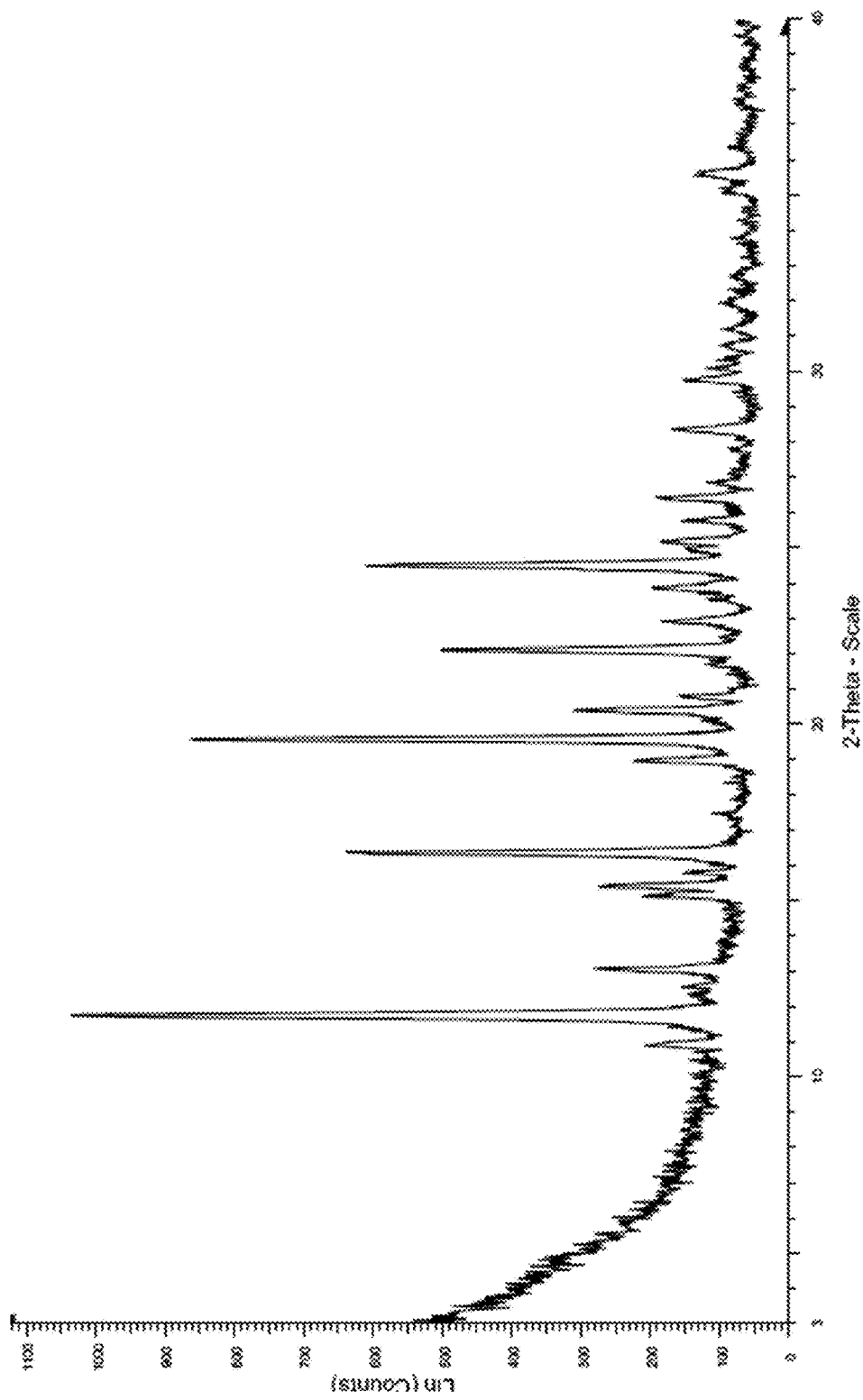
FIG. 20 illustrates a representative XRPD pattern of oxalate salt Form I of Compound (1).

FIG. 20 shows a representative XRPD pattern of oxalate salt Form I. The pattern is characterized by peaks, preferably three or more significant peaks, at approximately 11.7, 13.0, 15.4, 16.3, 19.0, 19.6, 20.4, 22.1, 24.5, and 25.2 degrees 2θ. XRPD pattern illustrates that oxalate salt Form I crystals have good crystallinity. Table 4 lists the XRPD peaks of Form I of oxalate salt.

TABLE 4

List of representative XRPD peaks of oxalate salt Form I

| | Angle<br>2-Theta degree | Intensity %<br>% | d value<br>Angstrom |
|---|---|---|---|
| 1 | 10.886 | 19.9 | 8.12063 |
| 2 | 11.715 | 100 | 7.54772 |
| 3 | 12.311 | 15.5 | 7.1837 |
| 4 | 12.522 | 47 | 7.063 |
| 5 | 13.008 | 26.9 | 6.8002 |
| 6 | 15.129 | 19.3 | 5.85166 |
| 7 | 15.377 | 29.4 | 5.75774 |
| 8 | 15.786 | 12.7 | 5.60954 |
| 9 | 16.336 | 61.3 | 5.42178 |
| 10 | 17.469 | 12.8 | 5.07268 |
| 11 | 18.969 | 21.4 | 4.67461 |
| 12 | 19.568 | 83.3 | 4.53297 |
| 13 | 20.385 | 29.8 | 4.3531 |
| 14 | 20.788 | 14.7 | 4.26951 |
| 15 | 21.709 | 11.3 | 4.09055 |
| 16 | 22.107 | 48.2 | 4.0178 |
| 17 | 22.921 | 17.5 | 3.87688 |
| 18 | 23.549 | 10.8 | 3.7749 |
| 19 | 23.888 | 18.7 | 3.72209 |
| 20 | 24.518 | 58.7 | 3.62775 |
| 21 | 24.954 | 20 | 3.56538 |
| 22 | 25.196 | 31.9 | 3.53176 |
| 23 | 25.798 | 14.7 | 3.45065 |
| 24 | 26.419 | 17.6 | 3.37092 |
| 25 | 26.853 | 11.2 | 3.31737 |
| 26 | 27.795 | 7.6 | 3.20709 |
| 27 | 28.381 | 16 | 3.14222 |
| 28 | 29.767 | 14.5 | 2.99893 |
| 29 | 30.116 | 11.2 | 2.96499 |
| 30 | 30.758 | 9.3 | 2.90456 |
| 31 | 31.233 | 9.1 | 2.86148 |
| 32 | 31.981 | 9.5 | 2.79624 |
| 33 | 35.162 | 8 | 2.55022 |
| 34 | 35.657 | 11.8 | 2.51596 |
| 35 | 37.703 | 6.7 | 2.38395 |
| 36 | 38.1 | 6.7 | 2.36003 |

Figure 21:
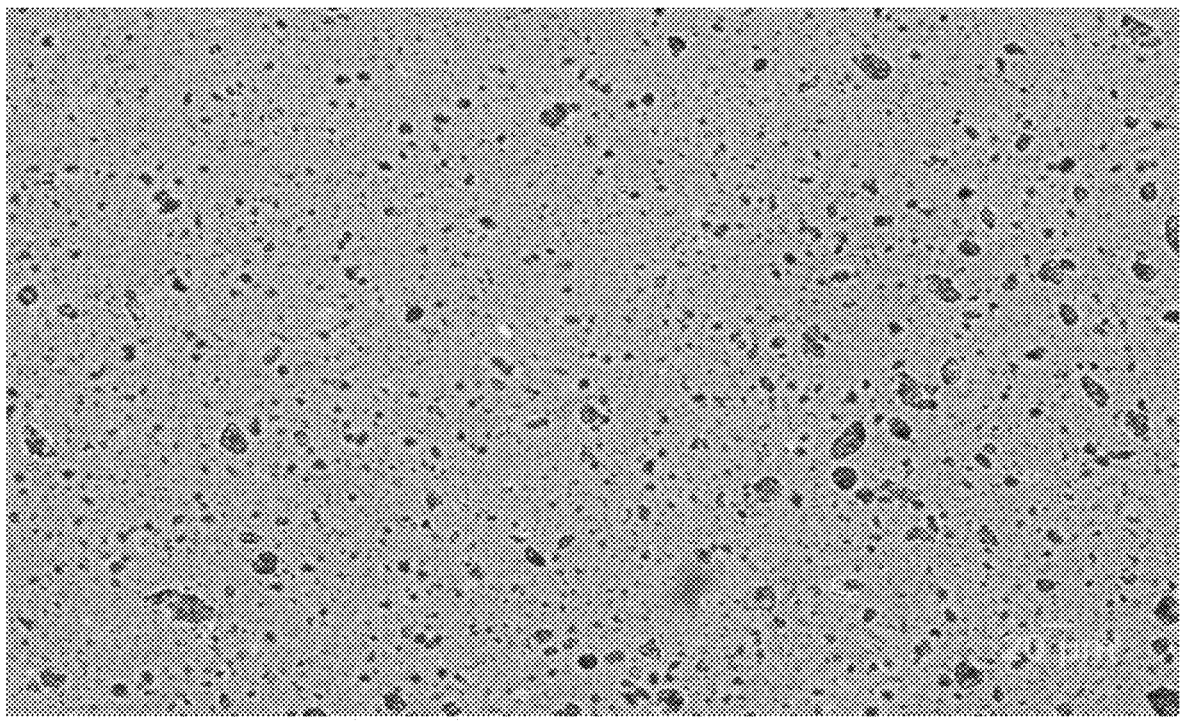
FIG. 21 illustrates a representative PLM image of oxalate salt Form I of Compound (1).

Representative PLM image are shown in FIG. 21.

Figure 22:
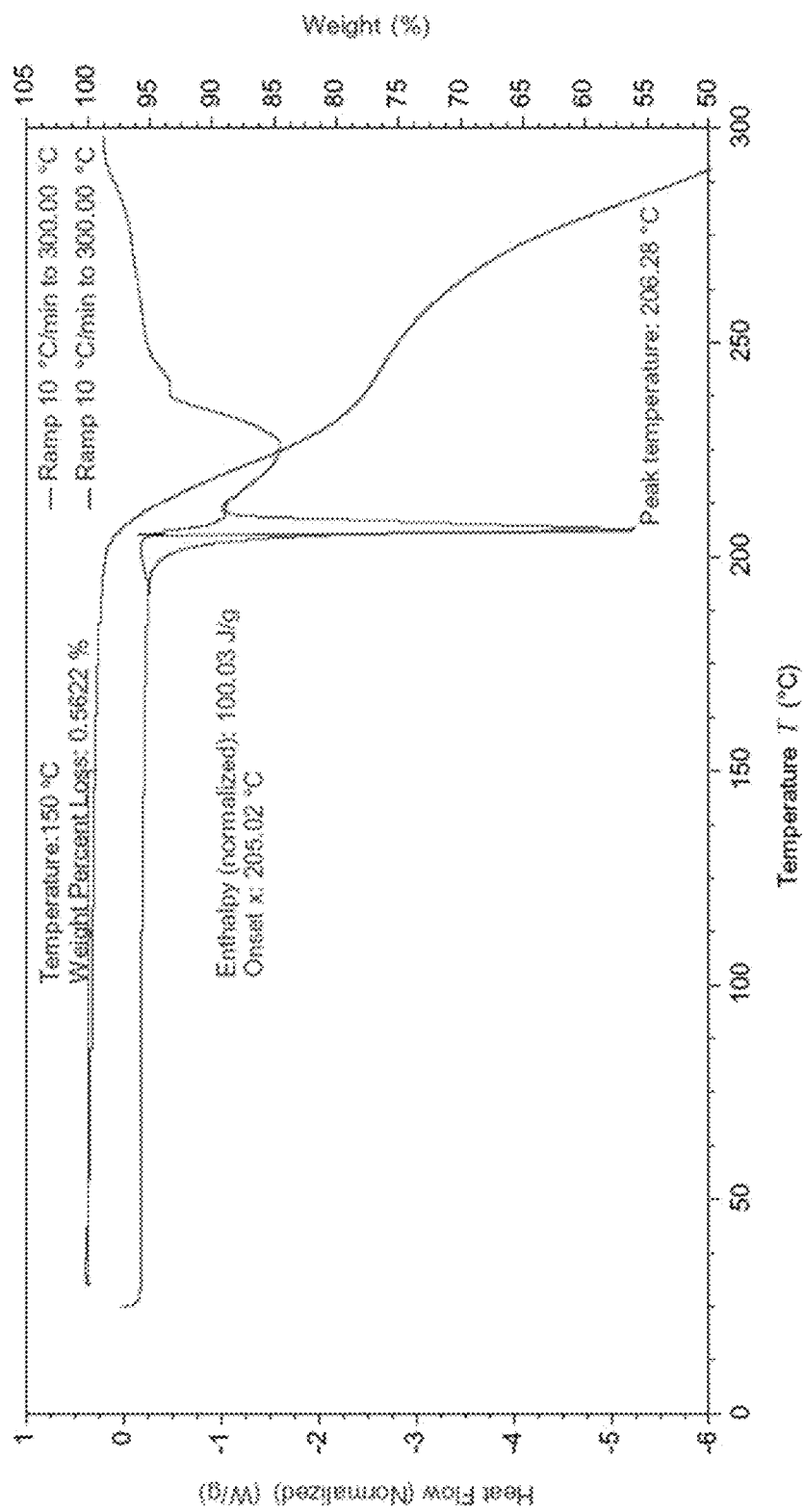
FIG. 22 illustrates representative DSC and TGA profiles of oxalate salt Form I of Compound (1).

Representative thermal characteristics of oxalate salt Form I are shown in FIG. 22. TGA data indicates that there is –0.56% weight loss between RT and 150° C., and the residual solvent is low. DSC data illustrates that Form I has one endothermic peak with the onset and peak temperatures of 205 and 206° C. respectively, and the enthalpy of the endothermic peak is about 100 J/g.

Figure 23:
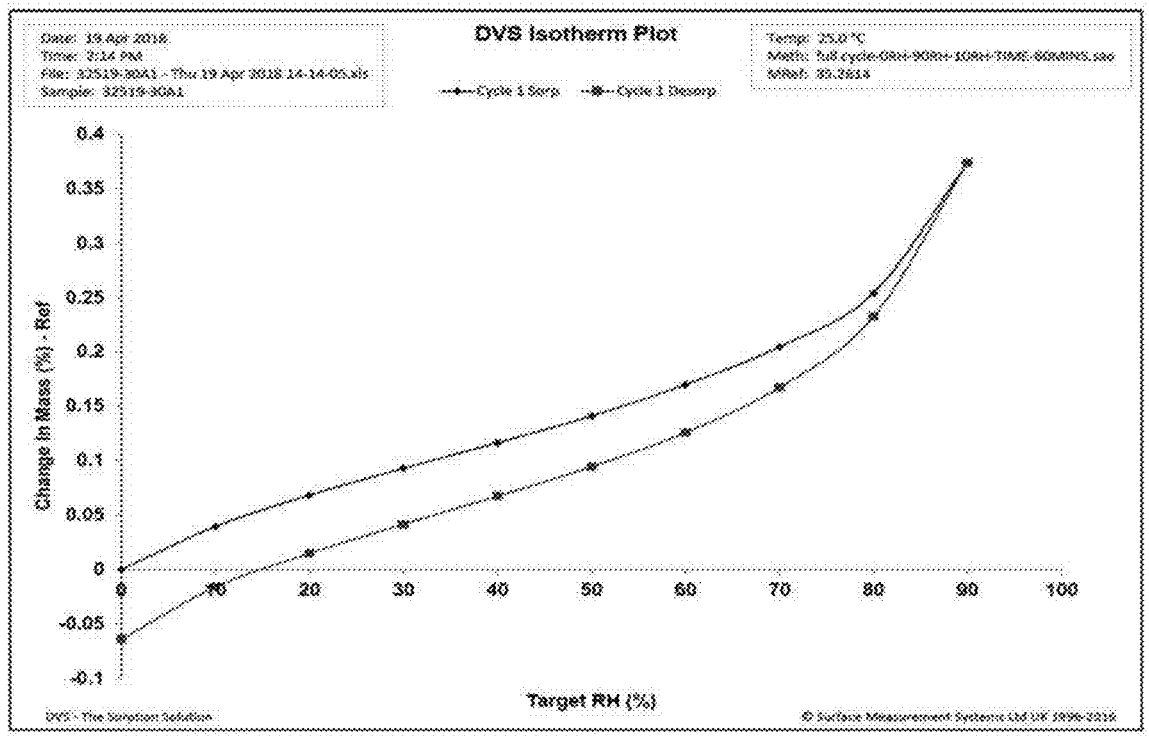
FIG. 23 illustrates representative DVS profiles of oxalate salt Form I of Compound (1).
Figure 23:
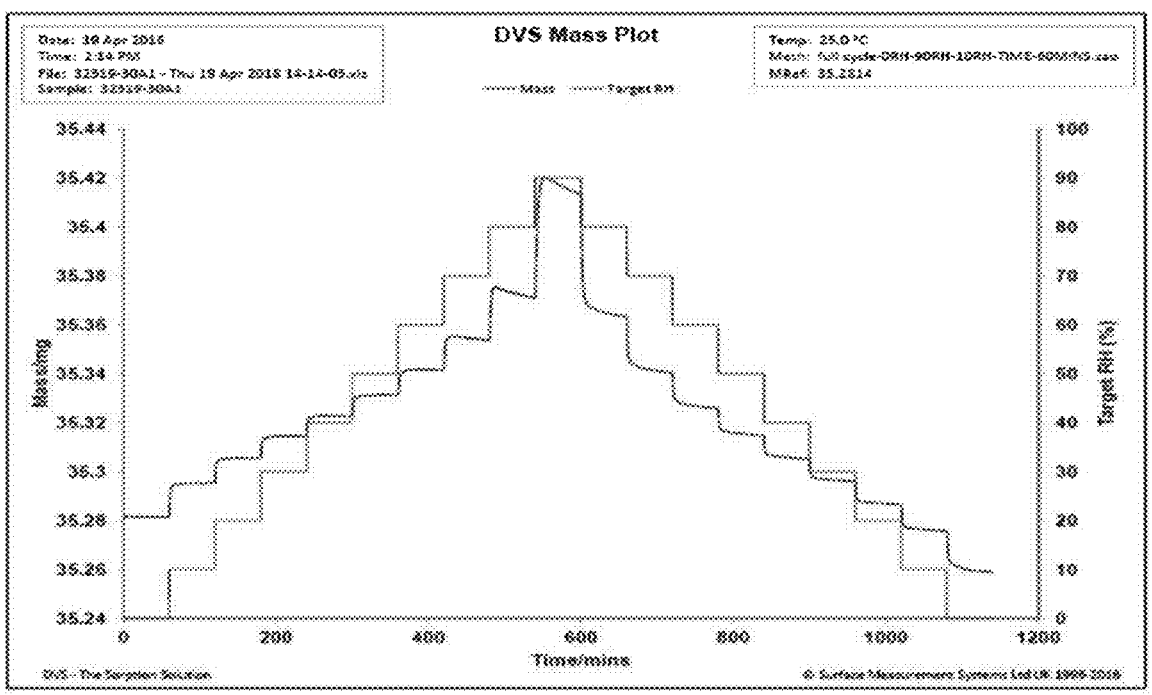

Representative DVS data are plotted in FIG. 23, which suggest that Form I of oxalate salt is slightly hygroscopic, and absorb about 0.25 wt % at 80% RH. The solid form does not change after DVS test.

Solubility studies of Form I oxalate salt in water (in 2 hours) were higher than that of the free base, which were improved from free base solubility of less than 1 mg/mL to the Form I oxalate salt solubility of approximately 19.2 mg/mL.

Form II

Oxalate salt Form II can be obtained from methanol. In one embodiment, Form II can be obtained by stirring a oxalate salt Form I slurry in methanol at RT for 3 days, and/or stirring the slurry at 50° C. for one day. In another embodiment, oxalate salt Form II can be obtained by adding an anti-solvent, e.g. MTBE, Toluene, EtOAc, or IPA, into a methanol solution.

Figure 24:
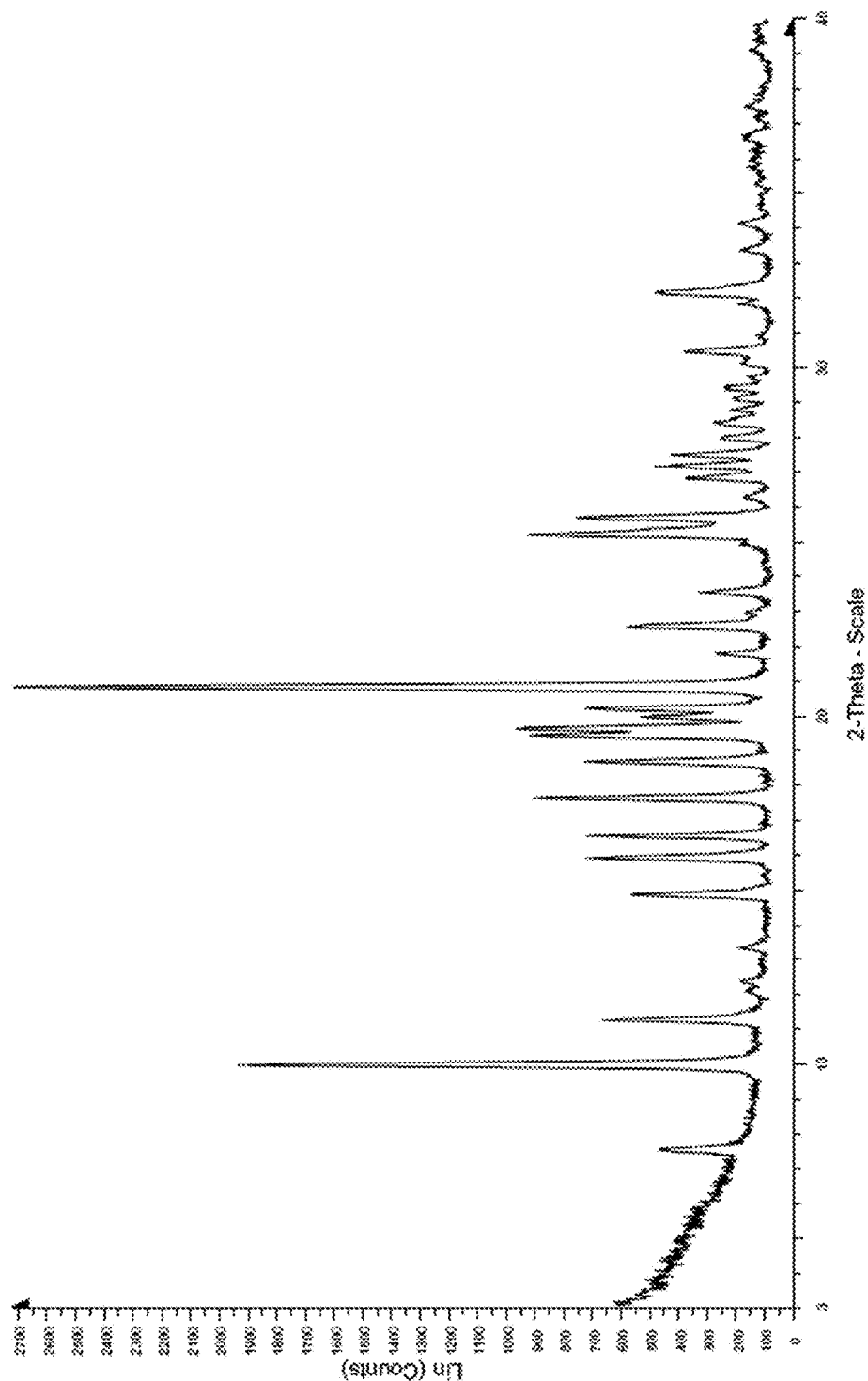
FIG. 24 illustrates a representative XRPD pattern of oxalate salt Form II of Compound (1).
Figure 25:
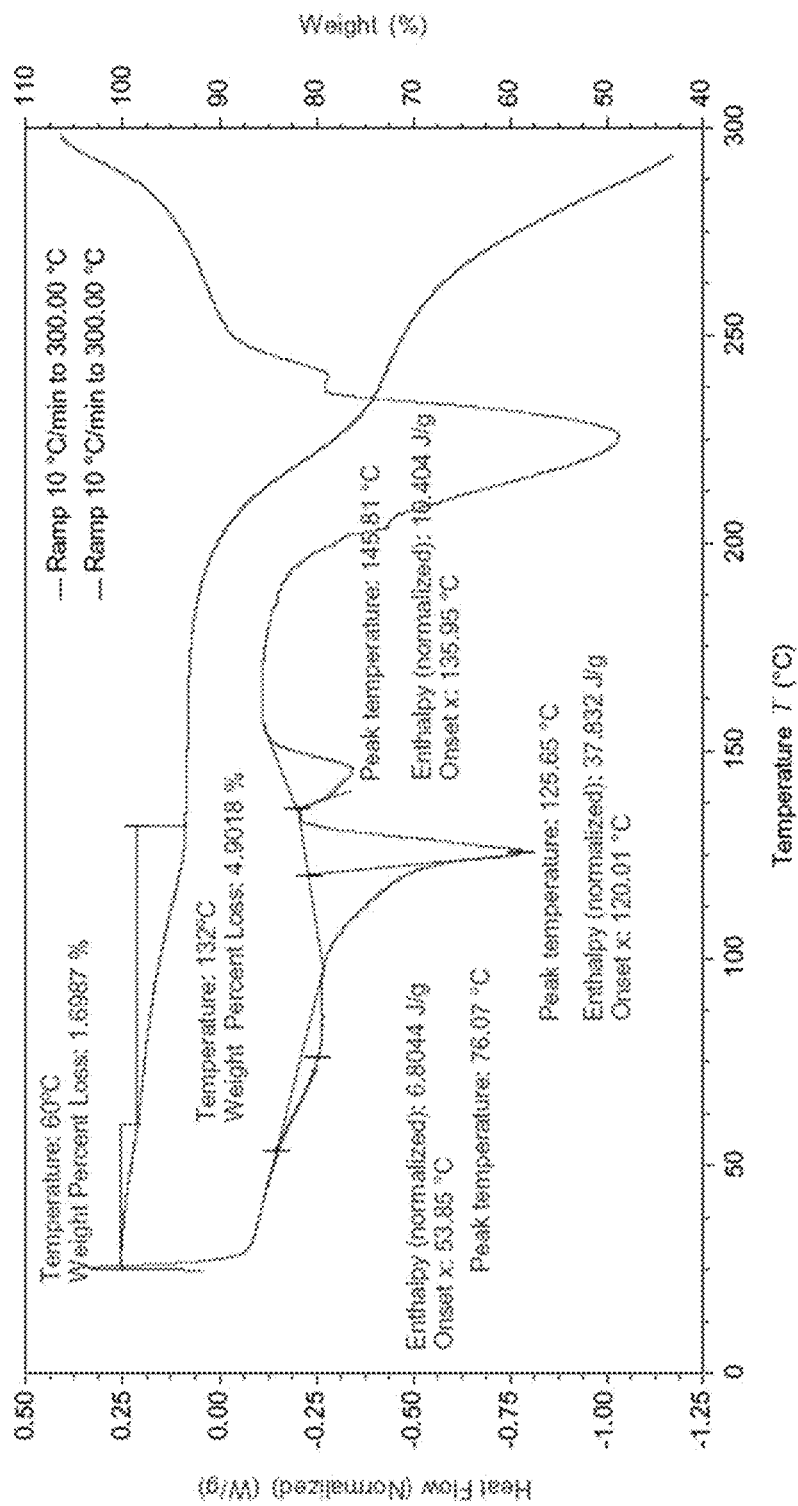
FIG. 25 illustrates representative DSC and TGA profiles of oxalate salt Form II of Compound (1).

FIG. 24 shows a representative XRPD pattern of Form II. Representative thermal characteristics of Form II are shown in FIG. 25. The TGA and DSC data further indicate that oxalate salt Form II is a methanol solvate.

Maleate Salt of Compound (1)

Maleate Salt

Maleate salt can be obtained from various solvents, including, but not limited to EtOAc and MeOH. In one embodiment, 1.03 g free base was reacted with 356 mg maleic acid in 72 mL EtOAc by stirring overnight, the crystalline solids were filtered and dried at 40° C., under vacuum. Maleate salt was characterized by $^1$HNMR, XRPD, PLM, DVS, TGA and DSC.

Figure 26:
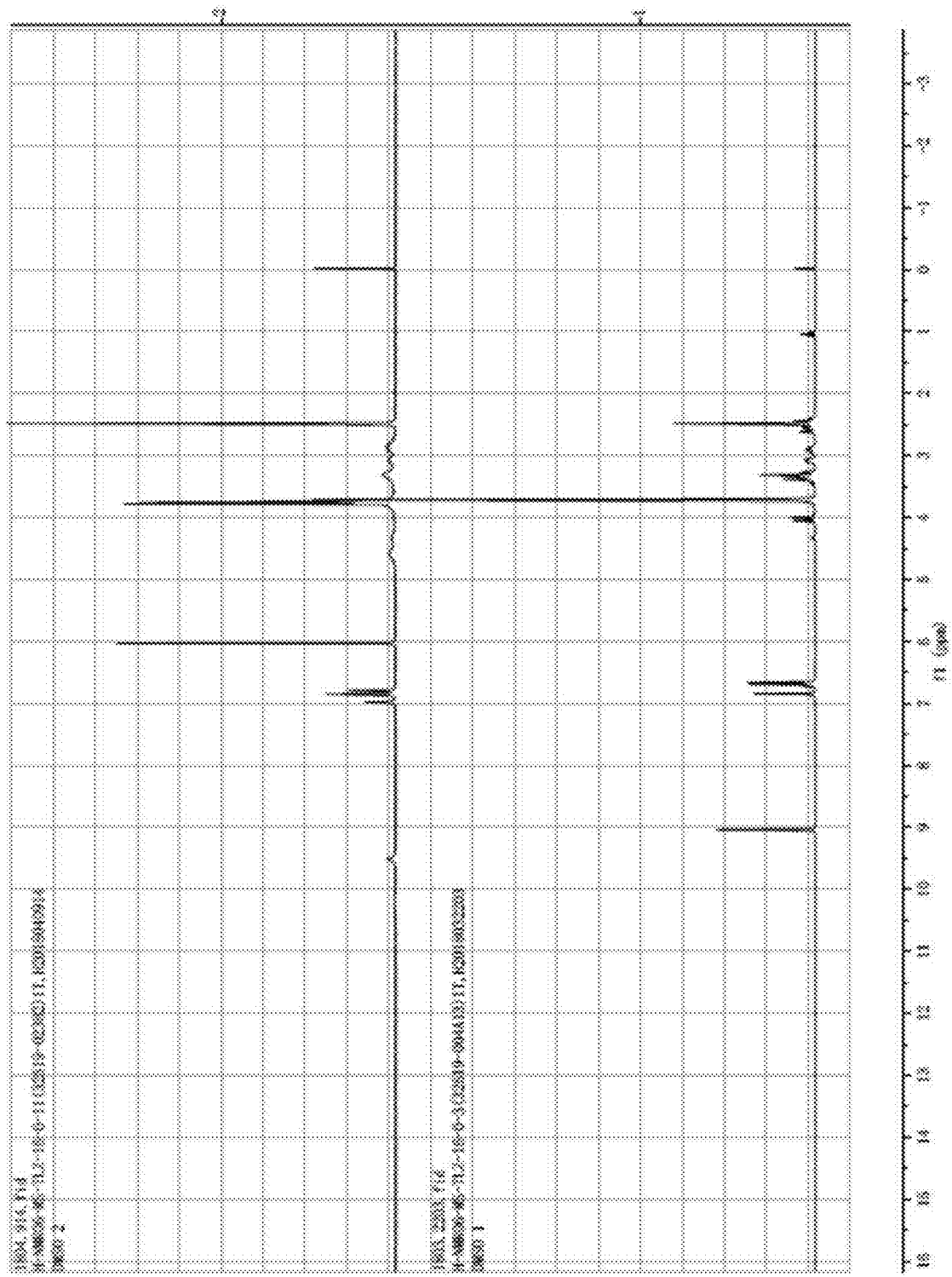
FIG. 26 illustrates a representative $^1$HNMR spectrum of maleate salt of Compound (1).

FIG. 26 shows a representative $^1$HNMR spectrum of maleate salt. The $^1$HNMR spectrum shows that that maleic acid formed maleate with free base in a molar ratio of 1:1.

Figure 27:
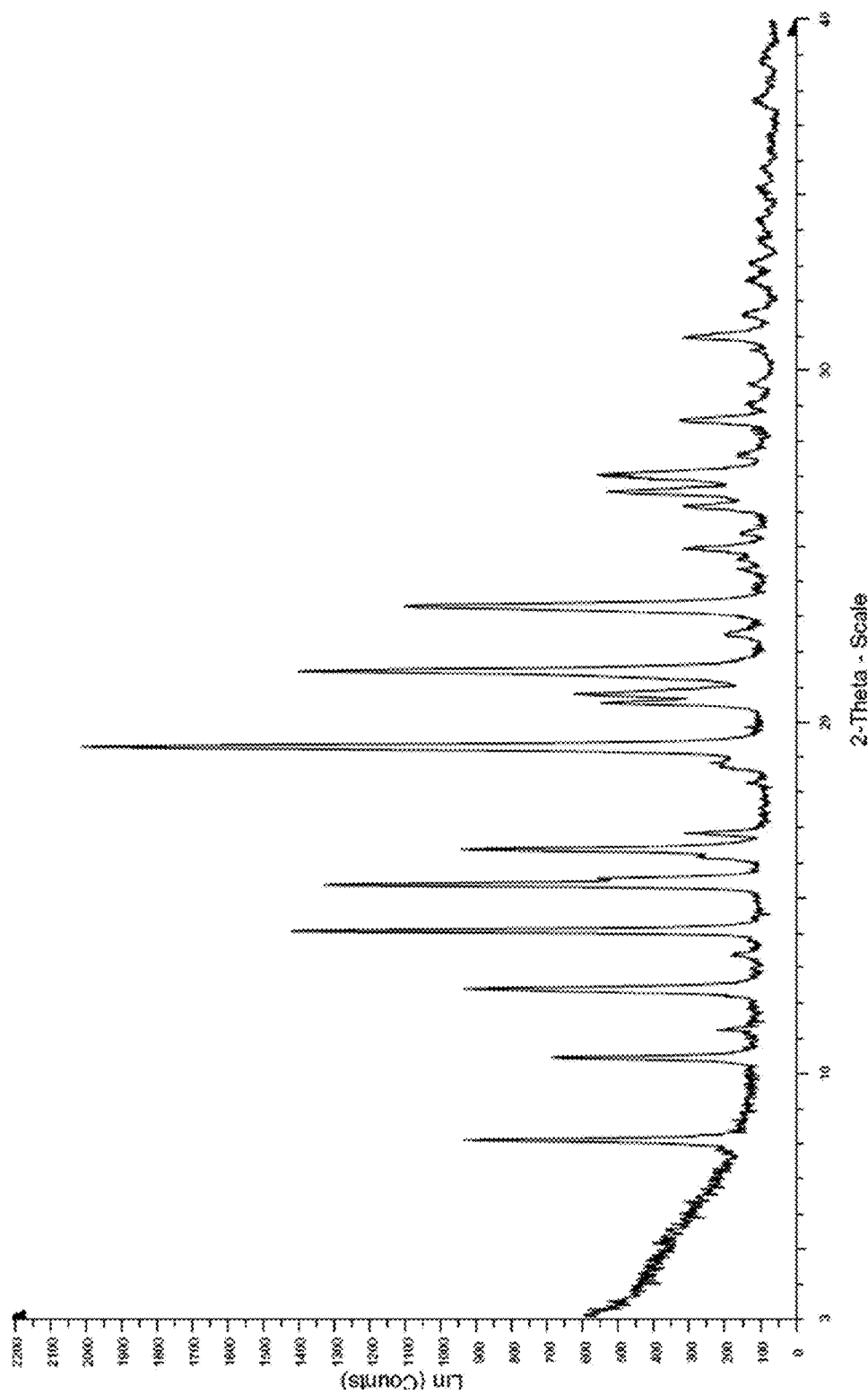
FIG. 27 illustrates a representative XRPD pattern of maleate salt of Compound (1).

FIG. 27 shows a representative XRPD pattern of maleate salt. The pattern is characterized by peaks, preferably three or more significant peaks, at approximately 8.0, 10.4, 12.4, 14.0, 15.3, 16.4, 19.3, 20.8, 21.5, and 23.3 degrees 2θ.

XRPD pattern illustrates that maleate salt crystals have good crystallinity. Table 5 lists the XRPD peaks of maleate salt.

TABLE 5

List of representative XRPD peaks of maleate salt

| | Angle 2-Theta degree | Intensity % | d value Angstrom |
|---|---|---|---|
| 1 | 8.029 | 46.3 | 11.0025 |
| 2 | 10.392 | 33.9 | 8.50589 |
| 3 | 11.223 | 10.6 | 7.87745 |
| 4 | 12.362 | 46.3 | 7.1544 |
| 5 | 13.372 | 8.3 | 6.61605 |
| 6 | 14.032 | 70.6 | 6.30655 |
| 7 | 15.347 | 65.9 | 5.76892 |
| 8 | 16.168 | 13.9 | 5.47786 |
| 9 | 16.367 | 46.7 | 5.41155 |
| 10 | 16.823 | 15.4 | 5.2658 |
| 11 | 18.266 | 6.6 | 4.85293 |
| 12 | 18.794 | 10.2 | 4.71788 |
| 13 | 19.293 | 100 | 4.59699 |
| 14 | 20.557 | 27 | 4.31692 |
| 15 | 20.832 | 34.3 | 4.2607 |
| 16 | 21.471 | 69.5 | 4.13526 |
| 17 | 22.509 | 9.7 | 3.94683 |
| 18 | 23.32 | 54.8 | 3.81148 |
| 19 | 24.35 | 7.9 | 3.6525 |
| 20 | 24.934 | 15.6 | 3.56819 |
| 21 | 25.381 | 7.4 | 3.50642 |
| 22 | 26.159 | 15.5 | 3.40378 |
| 23 | 26.574 | 26.2 | 3.35157 |
| 24 | 27.037 | 27.5 | 3.29528 |
| 25 | 27.606 | 7.9 | 3.22861 |
| 26 | 28.627 | 16 | 3.11574 |
| 27 | 29.065 | 6.7 | 3.06977 |
| 28 | 29.636 | 6.1 | 3.01191 |
| 29 | 31.017 | 14.7 | 2.88089 |
| 30 | 31.638 | 7.2 | 2.82579 |
| 31 | 32.607 | 6.7 | 2.74392 |
| 32 | 33.121 | 6.2 | 2.70256 |
| 33 | 33.745 | 4.9 | 2.65397 |
| 34 | 34.323 | 5.3 | 2.61061 |
| 35 | 35.065 | 4.2 | 2.55706 |
| 36 | 35.242 | 5.2 | 2.54461 |
| 37 | 35.819 | 4.9 | 2.50489 |
| 38 | 37.778 | 5.7 | 2.37939 |
| 39 | 38.867 | 4.6 | 2.31521 |

Figure 28:
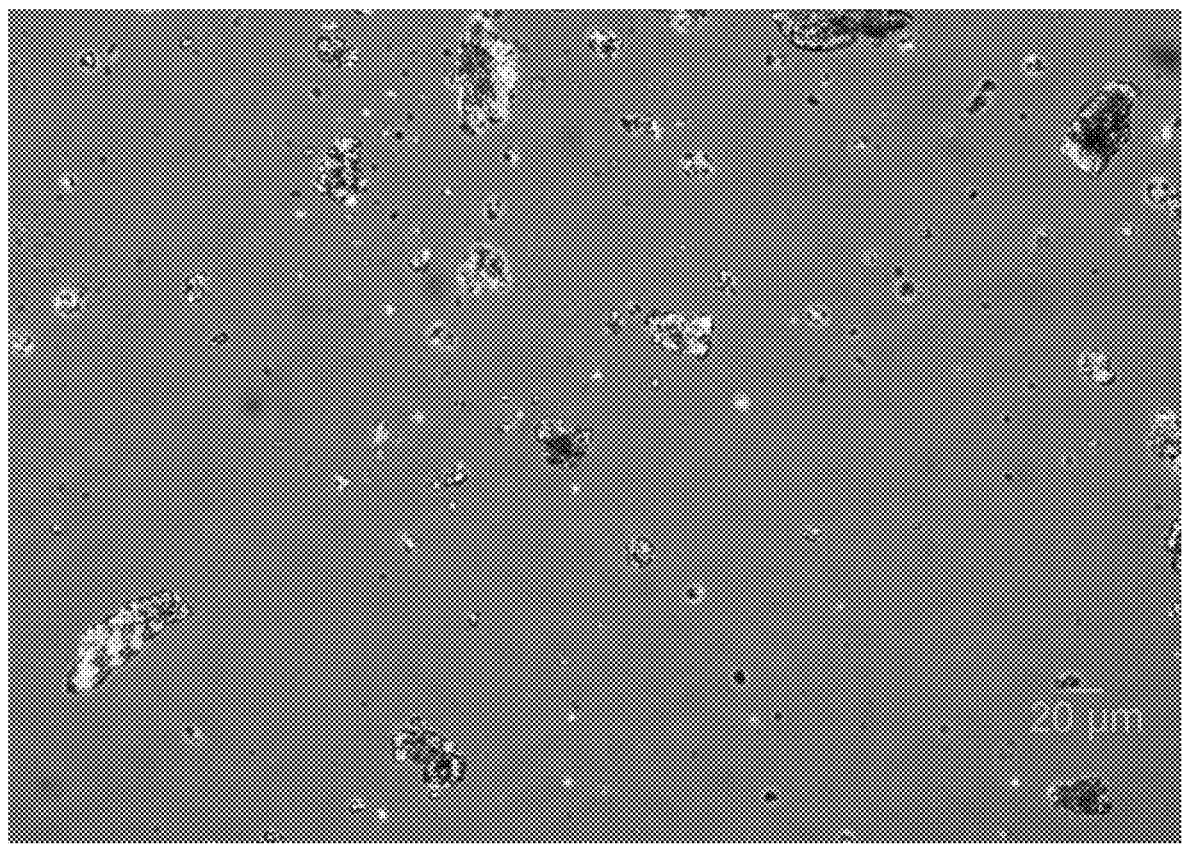
FIG. 28 illustrates a representative PLM image of maleate salt Compound (1).

Representative PLM image is shown in FIG. 28.

Figure 29:
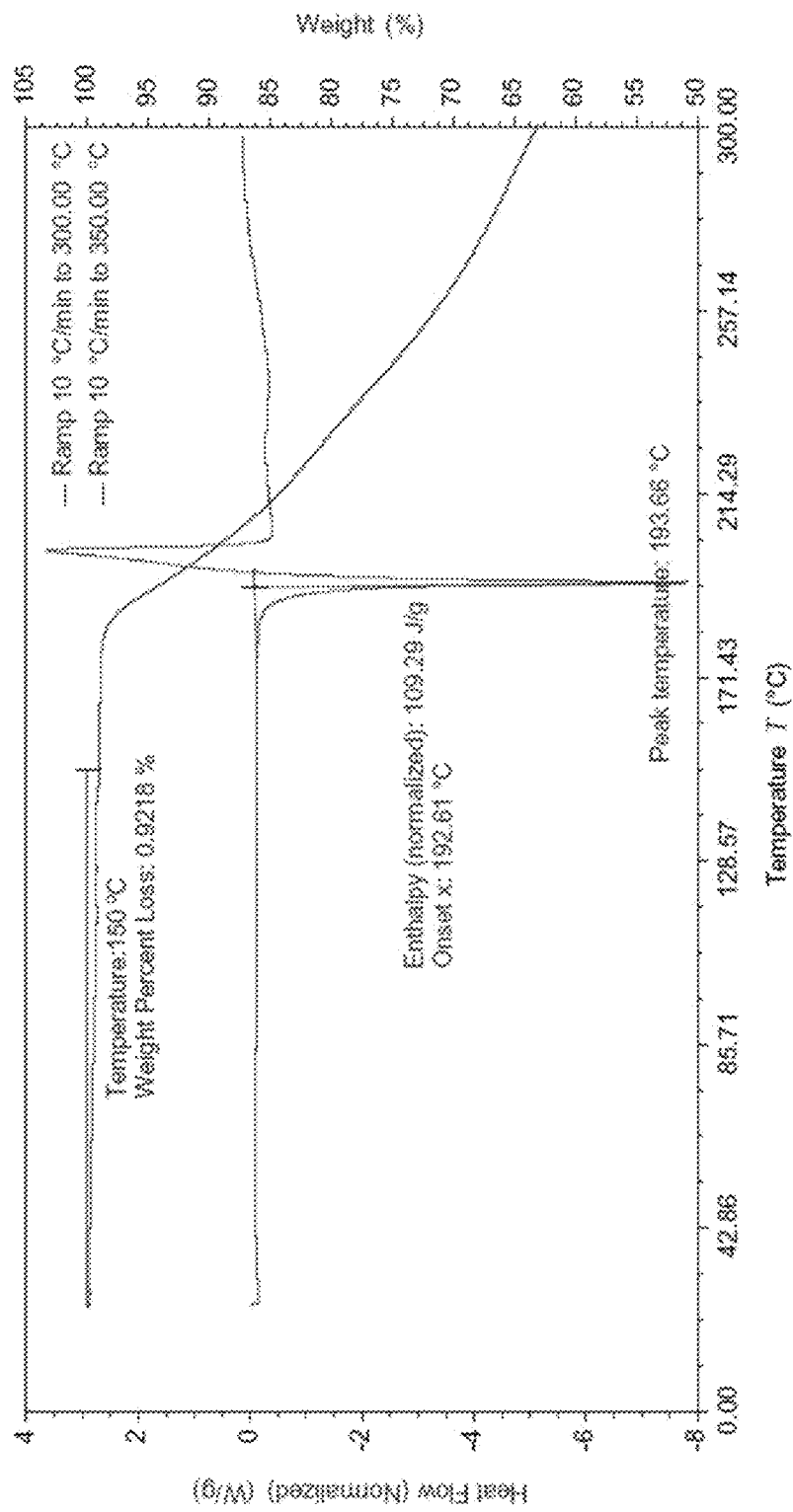
FIG. 29 illustrates representative DSC and TGA profiles of maleate salt of Compound (1).

Representative thermal characteristics of maleate salt are shown in FIG. 29. TGA data indicates that there is −0.92% weight loss between RT and 150° C., which is due to the loss of the residue solvent. DSC data illustrates that has one endothermic peak with the onset and peak temperatures of 193 and 197° C. respectively, and the enthalpy of the endothermic peak is about 104 J/g.

Figure 30:
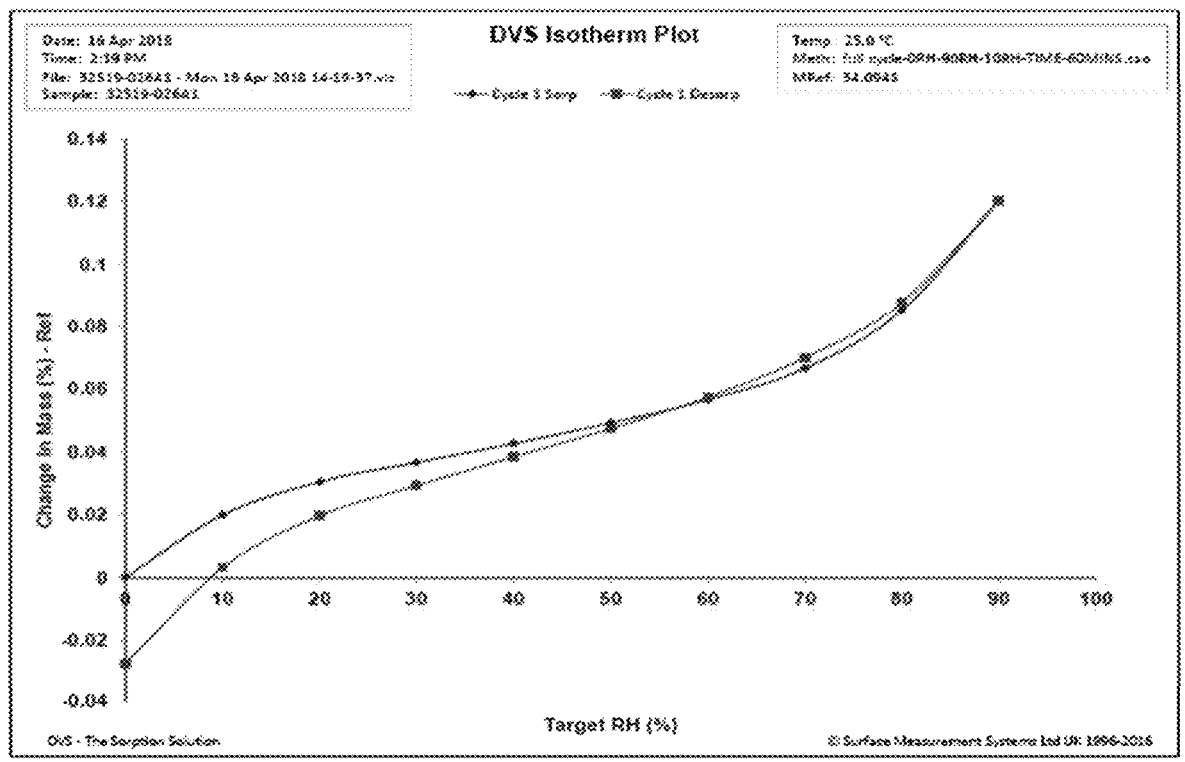
FIG. 30 illustrates representative DVS profiles of maleate salt of Compound (1).
Figure 30:
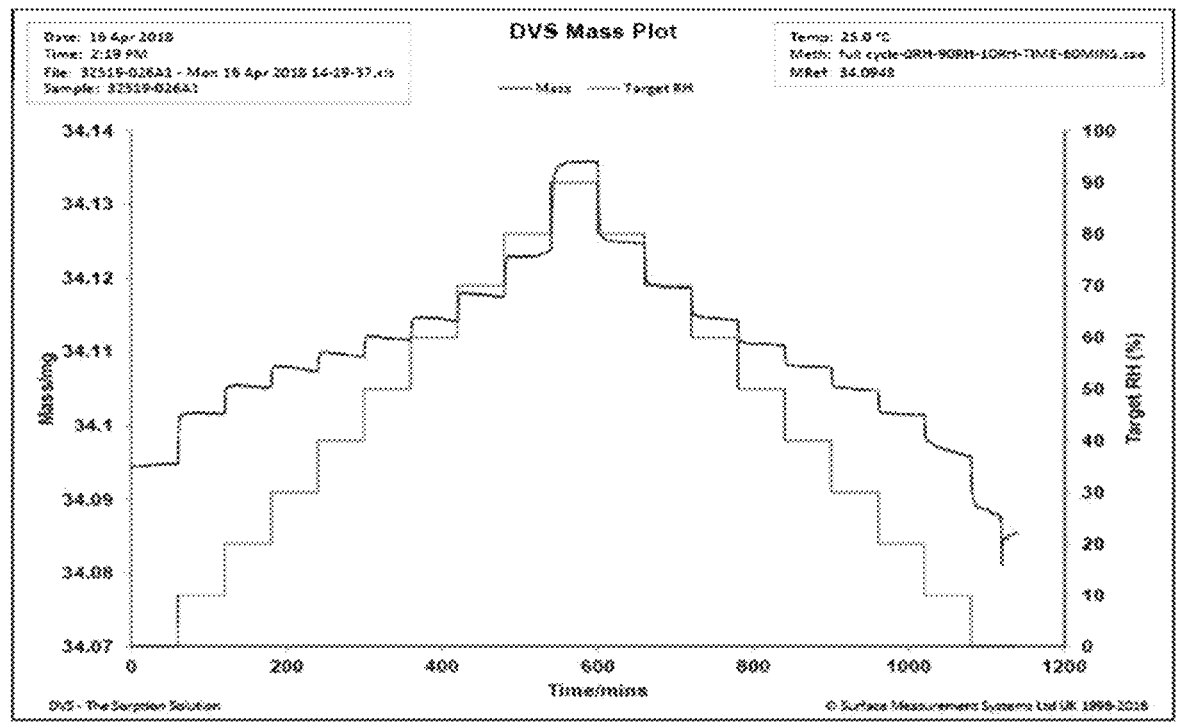

Representative DVS data are plotted in FIG. 30, which suggest that of maleate salt is slightly hygroscopic, and absorb about 0.085 wt % at 80% RH. The solid form does not change after DVS test.

Solubility studies of maleate salt in water (in 2 hours) is higher than that of the free base, which is improved from free base solubility of less than 1 mg/mL to the maleate salt solubility of approximately 11.0 mg/mL.

Sulfate, Mesylate, and Benzene sulfonate Salts of Compound (1)

Sulfate Salt

Sulfate salt can be obtained from various solvents, including, but not limited to EtOAc and Acetone. In one embodiment, 1 mL EtOAc solution of free base (15 mg/mL) was added into 500 µL EtOAc solution of $H_2SO_4$ (0.07 mol/L), crystalline solids were obtained by stirring overnight, the crystalline solids were filtered and dried at 40° C., under vacuum. Sulfate salt was characterized by $^1$HNMR, PLM, TGA and DSC.

Mesylate Salt

Mesylate salt can be obtained from various solvents, including, but not limited to EtOAc and Acetone. In one embodiment, 2.6 µL (1 eq) methanesulfonic acid was added into 1 mL EtOAc solution of free base (15 mg/mL), crystalline solids were obtained by stirring overnight, the crystalline solids were filtered and dried at 40° C., under vacuum. Mesylate salt was characterized by $^1$HNMR, XRPD, PLM, TGA and DSC.

Benzene Sulfonate Salt

Benzene sulfonate salt can be obtained from various solvents, including, but not limited to EtOAc and Acetone. In one embodiment, 7.6 mg (1 eq) Benzenesulfonic acid was added into 1 mL EtOAc solution of free base (15 mg/mL), crystalline solids were obtained by stirring overnight, the crystalline solids were filtered and dried at 40° C., under vacuum. Benzene sulfonate salt was characterized by $^1$HNMR, XRPD, PLM, TGA and DSC. XRPD pattern illustrates that sulfate and mesylate crystals have good crystallinity, and benzene sulfonate salt has poor crystallinity.

Figure 31:
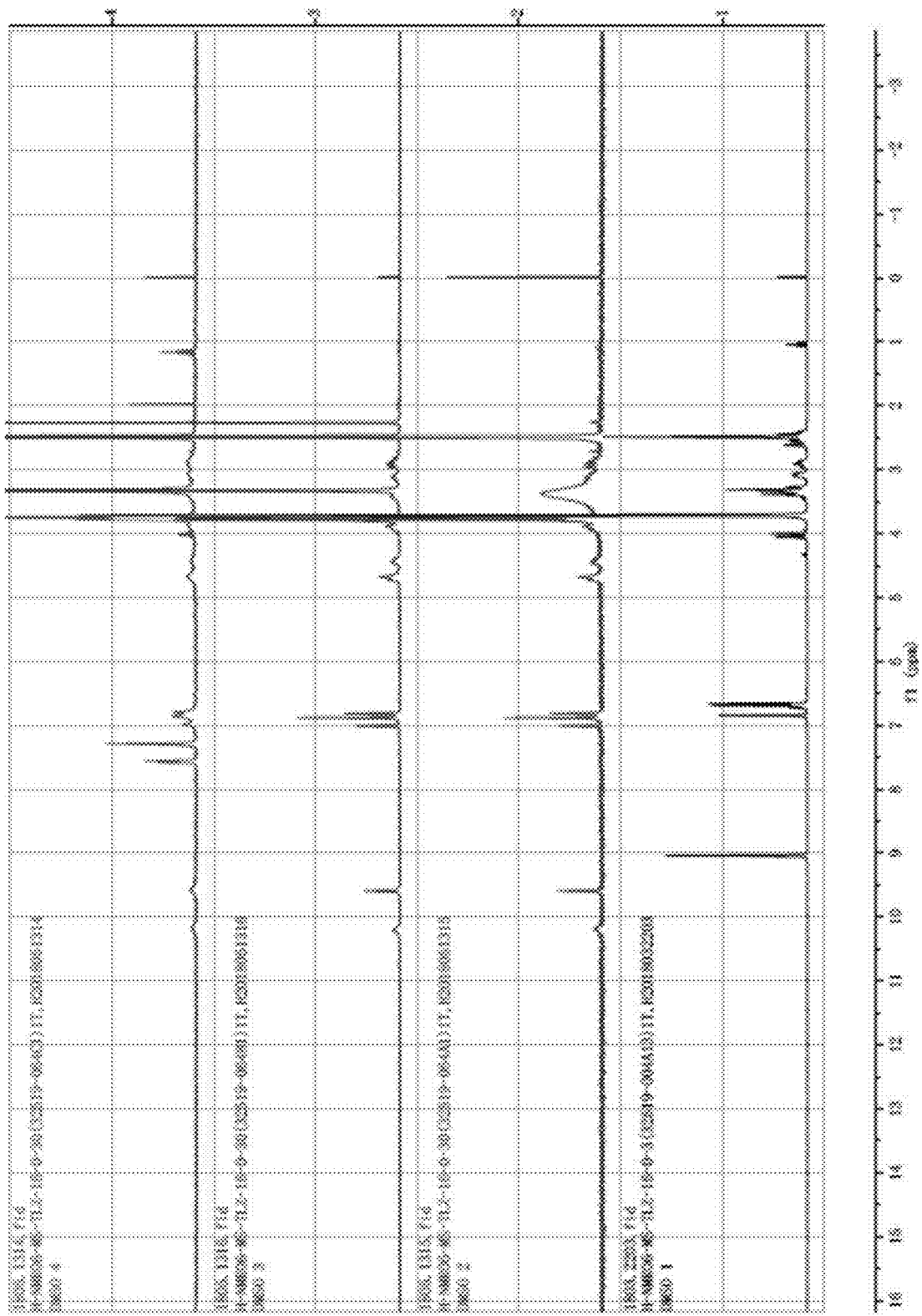
FIG. 31 illustrates representative $^1$HNMR spectrum of (a) Compound (1), (b) sulfate salt, (c) mesylate salt, and (d) benzene sulfonate salt of Compound (1).

FIG. 31 shows a representative $^1$HNMR spectrum of sulfate, mesylate, and bezene sulfonate salts of Compound (1). The $^1$HNMR spectrum shows that that Compound (1) forms salt with sulfuric acid, methanesulfonic acid, and benzenesulfonic acid.

Figure 32:
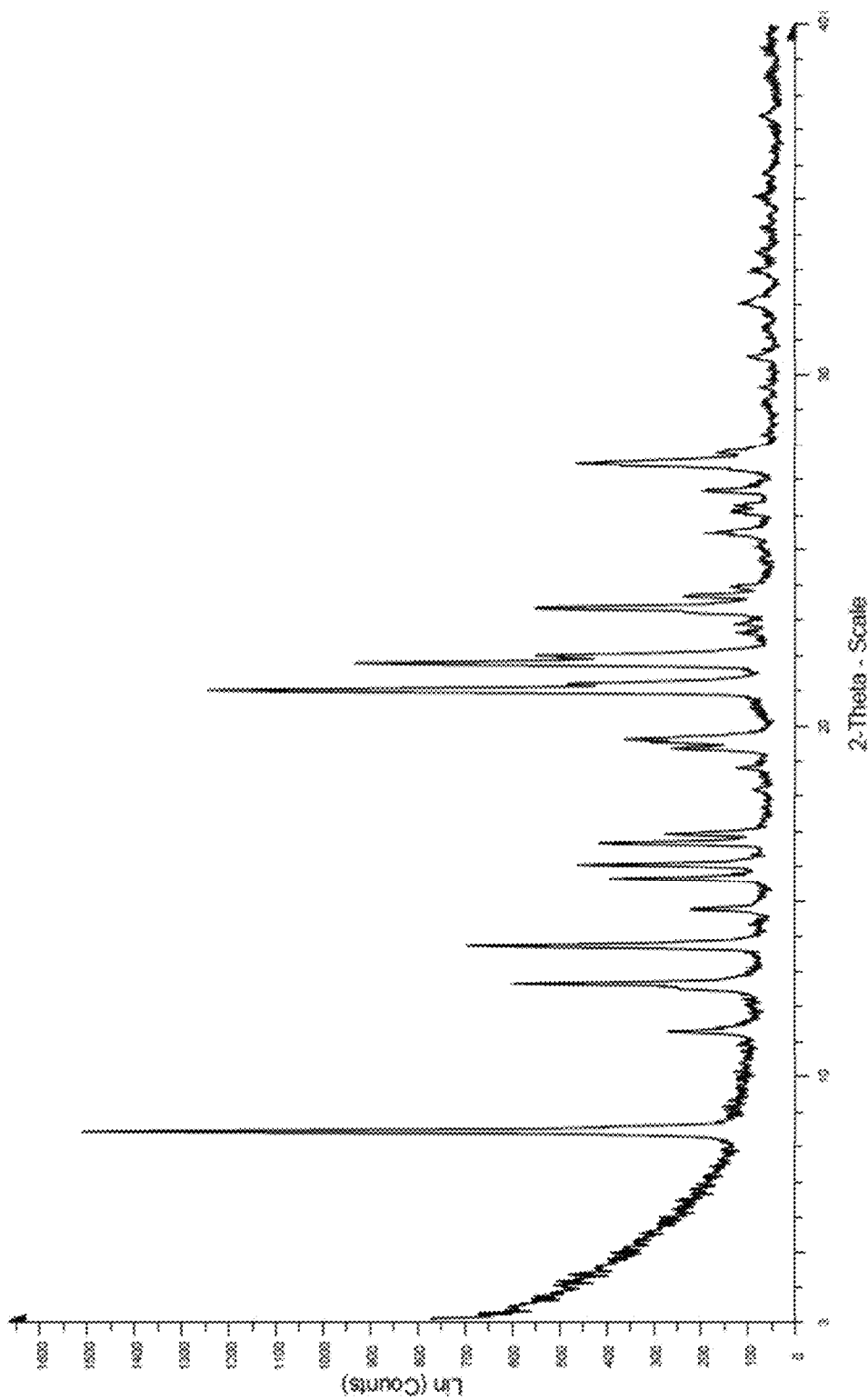
FIG. 32 illustrates representative XRPD patterns of sulfate salt of Compound (1).
Figure 33:
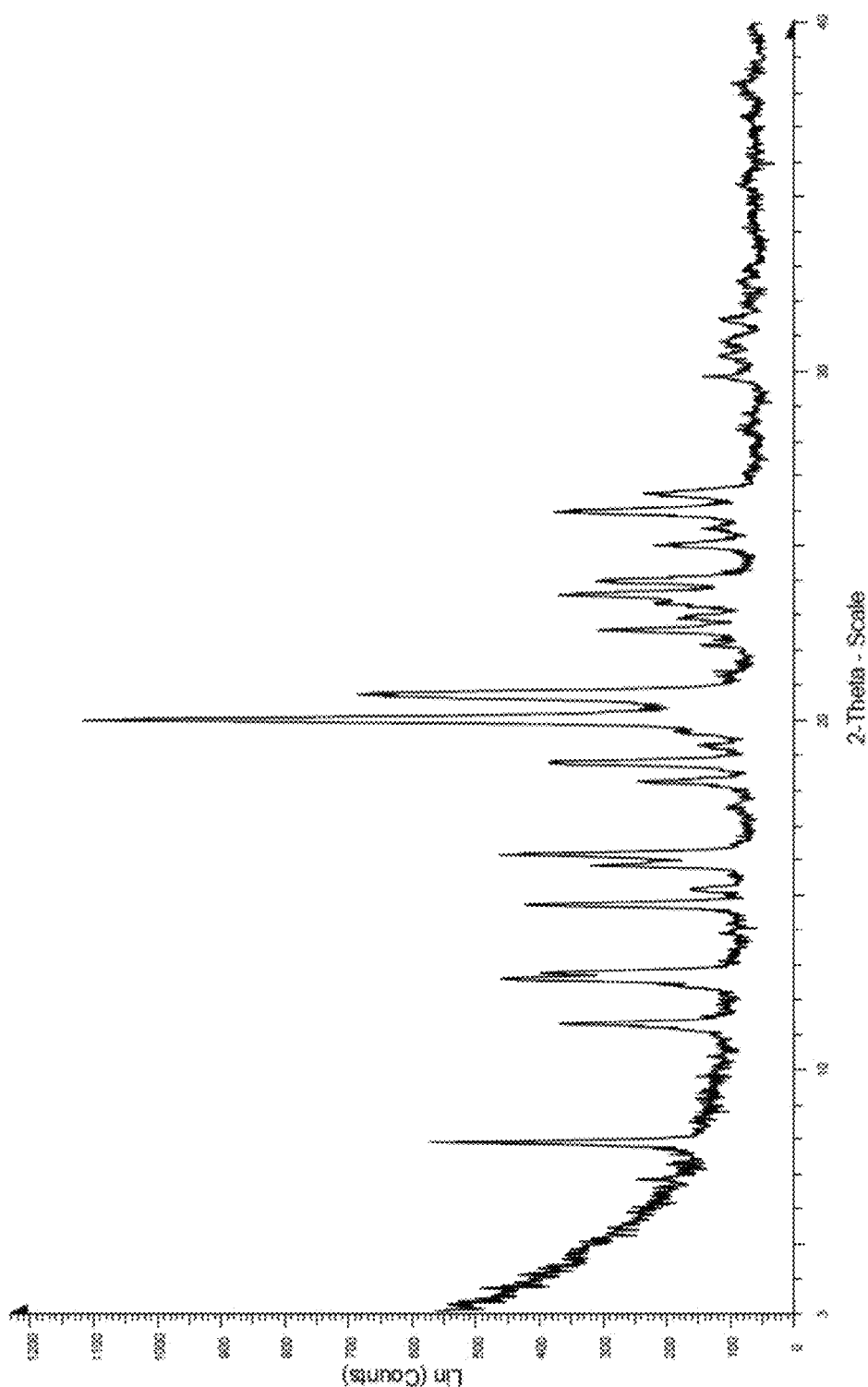
FIG. 33 illustrates representative XRPD patterns of mesylate salt of Compound (1).

FIG. 32 shows a representative XRPD pattern of sulfate salt. The XRPD pattern of sulfate salt is characterized by peaks, preferably three or more significant peaks, at approximately 8.4, 12.6, 13.7, 16.0, 16.7, 21.0, 21.8, 22.2, 23.4, and 27.5 degrees 2θ. FIG. 33 shows a representative XRPD pattern of mesylate salt. The XRPD pattern of The XRPD pattern of mesylate salt is characterized by peaks, preferably three or more significant peaks, at approximately 7.9, 11.3, 12.6, 12.9, 14.7, 16.1, 18.8, 20.0, 20.7, and 23.6 degrees 2θ. Tables 6 and 7 list the XRPD peaks of sulfate salt and mesylate salt, respectively.

TABLE 6

List of representative XRPD peaks of sulfate salt

| | Angle 2-Theta degree | Intensity % | d value Angstrom |
|---|---|---|---|
| 1 | 8.433 | 100 | 10.47628 |
| 2 | 11.259 | 17.6 | 7.85273 |
| 3 | 12.601 | 39.5 | 7.019 |
| 4 | 13.716 | 45.9 | 6.45111 |
| 5 | 14.737 | 14.5 | 6.00615 |
| 6 | 15.633 | 25.9 | 5.6641 |
| 7 | 16.034 | 30.4 | 5.52328 |
| 8 | 16.658 | 34.9 | 5.31764 |
| 9 | 17.048 | 20.5 | 5.1968 |
| 10 | 18.191 | 5.7 | 4.87295 |
| 11 | 18.818 | 8.1 | 4.71183 |
| 12 | 19.367 | 17 | 4.57955 |
| 13 | 19.62 | 23.7 | 4.5211 |
| 14 | 21.011 | 82.2 | 4.22479 |
| 15 | 21.784 | 61.7 | 4.07652 |
| 16 | 22.181 | 36.3 | 4.00454 |
| 17 | 22.649 | 8.1 | 3.92287 |
| 18 | 22.961 | 13.3 | 3.87017 |
| 19 | 23.356 | 36.3 | 3.8056 |
| 20 | 23.771 | 22.2 | 3.74003 |
| 21 | 24.042 | 11.1 | 3.69862 |
| 22 | 25.498 | 12.7 | 3.49051 |
| 23 | 26.236 | 7.7 | 3.39404 |
| 24 | 26.718 | 12.8 | 3.33393 |
| 25 | 27.466 | 30.4 | 3.24479 |
| 26 | 28.034 | 11.9 | 3.18035 |
| 27 | 29.242 | 4.4 | 3.05159 |

TABLE 6-continued

List of representative XRPD peaks of sulfate salt

| | Angle 2-Theta degree | Intensity % | d value Angstrom |
|---|---|---|---|
| 28 | 29.657 | 4.9 | 3.00983 |
| 29 | 30.522 | 6.3 | 2.92648 |
| 30 | 31.352 | 4.2 | 2.85091 |
| 31 | 32.056 | 8 | 2.78983 |
| 32 | 32.983 | 5.5 | 2.71353 |
| 33 | 33.485 | 5 | 2.67396 |
| 34 | 35.071 | 5.3 | 2.55661 |
| 35 | 37.409 | 4.9 | 2.40202 |
| 36 | 39.314 | 3.5 | 2.2899 |

TABLE 7

List of representative XRPD peaks of mesylate salt

| | Angle 2-Theta degree | Intensity % | d value Angstrom |
|---|---|---|---|
| 1 | 6.814 | 22.9 | 12.96112 |
| 2 | 7.858 | 53.5 | 11.24213 |
| 3 | 11.285 | 34.3 | 7.83485 |
| 4 | 12.576 | 51.5 | 7.03303 |
| 5 | 12.877 | 39.7 | 6.86939 |
| 6 | 13.877 | 10.7 | 6.37637 |
| 7 | 14.708 | 39.5 | 6.01816 |
| 8 | 15.147 | 15 | 5.84465 |
| 9 | 15.835 | 28.3 | 5.59217 |
| 10 | 16.132 | 43.1 | 5.48993 |
| 11 | 17.554 | 9.4 | 5.04811 |
| 12 | 18.248 | 22.8 | 4.8577 |
| 13 | 18.791 | 35.9 | 4.71852 |
| 14 | 19.255 | 12.6 | 4.60591 |
| 15 | 19.682 | 17.4 | 4.50693 |
| 16 | 20.03 | 100 | 4.42932 |
| 17 | 20.737 | 64.1 | 4.27995 |
| 18 | 21.295 | 10.1 | 4.16914 |
| 19 | 22.147 | 13.6 | 4.01062 |
| 20 | 22.583 | 28.6 | 3.93402 |
| 21 | 23.053 | 16.5 | 3.85497 |
| 22 | 23.383 | 22.9 | 3.80128 |
| 23 | 23.592 | 34.5 | 3.76808 |
| 24 | 24.135 | 29.7 | 3.68452 |
| 25 | 25.047 | 20.3 | 3.55244 |
| 26 | 25.516 | 13.7 | 3.48817 |
| 27 | 25.991 | 35 | 3.4255 |
| 28 | 26.504 | 21.9 | 3.36029 |
| 29 | 28.399 | 7.1 | 3.14023 |
| 30 | 29.874 | 13.2 | 2.98846 |
| 31 | 30.479 | 10.9 | 2.93049 |
| 32 | 30.912 | 10.6 | 2.89045 |
| 33 | 31.496 | 10.8 | 2.83821 |
| 34 | 32.603 | 7.8 | 2.7443 |
| 35 | 38.306 | 8.9 | 2.3478 |

Figure 34:
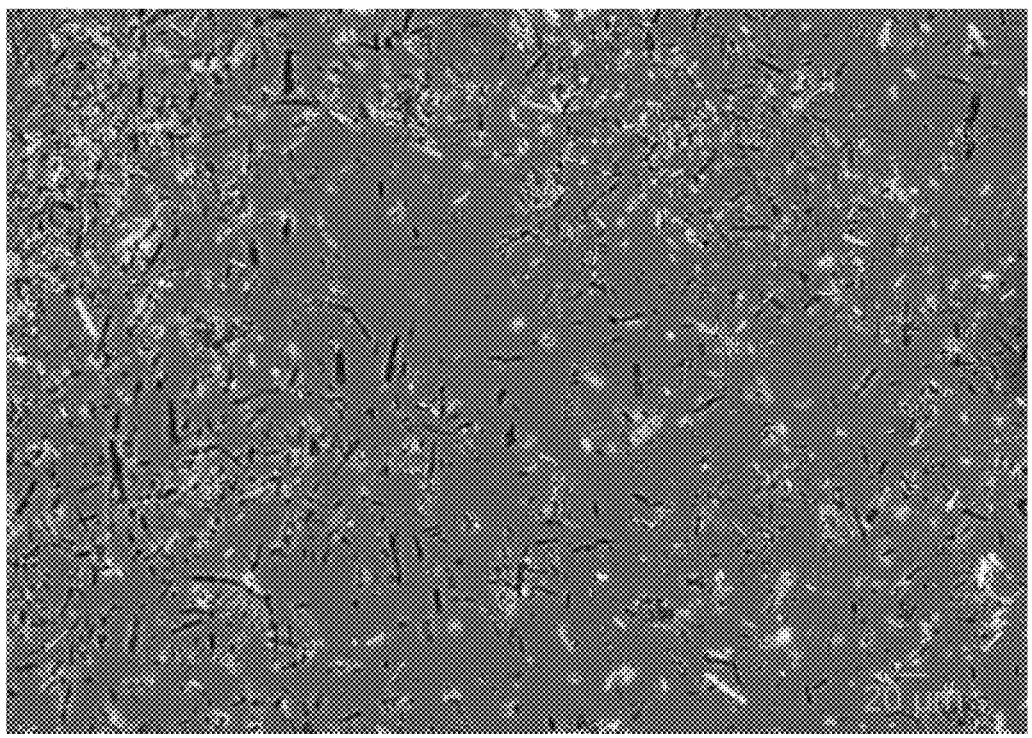
FIG. 34 illustrates a representative PLM image of (a) sulfate and (b) mesylate salts of Compound (1).
Figure 34:
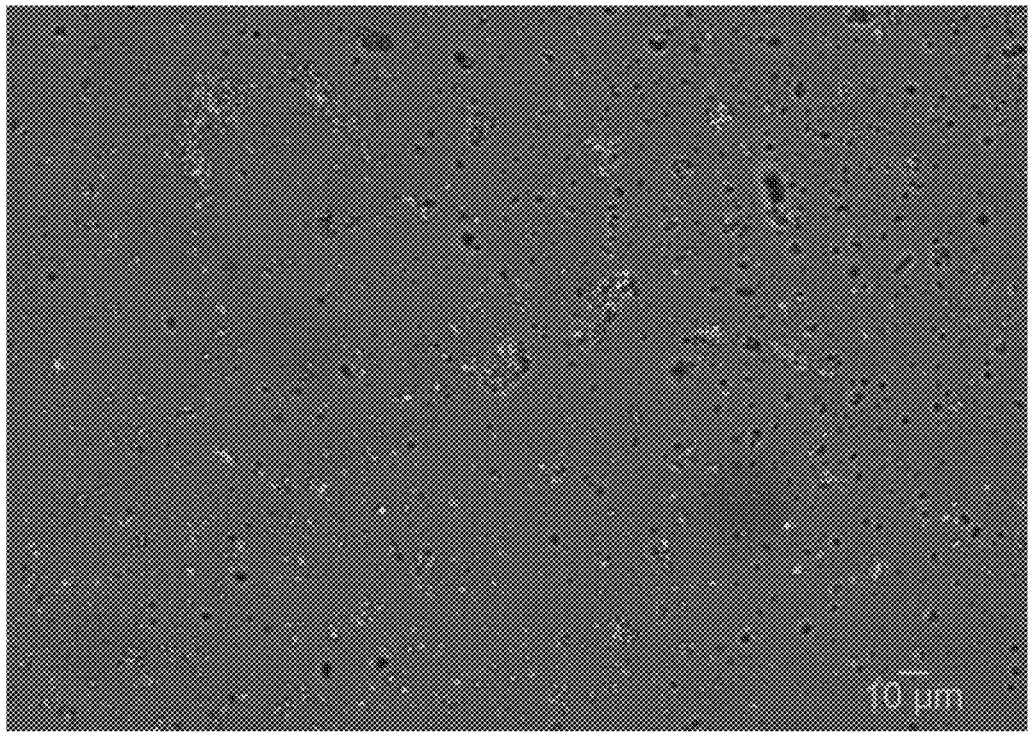

Representative PLM images of sulfate salt and mesylate salt are shown in FIG. 34.

Figure 35:
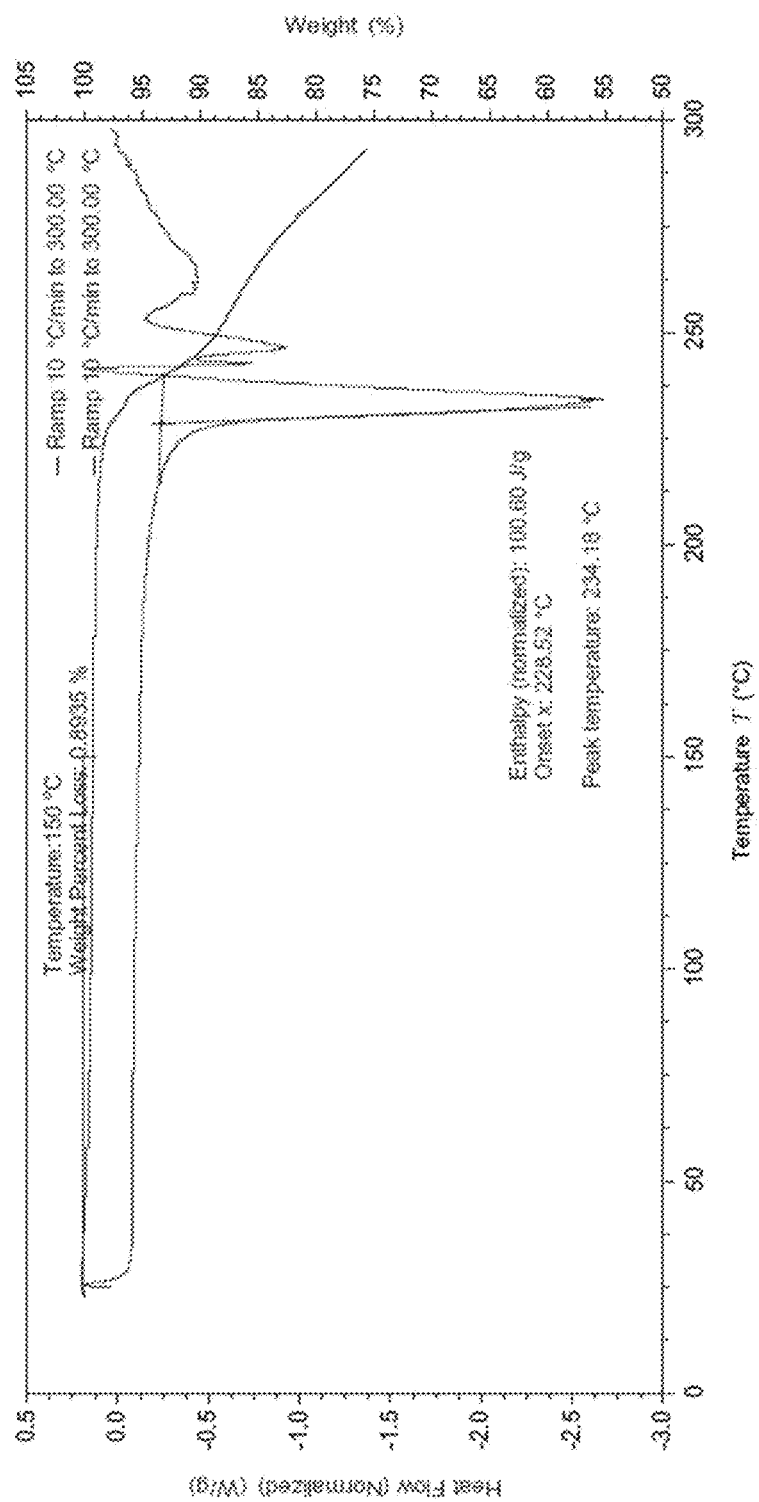
FIG. 35 illustrates representative DSC and TGA profiles of sulfate salt of Compound (1).
Figure 36:
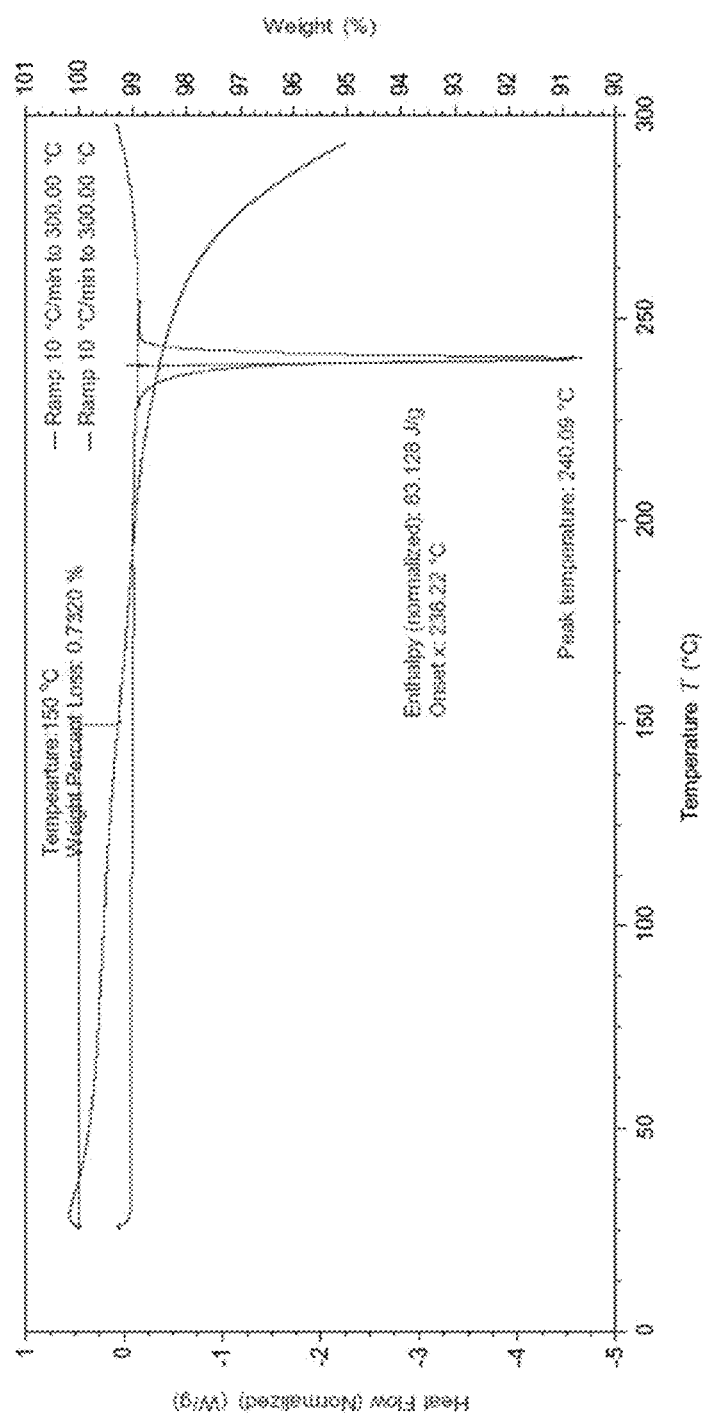
FIG. 36 illustrates representative DSC and TGA profiles of mesylate salt of Compound (1).
Figure 37A:
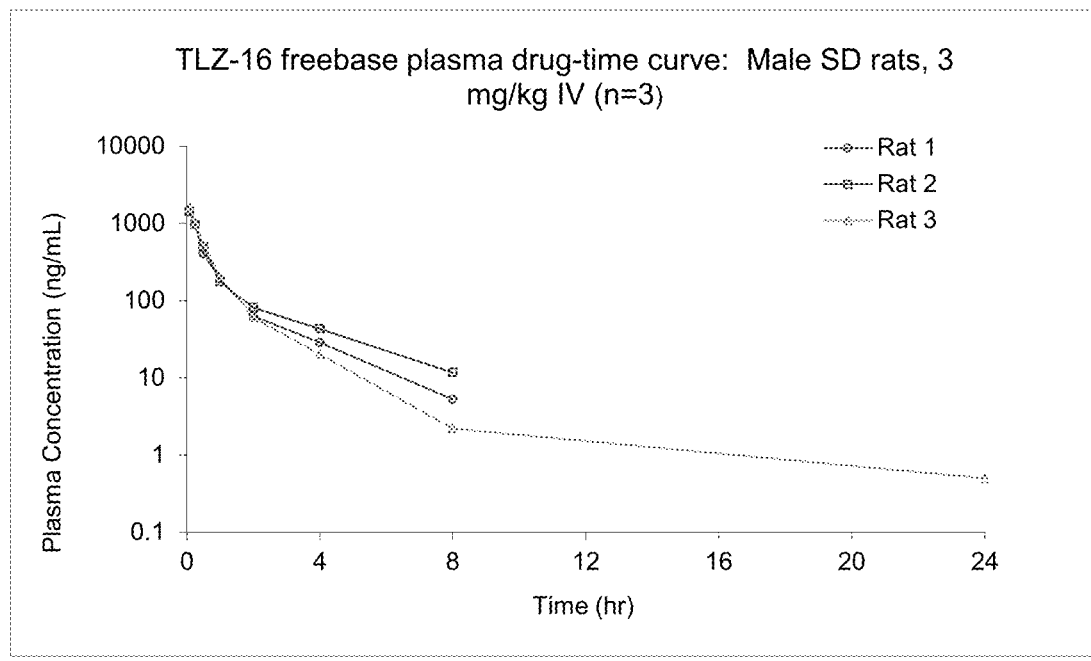
FIGS. 37A and 37B show the plasma drug-time curves obtained from male rats administrated with TLZ-16 freebase (compound (1)) at 3 mg/kg IV and 10 mg/kg POA.
Figure 37B:
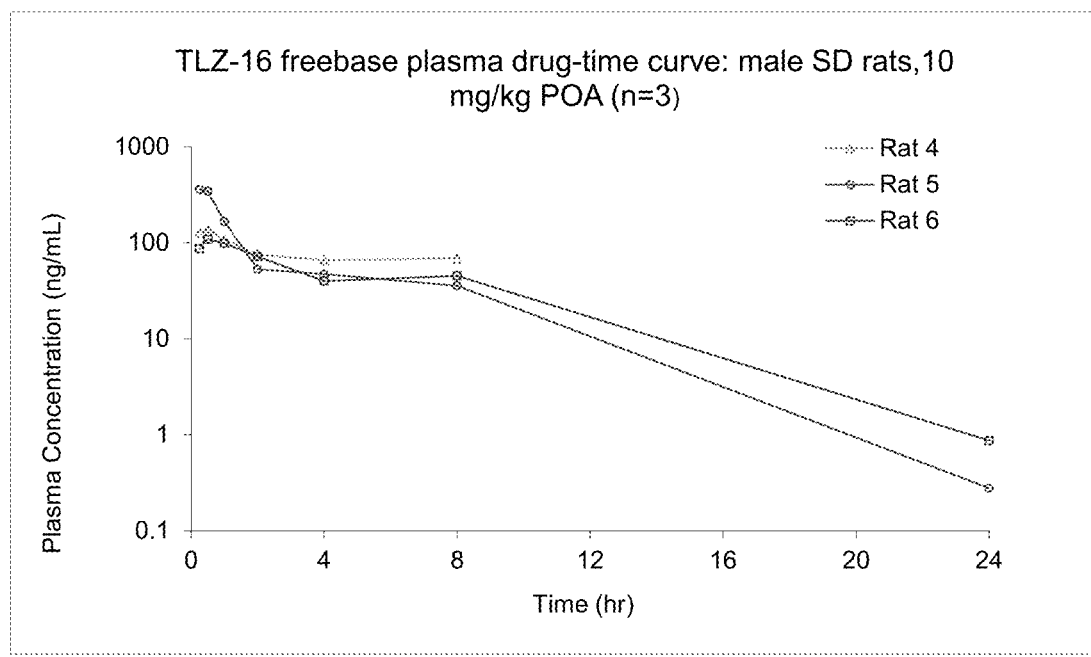
Figure 38:
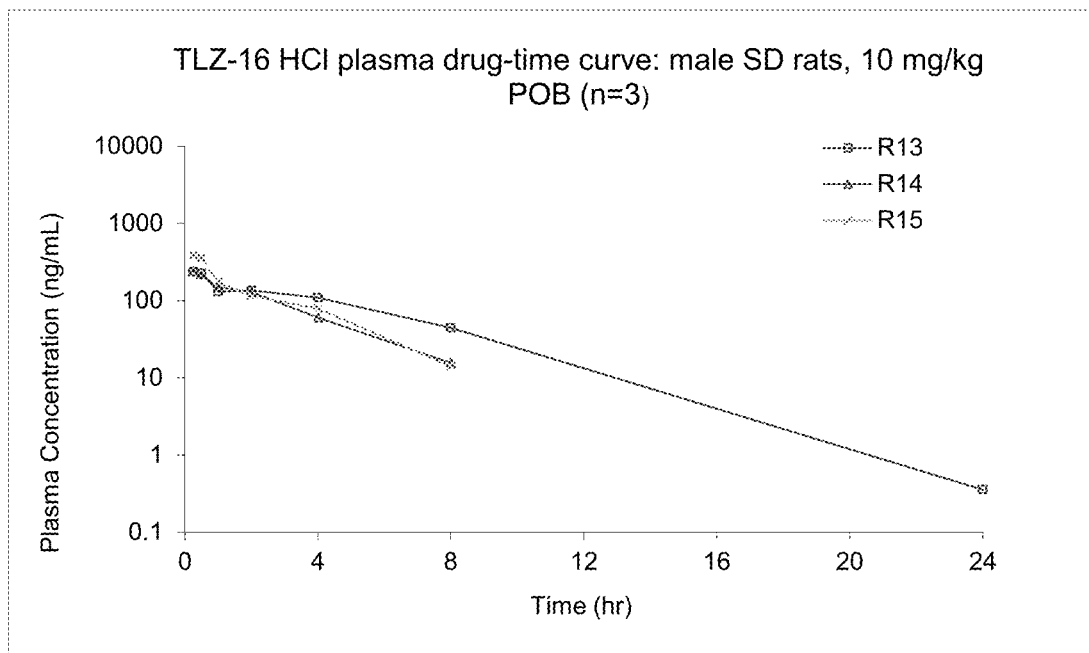
FIG. 38 shows the plasma drug-time curve obtained from male rats administrated with TLZ-16 HCl at 10 mg/kg POB.
Figure 39:
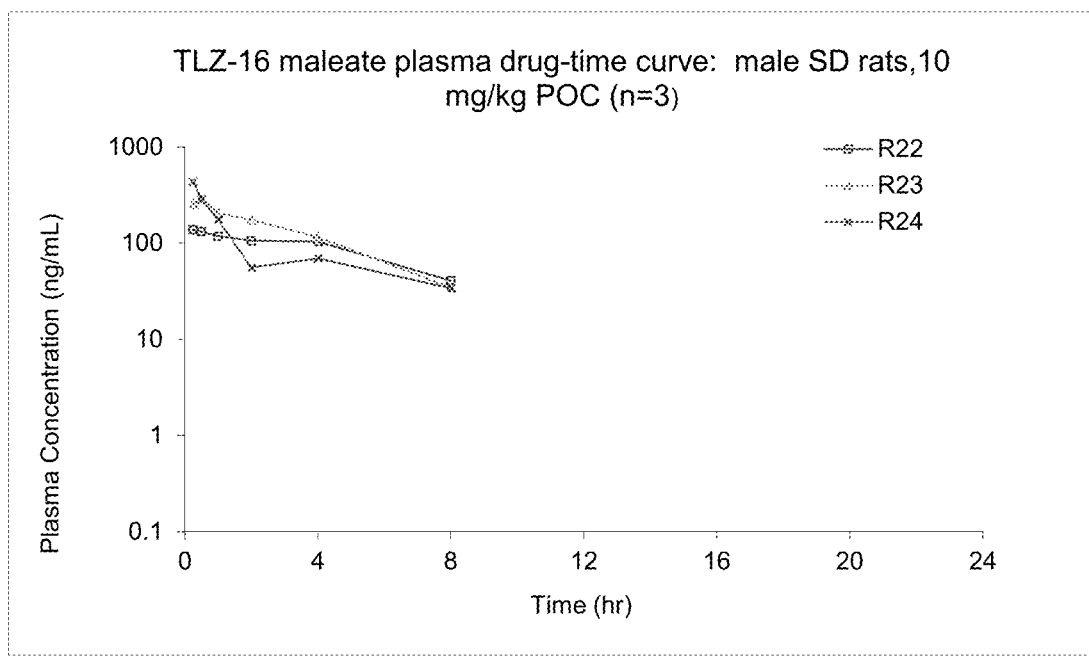
FIG. 39 shows the plasma drug-time curve obtained from male rats administrated with TLZ-16 maleate at 10 mg/kg POC.
Figure 40:
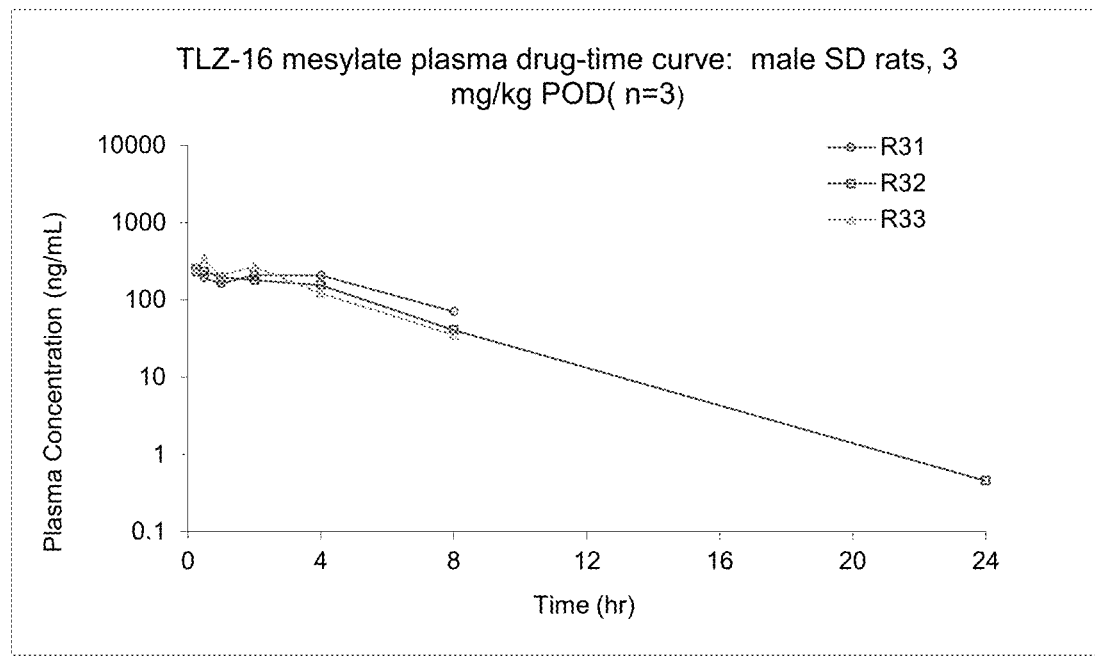
FIG. 40 shows the plasma drug-time curves obtained from male rats administrated with TLZ-16 mesylate at 10 mg/kg POD.
Figure 41:
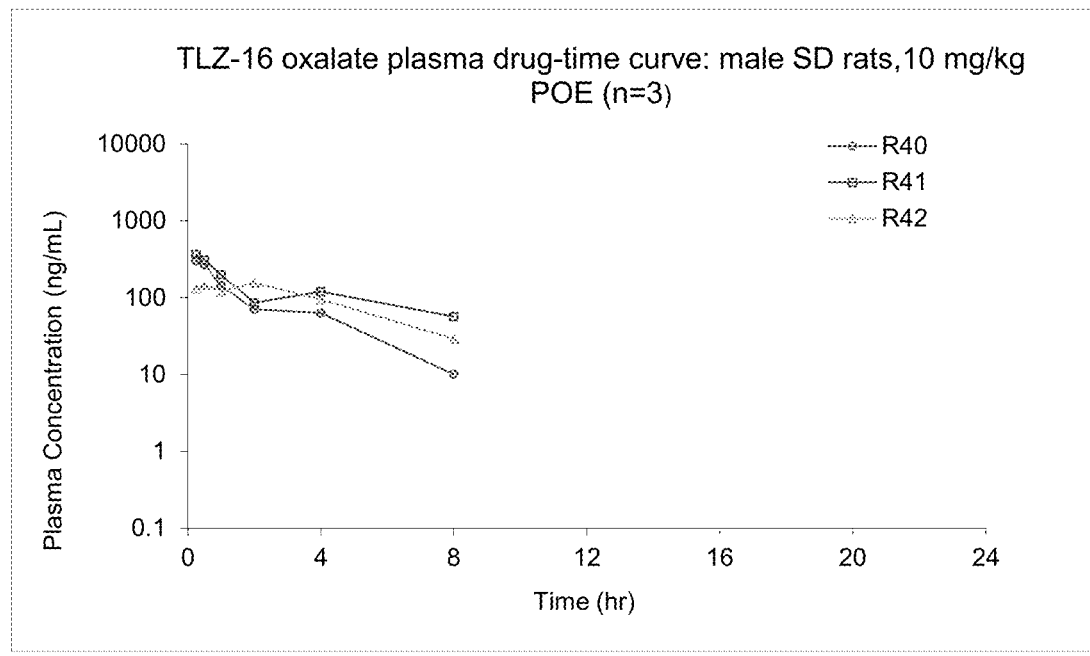
FIG. 41 shows the plasma drug-time curves obtained from male rats administered with TLZ-16 oxalate at 10 mg/kg POE.
Figure 42:
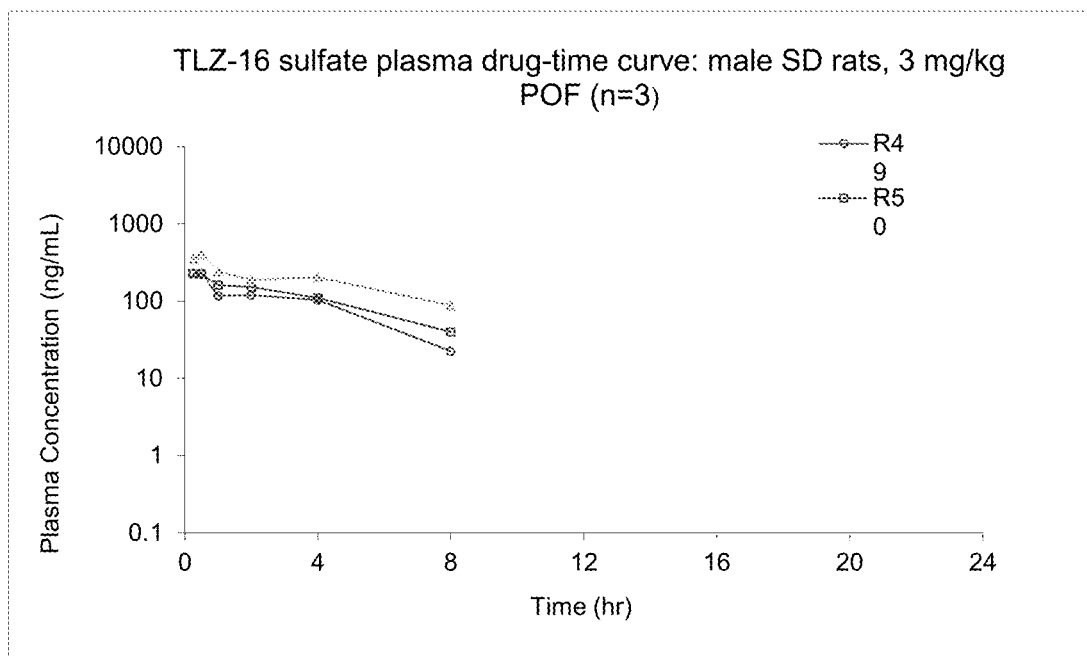
FIG. 42 shows the plasma drug-time curves obtained from male rats administered with TLZ-16 sulfate at 10 mg/kg POF.
Figure 43:
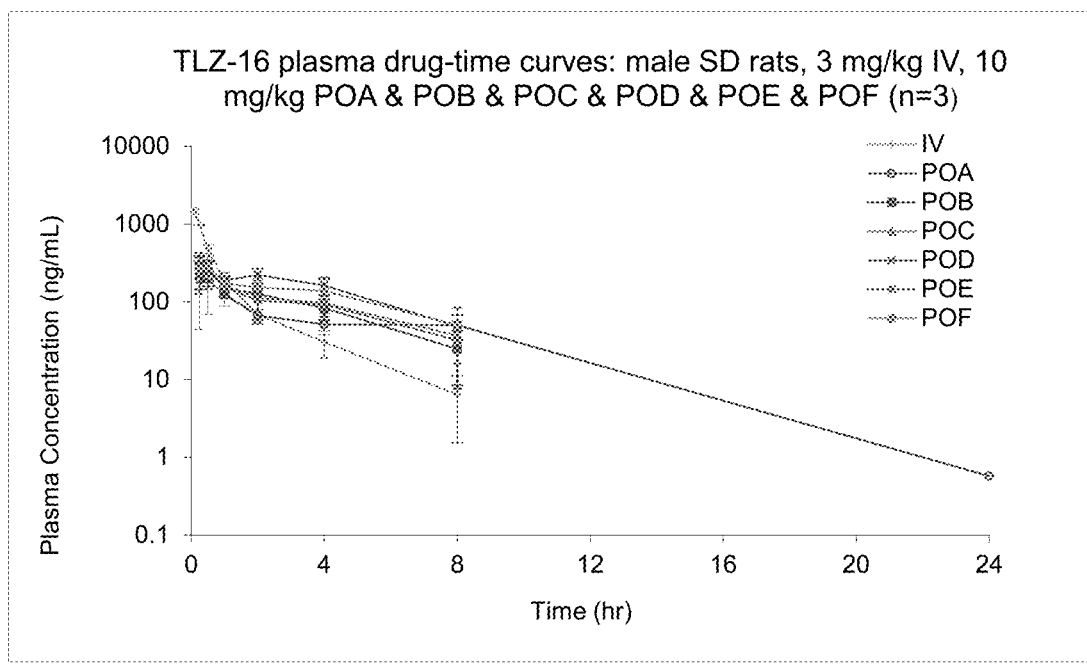
FIG. 43 shows the comparison of TLZ-16 plasma drug-time curves: male SD rats, 3 mg/kg IV, 10 mg/kg POA & POB & POC & POD & POE & POF (n=3).

Representative thermal characteristics of sulfate salt are shown in FIG. 35. TGA data indicates that there is −0.89% weight loss between RT and 150° C., which is due to the loss of the residue solvent. DSC data illustrates that sulfate salt has one endothermic peak with the onset and peak temperatures of 229 and 234° C. respectively, and the enthalpy of the endothermic peak is about 101 J/g. Representative thermal characteristics of mesylate salt are shown in FIG. 36. TGA data indicates that there is −0.73% weight loss between RT and 150° C., which is due to the loss of the residue solvent. DSC data illustrates that mesylate salt has one endothermic peak with the onset and peak temperatures of 238 and 240° C. respectively, and the enthalpy of the endothermic peak is about 83 J/g.

Solubility studies of sulfate and mesylate salt in water (in 2 hours) is higher than that of the free base, which is improved from free base solubility of less than 1 mg/mL to the salt solubility of approximately 20 mg/mL.

Methods of Use and Pharmaceutical Compositions

Crystalline salt forms of the invention exhibit physical characteristics that are beneficial for drug manufacture, storage and/or use.

This invention encompasses methods of treating and preventing a wide variety of diseases and conditions using crystalline salt forms of the invention. In each of the methods, a therapeutically or prophylactically effective amount of the crystalline salt or polymorph is administered to a patient in need of such treatment or prevention. Examples of such disease and conditions include, but are not limited to, chronic pain, anxiety, insomnia, hyperlipidemia, hypercholesterolemia, hypertriglyceridemia, hepatic steatosis, and metabolic syndrome. Examples of these and other diseases and disorders that can be treated or prevented using compositions of the invention are described in Pat. Appl. No. US20180071269A1, WO2009002873A1, EP1911456A1, CN101327214A, and CN106176740A. The entirety of each of the patents and patent applications cited herein is incorporated herein by reference.

The therapeutically-effective amount of any of the crystalline salt forms disclosed herein is not particular limited, and the administration step can be carried out by oral, intravenous, intramuscular or subcutaneous in the amount of about 1 mg to about 1,000 mg, in the amount of about 5 mg to about 500 mg, in the amount of about 10 mg to about 200 mg, in the amount of about 10 mg to about 150 mg, in the amount of about 10 mg to about 120 mg, in the amount of about 10 mg, in the amount of about 20 mg, in the amount of about 40 mg, in the amount of about 80 mg, or in the amount of about 120 mg.

Depending on the disease to be treated and the subject's condition, crystalline salt forms of the invention can be administered by oral, parenteral (e.g., intramuscular, intraperitoneal, intravenous, ICV, intracisternal injection or infusion, subcutaneous injection, or implantation), inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. Because individual crystalline salt forms have different dissolution, stability, and other properties, the optimal polymorph used in methods of treatment may depend on the route of administration. For example, crystalline salt forms that are readily soluble in aqueous solutions are preferably used to provide liquid dosage forms, whereas crystalline salt forms that exhibit great thermal stability may be preferred in the manufacture of solid dosage forms (e.g., tablets and capsules).

Although the physical characteristics of crystalline salt forms can, in some cases, affect their bioavailability, amounts of the polymorphs that are therapeutically or prophylactically effective in the treatment of various disease and conditions can be readily determined by those of ordinary skill in the pharmacy or medical arts.

The invention encompasses pharmaceutical compositions and single unit dosage forms that can be used in methods of treatment and prevention, which comprise one or more crystalline salt forms of Compound (1) and optionally one or more excipients or diluents. Specific compositions and dosage forms are disclosed in the various patents and patent applications incorporated herein by reference.

EXAMPLES

The embodiments described above in addition to other embodiments can be further understood with reference to the following examples:

Methods Identifying Different Polymorphs

Slurry Study at Room Temperature

Certain amount of solid was added into specific solvent, and the mixture slurry was stirred at RT for 3 days. The slurry were filtered and characterized by XRPD, and new patterns obtained were further analyzed by DSC and TGA.

Slurry Study at 50° C.

The slurry study at room temperature samples were heated to 50° C., and stirred for 1 day. The slurry was filtered and characterized by XRPD, and new patterns obtained were further analyzed by DSC and TGA.

Evaporation Crystallization

Certain amount of solvent was added into the slurry study at room temperature samples. The slurry samples were filtered by 0.22 μm membrane, and then the saturated solutions were evaporated under ambient condition. New patterns obtained were further analyzed by DSC and TGA.

Anti-Solvent Crystallization

Certain amount of crystalline salt was added MeOH and/or $H_2O$ to form a solution, followed by adding anti-solvent to precipitate out the solids. The solids were characterized by XRPD and new patterns obtained were further analyzed by DSC and TGA.

Preparing the Hydrochloride Salt Form I 1.07 g Compound (1) was dissolved in 25 mL acetone, followed by reacting with 333.3 μL concentrated HCl. The reaction mixture was stirred overnight, and solids were precipitated out from the solution. Solids were collected by filtration and dried at 40° C. under vacuum for 5 hours. The solids were characterized as crystalline materials by PLM and XRPD, with a DSC melting onset temperature ("$T_{onset}$") of about 252° C.

Preparing the Oxalate Salt Form I 1.07 g Compound (1) was dissolved in 72 mL EtOAc, followed by reacting with 420 mg oxalic acid. The reaction mixture was stirred overnight, and solids were precipitated out from the solution. Solids were collected by filtration and dried at 40° C. under vacuum for 5 hours. The solids were characterized as crystalline materials by PLM and XRPD, with a DSC melting $T_{onset}$ of about 205° C.

Preparing the Maleate Salt 1.03 g Compound (1) was dissolved in 72 mL EtOAc, followed by reacting with 356.2 mg maleic acid. The reaction mixture was stirred overnight, and solids were precipitated out from the solution. Solids were collected by filtration and dried at 40° C. under vacuum for 5 hours. The solids were characterized as crystalline materials by PLM and XRPD, with a DSC melting $T_{onset}$ of about 193° C.

Preparing the Sulfate Salt 15 mg Compound (1) was dissolved in 1 mL EtOAc, followed by reacting with 500 μL $H_2SO_4$ (0.07 mol/L) EtOAc solution. The reaction mixture was stirred overnight, and solids were precipitated out from the solution. Solids were collected by filtration and dried at 40° C. under vacuum for 5 hours. The solids were characterized as crystalline materials by PLM and XRPD, with a DSC melting $T_{onset}$ of about 229° C.

Preparing the Mesylate Salt 15 mg Compound (1) was dissolved in 1 mL EtOAc, followed by reacting with 2.6 μL methanesulfonic acid. The reaction mixture was stirred overnight, and solids were precipitated out from the solution. Solids were collected by filtration and dried at 40° C. under vacuum for 5 hours. The solids were characterized as crystalline materials by PLM and XRPD, with a DSC melting $T_{onset}$ of about 238° C.

Exemplary Embodiments

A crystalline salt form of Compound (1)

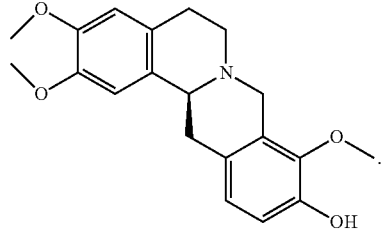

Compound (1)

A crystalline salt form of Compound (1), wherein the crystalline salt form is a hydrochloride, oxalate, maleate, sulfate, or mesylate salt.

A crystalline salt form of Compound (1), wherein the crystalline salt form is a hydrochloride salt having an X-ray powder diffraction pattern comprising peaks selected from the group at approximately 9.7, 10.1, 14.3, 15.0, 17.5, 18.9, 21.9, and 23.7 degrees 2θ.

A crystalline salt form of Compound (1), wherein the crystalline salt form is a hydrochloride salt having a differential scanning calorimetry thermogram endotherm $T_{onset}$ at approximately 252° C. and an X-ray powder diffraction pattern comprising peaks selected from the group at approximately 9.7, 10.1, 14.3, 15.0, 17.5, 18.9, 21.9, and 23.7 degrees 2θ.

A crystalline salt form of Compound (1), wherein the crystalline salt form is a oxalate salt having an X-ray powder diffraction pattern comprising peaks selected from the group at approximately 11.7, 13.0, 15.4, 16.3, 19.6, 22.1, and 24.5 degrees 2θ.

A crystalline salt form of Compound (1), wherein the crystalline salt form is a oxalate salt having a differential scanning calorimetry thermogram endotherm $T_{onset}$ at approximately 205° C. and an X-ray powder diffraction pattern comprising peaks selected from the group at approximately 11.7, 13.0, 15.4, 16.3, 19.6, 22.1, and 24.5 degrees 2θ.

A crystalline salt form of Compound (1), wherein the crystalline salt form is a maleate salt having an X-ray powder diffraction pattern comprising peaks selected from the group at approximately 8.0, 10.4, 12.4, 14.0, 15.3, 16.4, 19.3, 21.5, and 23.3 degrees 2θ.

A crystalline salt form of Compound (1), wherein the crystalline salt form is a maleate salt having a differential scanning calorimetry thermogram endotherm $T_{onset}$ at approximately 193° C. and an X-ray powder diffraction pattern comprising peaks selected from the group at approximately 8.0, 10.4, 12.4, 14.0, 15.3, 16.4, 19.3, 21.5, and 23.3 degrees 2θ.

A crystalline salt form of Compound (1), wherein the crystalline salt form is a sulfate salt having an X-ray powder diffraction pattern comprising peaks selected from the group at approximately 8.4, 12.6, 13.7, 16.7, 21.0, 21.8, 22.2, and 23.4 degrees 2θ.

A crystalline salt form of Compound (1), wherein the crystalline salt form is a sulfate salt having a differential scanning calorimetry thermogram endotherm $T_{onset}$ at approximately 229° C. and an X-ray powder diffraction pattern comprising peaks selected from the group at approximately 8.4, 12.6, 13.7, 16.7, 21.0, 21.8, 22.2, and 23.4 degrees 2θ.

A crystalline salt form of Compound (1), wherein the crystalline salt form is a mesylate salt having an X-ray powder diffraction pattern comprising peaks selected from the group at approximately 7.9, 11.3, 12.6, 12.9, 14.7, 16.1, 20.0, and 20.7 degrees 2θ.

A crystalline salt form of Compound (1), wherein the crystalline salt form is a mesylate salt having a differential scanning calorimetry thermogram endotherm $T_{onset}$ at approximately 238° C. and an X-ray powder diffraction pattern comprising peaks selected from the group at approximately 7.9, 11.3, 12.6, 12.9, 14.7, 16.1, 20.0, and 20.7 degrees 2θ.

A pharmaceutical composition comprising any of the crystalline salt forms disclosed herein and a pharmaceutically acceptable carrier.

A pharmaceutical composition comprising any of the crystalline salt forms disclosed herein, wherein the pharmaceutical composition is a single unit dosage form.

A pharmaceutical composition comprising any of the crystalline salt forms disclosed herein, wherein the crystalline salt form is in substantially pure form.

A method of treating chronic pain, anxiety, insomnia, hyperlipidemia, hypercholesterolemia, hypertriglyceridemia, hepatic steatosis, and metabolic syndrome in a mammal comprising administering to the mammal a therapeutically-effective amount of any of the pharmaceutical compositions disclosed herein.

A method of treating chronic pain, anxiety, insomnia, hyperlipidemia, hypercholesterolemia, hypertriglyceridemia, hepatic steatosis, and metabolic syndrome in a mammal comprising administering to the mammal a pharmaceutical composition comprising a therapeutically-effective amount of any of the crystalline salt forms disclosed herein.

Pharmacokinetic and Brain Penetration Study

Purpose

To determine pharmacokinetic profile and brain penetration of TLZ-16 freebase (Compound (1)) and its five salts Study Design A. Dosing Information The study groups are shown in the following table.

| Group | Treatment | Dose Level (mg/kg) (Equal to freebase) | Dose Volume (mL/kg) | Conc. (mg/mL) | Administration Route | No. of Animals |
|---|---|---|---|---|---|---|
| 1 | TLZ-16 | 3 | 5 | 0.6 | IV | 3MALE |
| 2 | freebase | 10 | 10 | 1 | PO-A | 3MALE |
| 3 | TLZ-16 freebase | 10 | 10 | 1 | PO-A | 6MALE |
| 4 | TLZ-16 | 10 | 10 | 1 | PO-B | 3MALE |
| 5 | HCl | 10 | 10 | 1 | PO-B | 6MALE |
| 6 | TLZ-16 | 10 | 10 | 1 | PO-C | 3MALE |
| 7 | maleate | 10 | 10 | 1 | PO-C | 6MALE |
| 8 | TLZ-16 | 10 | 10 | 1 | PO-D | 3MALE |
| 9 | mesylate | 10 | 10 | 1 | PO-D | 6MALE |
| 10 | TLZ-16 | 10 | 10 | 1 | PO-E | 3MALE |
| 11 | oxalate | 10 | 10 | 1 | PO-E | 6MALE |
| 12 | TLZ-16 | 10 | 10 | 1 | PO-F | 3MALE |
| 13 | sulfate | 10 | 10 | 1 | PO-F | 6MALE |

Note:
the dose level of salt forms should be corrected by the salt factor

Animal feeding control: All animals for IV and PO administration will have free access to food and water.

Dose formulation processing during dosing: The dose formulations will be kept at room temperature.

B. Pharmacokinetics (PK) Schedule:

| Group | PK time points |
|---|---|
| 1 | Plasma: 0, 0.083 h, 0.25 h, 0.5 h, 1 h, 2 h, 4 h, 8 h, 24 h post dose |
| 2, 4, 6, 8, 10, 12 | Plasma: 0, 0.25 h, 0.5 h, 1 h, 2 h, 4 h, 8 h, 24 h post dose Brain: 24 h |
| 3, 5, 7, 9, 11, 13 | Plasma and Brain: 1 h, 2 h, 4 h (N = 2/time point) post dose |

| Acceptable Time Ranges for Blood Collection | |
|---|---|
| Time Points | Acceptable Time Ranges |
| 5-30 min | Within ±0.25 minute |
| 1-2 hr | Within ±2 minutes |
| 4-24 hr | Within ±10 minutes |

C. Blood Sample Collection and Processing

| | |
|---|---|
| Collection Site: | Jugular vein |
| Volume Collected: | ~0.2 mL per time point |
| Anticoagulant: | EDTA-K2 |
| Blood Samples Processing and Storage: | 1) Approximately 0.2 mL blood will be collected at each time point. Blood of each sample will be transferred into plastic micro centrifuge tubes containing anticoagulant. 2) All blood samples will be centrifuged at 4,000 g for 5 minutes at 4° C. to obtain plasma. The samples will be stored in a freezer at −75 ± 15° C. prior to analysis. |
| Brain Samples Processing and Storage: | 1) The animal will be fully exsanguinated prior to brain collection. Procedure: open chest cavity, cut ventricle and perform a gentle iv saline flush (saline flush volume ~20 ml) with the animal placed head down at a 45 degree angle to facilitate blood removal. 2) Brain samples will be collected at adopted time point, quick frozen in ice box. |

-continued

3) All brain samples will be weighted and homogenated with water by brain weight (g) to water volume (mL) at ratio 1:3 before analysis. The actual concentration is the detected value multiplied by the dilution factor.

D. Evaluations during the In-life Phase:

| Procedure | Frequency |
|---|---|
| Cageside Observations: | Twice daily |
| Detailed Clinical Observations: | Once prior to dosing on Day 1 |
| Body Weight: | Once prior to each dosing |

Note: Unscheduled clinical observations (cageside or detailed) will also be performed, as needed.

E. Test System

| | |
|---|---|
| Species/Strain/Sex: | Male SD Rat |
| Source: | Si Bei Fu Laboratory Animal Technology Co. Ltd |
| Age at Day of Dosing: | Approximately 6-8 weeks |
| Weight at Day of Dosing: | Approximately 200-300 g |

Test Article and Dose Formulations
A. Test Article Information

| Test Article Identification | Lot No. | Retest Date | MW | FW | Storage Condition |
|---|---|---|---|---|---|
| TLZ-16 freebase | | | 341.41 | 341.41 | RT |
| TLZ-16 HCl | | | 341.41 | 377.87 | RT |
| TLZ-16 maleate | | | 341.41 | 457.48 | RT |
| TLZ-16 mesylate | | | 341.41 | 437.51 | RT |
| TLZ-16 oxalate | | | 341.41 | 431.44 | RT |
| TLZ-16 sulfate | | | 341.41 | 439.48 | RT |

B. Dose Formulation

| PK Sample Analyses | |
|---|---|
| Formulation Frequency: | Freshly prepared on of the day of dosing |
| Vehicle Composition: | IV/POA: 20% HP-β-CD in water POB/POC/POD/POE/POF: Water |
| Storage Condition: | Dose formulation for dosing: Room temperature |
| Preparation Procedures: | TBD |

Concentrations of Test Article in the plasma samples will be analyzed using a LC-MS/MS method.

WinNonlin (Phoenix™, version 6.1) or other similar software will be used for pharmacokinetic calculations. The following pharmacokinetic parameters will be calculated, whenever possible from the plasma concentration versus time data:

IV administration: $T_{1/2}$, $C_0$, $AUC_{last}$, $AUC_{inf}$, $MRT_{inf}$, Cl, Vss, Number of Points for Regression.

PO administration: $T_{1/2}$, $C_{max}$, $T_{max}$, $MRT_{inf}$, $AUC_{inf}$, $AUC_{last}$, F %, Number of Points for Regression.

The pharmacokinetic data will be described using descriptive statistics such as mean, standard deviation.

Additional pharmacokinetic or statistical analysis may be performed at the discretion of the contributing scientist, and will be documented in the data summary.

Record Retention

All study raw data generated by Pharmaron will be retained in the Archives located at Pharmaron for a period of 1 year following issuance of the final data summary.

Study Data Summary

A data summary (excel file) will be sent to the Sponsor at the completion of sample analyses.

Results (1) TLZ-16 freebase

TLZ-16 freebase concentration in plasma (IV, 3 mg/kg)

| | Conc. (ng/mL) | | | Mean | RSD |
|---|---|---|---|---|---|
| Time (h) | Rat 1 | Rat 2 | Rat 3 | (ng/mL) | (ng/mL) |
| 0 | BLOQ | BLOQ | BLOQ | NA | NA |
| 0.083 | 1420 | 1410 | 1610 | 1480 | 113 |
| 0.25 | 974 | 960 | 995 | 976 | 17.6 |
| 0.5 | 401 | 496 | 536 | 478 | 69.3 |
| 1 | 192 | 174 | 206 | 191 | 16.0 |
| 2 | 63.3 | 81.2 | 60.6 | 68.4 | 11.2 |
| 4 | 28.6 | 43.0 | 20.2 | 30.6 | 11.5 |
| 8 | 5.24 | 11.7 | 2.20 | 6.38 | 4.85 |
| 24 | BLOQ | BLOQ | 0.500 | NA | NA |

Note:
BLOQ = below limit of quantitation (0.2 ng/mL)

TLZ-16 freebase concentration in plasma (POA, 10 mg/kg)

| | Conc. (ng/mL) | | | Mean | RSD |
|---|---|---|---|---|---|
| Time (h) | Rat 4 | Rat 5 | Rat 6 | (ng/mL) | (ng/mL) |
| 0 | BLOQ | BLOQ | BLOQ | NA | NA |
| 0.25 | 127 | 358 | 86.7 | 191 | 146 |
| 0.5 | 139 | 344 | 109 | 197 | 128 |
| 1 | 109 | 167 | 98.9 | 125 | 36.8 |
| 2 | 75.1 | 53.1 | 71.9 | 66.7 | 11.9 |
| 4 | 66.3 | 47.1 | 40.1 | 51.2 | 13.6 |
| 8 | 68.7 | 35.7 | 45.3 | 49.9 | 17.0 |
| 24 | BLOQ | 0.278 | 0.869 | 0.574 | NA |

TLZ-16 freebase Plasma PK parameters (IV, 3 mg/kg)

| PK parameters | Unit | R1 | R2 | R3 | Mean | SD | CV (%) |
|---|---|---|---|---|---|---|---|
| Cl_obs | mL/min/kg | 52.6 | 46.5 | 48.6 | 49.2 | 3.1 | 6.30 |
| $T_{1/2}$ | h | 1.66 | 2.14 | 4.37 | 2.73 | 1.44 | 53.0 |
| $C_0$ | ng/mL | 1713 | 1707 | 2045 | 1822 | 194 | 10.6 |
| $AUC_{last}$ | h * ng/mL | 937 | 1038 | 1027 | 1001 | 55 | 5.51 |
| $AUC_{Inf}$ | h * ng/mL | 950 | 1074 | 1030 | 1018 | 63 | 6.19 |
| $AUC_{\_\% Extrap}$_obs | % | 1.32 | 3.37 | 0.306 | 1.67 | 1.56 | 93.6 |
| $MRT_{Inf}$_obs | h | 1.09 | 1.52 | 1.08 | 1.23 | 0.25 | 20.6 |
| $AUC_{last}/D$ | h * mg/mL | 312 | 346 | 342 | 334 | 18 | 5.51 |
| $V_{ss}$_obs | L/kg | 3.43 | 4.26 | 3.16 | 3.61 | 0.57 | 15.8 |

| TLZ-16 freebase plasma PK parameters (POA, 10 mg/kg) | | | | | | | |
|---|---|---|---|---|---|---|---|
| PK parameters | Unit | R4 | R5 | R6 | Mean | SD | CV (%) |
| $T_{1/2}$ | h | 8.80 | 2.57 | 3.34 | 4.90 | 3.39 | 69.3 |
| $T_{max}$ | h | 0.5 | 0.25 | 0.5 | 0.417 | 0.144 | 34.6 |
| $C_{max}$ | ng/mL | 139 | 358 | 109 | 202 | 136 | 67.3 |
| $AUC_{last}$ | h * ng/mL | 615 | 924 | 825 | 788 | 158 | 20.1 |
| $AUC_{Inf}$ | h * ng/mL | 1486 | 925 | 829 | 1080 | 355 | 32.9 |
| $AUC_{\_\%\ Extrap}\_obs$ | % | 58.7 | 0.111 | 0.505 | 19.8 | 33.7 | 171 |
| $MRT_{Inf}\_obs$ | h | 13.6 | 4.19 | 5.68 | 7.84 | 5.08 | 64.8 |
| $AUC_{last}/D$ | h * mg/mL | 61.5 | 92.4 | 82.5 | 78.8 | 15.8 | 20.1 |
| F | % | 18.4 | 27.3 | 24.4 | 23.4 | 4.5 | 19.3 |

(2) TLZ-16 HCl

| TLZ-16 HCl concentration in plasma (POB, 10 mg/kg) | | | | | |
|---|---|---|---|---|---|
| | Conc. (ng/mL) | | | Mean | RSD |
| Time (h) | R13 | R14 | R15 | (ng/mL) | (ng/mL) |
| 0 | BLOQ | BLOQ | BLOQ | NA | NA |
| 0.25 | 236 | 239 | 385 | 287 | 85.2 |
| 0.5 | 225 | 217 | 356 | 266 | 78.0 |
| 1 | 130 | 149 | 173 | 151 | 21.5 |
| 2 | 135 | 129 | 115 | 126 | 10.3 |
| 4 | 109 | 60.3 | 79.2 | 82.8 | 24.6 |
| 8 | 44.3 | 15.6 | 14.1 | 24.7 | 17.0 |
| 24 | 0.356 | BLOQ | BLOQ | NA | NA |

Note:
BLOQ = below limit of quantitation (0.2 ng/mL)

| TLZ-16 HCl Plasma PK parameters (POB, 10 mg/kg) | | | | | | | |
|---|---|---|---|---|---|---|---|
| PK parameters | Unit | R13 | R14 | R15 | Mean | SD | CV (%) |
| $T_{1/2}$ | h | 2.39 | 1.98 | 1.92 | 2.09 | 0.25 | 12.1 |
| $T_{max}$ | h | 0.25 | 0.25 | 0.25 | 0.250 | 0.000 | 0.000 |
| $C_{max}$ | ng/mL | 236 | 239 | 385 | 287 | 85 | 29.7 |
| $AUC_{last}$ | h * ng/mL | 1216 | 658 | 798 | 891 | 290 | 32.6 |
| $AUC_{Inf}$ | h * ng/mL | 1217 | 703 | 837 | 919 | 267 | 29.0 |
| $AUC_{\_\%\ Extrap}\_obs$ | % | 0.101 | 6.34 | 4.66 | 3.70 | 3.23 | 87.2 |
| $MRT_{Inf}\_obs$ | h | 4.53 | 2.86 | 2.58 | 3.32 | 1.05 | 31.7 |
| $AUC_{last}/D$ | h * mg/mL | 122 | 65.8 | 79.8 | 89 | 29 | 32.6 |
| F | % | 35.9 | 20.7 | 24.7 | 27.1 | 7.9 | 29.0 |

(3) TLZ-16 maleate

| TLZ-16 maleate concentration in plasma (POC, 10 mg/kg) | | | | | |
|---|---|---|---|---|---|
| | Conc. (ng/mL) | | | Mean | RSD |
| Time (h) | R22 | R23 | R24 | (ng/mL) | (ng/mL) |
| 0 | BLOQ | BLOQ | BLOQ | NA | NA |
| 0.25 | 138 | 257 | 438 | 278 | 151 |
| 0.5 | 132 | 290 | 287 | 236 | 90.4 |
| 1 | 118 | 206 | 176 | 167 | 44.7 |
| 2 | 106 | 175 | 55.8 | 112 | 59.8 |
| 4 | 104 | 116 | 69.3 | 96.4 | 24.3 |
| 8 | 40.8 | 34.5 | 34.1 | 36.5 | 3.76 |
| 24 | BLOQ | BLOQ | BLOQ | NA | NA |

Note:
BLOQ = below limit of quantitation (0.2 ng/mL)

| TLZ-16 maleate Plasma PK parameters (POC, 10 mg/kg) | | | | | | | |
|---|---|---|---|---|---|---|---|
| PK parameters | Unit | R22 | R23 | R24 | Mean | SD | CV (%) |
| $T_{1/2}$ | h | 4.08 | 2.52 | 3.83 | 3.48 | 0.84 | 24.2 |
| $T_{max}$ | h | 0.25 | 0.5 | 0.25 | 0.333 | 0.144 | 43.3 |
| $C_{max}$ | ng/mL | 138 | 290 | 438 | 289 | 150 | 52.0 |

-continued

| TLZ-16 maleate Plasma PK parameters (POC, 10 mg/kg) | | | | | | | |
|---|---|---|---|---|---|---|---|
| PK parameters | Unit | R22 | R23 | R24 | Mean | SD | CV (%) |
| $AUC_{last}$ | h * ng/mL | 725 | 1007 | 709 | 814 | 168 | 20.6 |
| $AUC_{Inf}$ | h * ng/mL | 965 | 1132 | 898 | 998 | 121 | 12.1 |
| $AUC_{\_\%\ Extrap\_}obs$ | % | 24.9 | 11.1 | 21.0 | 19.0 | 7.1 | 37.5 |
| $MRT_{Inf}\_obs$ | h | 5.88 | 3.67 | 4.80 | 4.78 | 1.11 | 23.2 |
| $AUC_{last}/D$ | h * mg/mL | 72.5 | 101 | 70.9 | 81 | 17 | 20.6 |
| F | % | 21.7 | 33.4 | 21.3 | 25.5 | 6.9 | 26.9 |

(4) TLZ-16 mesylate

| TLZ-16 mesylate concentration in plasma (POD, 10 mg/kg) | | | | | |
|---|---|---|---|---|---|
| | Conc. (ng/mL) | | | Mean | RSD |
| Time (h) | R31 | R32 | R33 | (ng/mL) | (ng/mL) |
| 0 | BLOQ | BLOQ | BLOQ | NA | NA |
| 0.25 | 227 | 253 | 256 | 245 | 15.9 |
| 0.5 | 192 | 233 | 338 | 254 | 75.3 |
| 1 | 162 | 197 | 208 | 189 | 24.0 |
| 2 | 211 | 180 | 271 | 221 | 46.3 |
| 4 | 208 | 155 | 122 | 162 | 43.4 |
| 8 | 70.3 | 40.7 | 35.2 | 48.7 | 18.9 |
| 24 | BLOQ | 0.454 | BLOQ | NA | NA |

Note:
BLOQ = below limit of quantitation (0.2 ng/mL)

| TLZ-16 mesylate plasma PK parameters (POD, 10 mg/kg) | | | | | | | |
|---|---|---|---|---|---|---|---|
| PK parameters | Unit | R31 | R32 | R33 | Mean | SD | CV (%) |
| $T_{1/2}$ | h | 3.54 | 2.40 | 2.06 | 2.67 | 0.77 | 29.0 |
| $T_{max}$ | h | 0.25 | 0.25 | 0.5 | 0.333 | 0.144 | 43.3 |
| $C_{max}$ | ng/mL | 227 | 253 | 338 | 273 | 58 | 21.3 |
| $AUC_{last}$ | h * ng/mL | 1331 | 1444 | 1190 | 1322 | 127 | 9.64 |
| $AUC_{Inf}$ | h * ng/mL | 1690 | 1446 | 1294 | 1477 | 200 | 13.5 |
| $AUC_{\_\%\ Extrap\_}obs$ | % | 21.2 | 0.109 | 8.09 | 9.82 | 10.7 | 109 |
| $MRT_{Inf}\_obs$ | h | 5.40 | 4.15 | 3.26 | 4.27 | 1.07 | 25.2 |
| $AUC_{last}/D$ | h * mg/mL | 133 | 144 | 119 | 132 | 13 | 9.64 |
| F | % | 39.9 | 42.6 | 38.1 | 40.2 | 2.2 | 5.58 |

(5) TLZ-16 oxalate

| TLZ-16 oxalate concentration in plasma (POE, 10 mg/kg) | | | | | |
|---|---|---|---|---|---|
| | Conc. (ng/mL) | | | Mean | RSD |
| Time (h) | R40 | R41 | R42 | (ng/mL) | (ng/mL) |
| 0 | BLOQ | BLOQ | BLOQ | NA | NA |
| 0.25 | 302 | 368 | 131 | 267 | 122 |
| 0.5 | 270 | 309 | 148 | 242 | 84.0 |
| 1 | 143 | 200 | 121 | 155 | 40.8 |
| 2 | 70.8 | 86.0 | 156 | 104 | 45.4 |
| 4 | 63.1 | 120 | 95.0 | 92.7 | 28.5 |
| 8 | 10.1 | 56.8 | 29.1 | 32.0 | 23.5 |
| 24 | BLOQ | BLOQ | BLOQ | NA | NA |

Note:
BLOQ = below limit of quantitation (0.2 ng/mL)

| TLZ-16 oxalate Plasma PK parameters (POE, 10 mg/kg) | | | | | | | |
|---|---|---|---|---|---|---|---|
| PK parameters | Unit | R40 | R41 | R42 | Mean | SD | CV (%) |
| $T_{1/2}$ | h | 2.02 | 4.98 | 2.46 | 3.15 | 1.60 | 50.8 |
| $T_{max}$ | h | 0.25 | 0.25 | 2 | 0.833 | 1.010 | 121 |
| $C_{max}$ | ng/mL | 302 | 368 | 156 | 275 | 108 | 39.4 |
| $AUC_{last}$ | h * ng/mL | 600 | 960 | 756 | 772 | 181 | 23.4 |
| $AUC_{Inf}$ | h * ng/mL | 629 | 1369 | 859 | 952 | 378 | 39.7 |

-continued

| TLZ-16 oxalate Plasma PK parameters (POE, 10 mg/kg) | | | | | | | |
|---|---|---|---|---|---|---|---|
| PK parameters | Unit | R40 | R41 | R42 | Mean | SD | CV (%) |
| $AUC_{\_\% Extrap\_}obs$ | % | 4.67 | 29.8 | 12.0 | 15.5 | 12.9 | 83.5 |
| $MRT_{Inf\_}obs$ | h | 2.59 | 6.60 | 3.95 | 4.38 | 2.04 | 46.6 |
| $AUC_{last}/D$ | h * mg/mL | 60.0 | 96.0 | 75.6 | 77.2 | 18.1 | 23.4 |
| F | % | 18.5 | 28.8 | 25.3 | 24.2 | 5.2 | 21.5 |

(6) TLZ-16 sulfate

| TLZ-16 sulfate concentration in plasma (POF, 10 mg/kg) | | | | | |
|---|---|---|---|---|---|
| | Conc. (ng/mL) | | | Mean | RSD |
| Time (h) | R49 | R50 | R51 | (ng/mL) | (ng/mL) |
| 0 | BLOQ | BLOQ | BLOQ | NA | NA |
| 0.25 | 231 | 226 | 349 | 269 | 69.6 |
| 0.5 | 229 | 223 | 401 | 284 | 101 |
| 1 | 117 | 161 | 240 | 173 | 62.3 |
| 2 | 119 | 152 | 189 | 153 | 35.0 |
| 4 | 103 | 110 | 203 | 139 | 55.8 |
| 8 | 22.4 | 39.9 | 87.8 | 50.0 | 33.9 |
| 24 | BLOQ | BLOQ | BLOQ | NA | NA |

Note:
BLOQ = below limit of quantitation (0.2 ng/mL)

| TLZ-16 sulfate plasma PK parameters (POF, 10 mg/kg) | | | | | | | |
|---|---|---|---|---|---|---|---|
| PK parameters | Unit | R49 | R50 | R51 | Mean | SD | CV (%) |
| $T_{1/2}$ | h | 2.37 | 3.05 | 4.97 | 3.46 | 1.35 | 39.0 |
| $T_{max}$ | h | 0.25 | 0.25 | 0.5 | 0.333 | 0.144 | 43.3 |
| $C_{max}$ | ng/mL | 231 | 226 | 401 | 286 | 100 | 34.8 |
| $AUC_{last}$ | h * ng/mL | 764 | 899 | 1486 | 1049 | 384 | 36.6 |
| $AUC_{Inf}$ | h * ng/mL | 840 | 1074 | 2115 | 1343 | 679 | 50.5 |
| $AUC_{\_\% Extrap\_}obs$ | % | 9.10 | 16.3 | 29.8 | 18.4 | 10.5 | 57.0 |
| $MRT_{Inf\_}obs$ | h | 3.53 | 4.44 | 6.73 | 4.90 | 1.65 | 33.6 |
| $AUC_{last}/D$ | h * mg/mL | 76.4 | 89.9 | 149 | 105 | 38 | 36.6 |
| F | % | 24.8 | 31.7 | 44.5 | 33.7 | 10.0 | 29.8 |

The pharmacokinetic study shows that the inventive salts of compound (1) have better bioavailability and biodistribution.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A crystalline salt form of Compound (1)

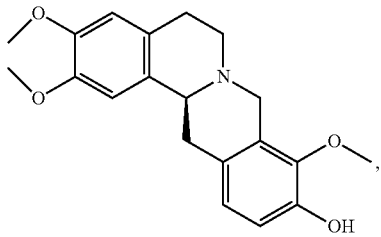

wherein the crystalline salt form is a hydrochloride salt having an X-ray powder diffraction pattern comprising peaks at approximately 9.7, 10.1, 14.3, 15.0, 17.5, 18.9, 21.9, and 23.7 degrees 2θ;
a oxalate salt having an X-ray powder diffraction pattern comprising peaks at approximately 11.7, 13.0, 15.4, 16.3, 19.6, 22.1, and 24.5 degrees 2θ;
a maleate salt having an X-ray powder diffraction pattern comprising peaks at approximately 8.0, 10.4, 12.4, 14.0, 15.3, 16.4, 19.3, 21.5, and 23.3 degrees 2θ;
a sulfate salt having an X-ray powder diffraction pattern comprising peaks at approximately 8.4, 12.6, 13.7, 16.7, 21.0, 21.8, 22.2, and 23.4 degrees 2θ; or
a mesylate salt having an X-ray powder diffraction pattern comprising peaks at approximately 7.9, 11.3, 12.6, 12.9, 14.7, 16.1, 20.0, and 20.7 degrees 2θ.

2. The crystalline salt form according to claim 1, wherein the crystalline salt form is a hydrochloride salt having an X-ray powder diffraction pattern comprising peaks at approximately 9.7, 10.1, 14.3, 15.0, 17.5, 18.9, 21.9, and 23.7 degrees 2θ.

3. The crystalline salt form according to claim 1, wherein the crystalline salt form is a hydrochloride salt having a differential scanning calorimetry thermogram endotherm $T_{onset}$ at approximately 252° C. and an X-ray powder diffraction pattern comprising peaks at approximately 9.7, 10.1, 14.3, 15.0, 17.5, 18.9, 21.9, and 23.7 degrees 2θ.

4. The crystalline salt form according to claim 1, wherein the crystalline salt form is a oxalate salt having an X-ray powder diffraction pattern comprising peaks at approximately 11.7, 13.0, 15.4, 16.3, 19.6, 22.1, and 24.5 degrees 2θ.

5. The crystalline salt form according to claim 1, wherein the crystalline salt form is a oxalate salt having a differential scanning calorimetry thermogram endotherm $T_{onset}$ at approximately 205° C. and an X-ray powder diffraction pattern comprising peaks at approximately 11.7, 13.0, 15.4, 16.3, 19.6, 22.1, and 24.5 degrees 2θ.

6. The crystalline salt form according to claim 1, wherein the crystalline salt form is a maleate salt having an X-ray powder diffraction pattern comprising peaks at approximately 8.0, 10.4, 12.4, 14.0, 15.3, 16.4, 19.3, 21.5, and 23.3 degrees 2θ.

7. The crystalline salt form according to claim 1, wherein the crystalline salt form is a maleate salt having a differential scanning calorimetry thermogram endotherm $T_{onset}$ at approximately 193° C. and an X-ray powder diffraction pattern comprising peaks at approximately 8.0, 10.4, 12.4, 14.0, 15.3, 16.4, 19.3, 21.5, and 23.3 degrees 2θ.

8. The crystalline salt form according to claim 1, wherein the crystalline salt form is a sulfate salt having an X-ray powder diffraction pattern comprising peaks at approximately 8.4, 12.6, 13.7, 16.7, 21.0, 21.8, 22.2, and 23.4 degrees 2θ.

9. The crystalline salt form according to claim 1, wherein the crystalline salt form is a sulfate salt having a differential scanning calorimetry thermogram endotherm $T_{onset}$ at approximately 229° C. and an X-ray powder diffraction pattern comprising peaks at approximately 8.4, 12.6, 13.7, 16.7, 21.0, 21.8, 22.2, and 23.4 degrees 2θ.

10. The crystalline salt form according to claim 1, wherein the crystalline salt form is a mesylate salt having an X-ray powder diffraction pattern comprising peaks at approximately 7.9, 11.3, 12.6, 12.9, 14.7, 16.1, 20.0, and 20.7 degrees 2θ.

11. The crystalline salt form according to claim 1, wherein the crystalline salt form is a mesylate salt having a differential scanning calorimetry thermogram endotherm $T_{onset}$ at approximately 238° C. and an X-ray powder diffraction pattern comprising peaks at approximately 7.9, 11.3, 12.6, 12.9, 14.7, 16.1, 20.0, and 20.7 degrees 2θ.

12. A pharmaceutical composition comprising the crystalline salt form of claim 1, and a pharmaceutically acceptable carrier.

13. The pharmaceutical composition of claim 12, which is a single unit dosage form.

14. The pharmaceutical composition according to claim 12, wherein the crystalline salt form is in substantially pure form.

15. A method of treating chronic pain, anxiety, insomnia, hyperlipidemia, hypercholesterolemia, hypertriglyceridemia, hepatic steatosis, and metabolic syndrome in a mammal comprising administering to the mammal a therapeutically-effective amount of the pharmaceutical composition according to claim 12.

16. A method of treating chronic pain, anxiety, insomnia, hyperlipidemia, hypercholesterolemia, hypertriglyceridemia, hepatic steatosis, and metabolic syndrome in a mammal comprising administering to the mammal a pharmaceutical composition comprising a therapeutically-effective amount of the crystalline salt form according to claim 1.

17. The method according claim 16, wherein the therapeutically-effective amount of the crystalline salt form is about 5 mg to about 500 mg.

18. A pharmaceutical composition comprising the crystalline salt form of claim 2, and a pharmaceutically acceptable carrier.

19. A pharmaceutical composition comprising the crystalline salt form of claim 4, and a pharmaceutically acceptable carrier.

* * * * *